United States Patent
Yarkoni et al.

(10) Patent No.: US 9,624,469 B2
(45) Date of Patent: Apr. 18, 2017

(54) REGULATORY IMMUNE CELLS WITH ENHANCED TARGETED CELL DEATH EFFECT

(75) Inventors: Shai Yarkoni, Rehovot (IL); Nadir Askenasy, Tel-Aviv (IL)

(73) Assignee: Cellect Biotherapeutics Ltd. (IL)

( * ) Notice: Subject to any disclaimer, the term of this patent is extended or adjusted under 35 U.S.C. 154(b) by 10 days.

(21) Appl. No.: 13/811,374

(22) PCT Filed: Jul. 21, 2011

(86) PCT No.: PCT/IL2011/000588
§ 371 (c)(1),
(2), (4) Date: Jan. 21, 2013

(87) PCT Pub. No.: WO2012/011113
PCT Pub. Date: Jan. 26, 2012

(65) Prior Publication Data
US 2013/0129771 A1    May 23, 2013

Related U.S. Application Data

(60) Provisional application No. 61/366,545, filed on Jul. 22, 2010.

(51) Int. Cl.
| | |
|---|---|
| *A01N 63/00* | (2006.01) |
| *C12N 5/0783* | (2010.01) |
| *A61K 35/16* | (2015.01) |
| *A61K 35/17* | (2015.01) |
| *A61K 35/26* | (2015.01) |
| *A61K 39/00* | (2006.01) |
| *C12N 5/00* | (2006.01) |

(52) U.S. Cl.
CPC ............ *C12N 5/0637* (2013.01); *A61K 35/16* (2013.01); *A61K 35/17* (2013.01); *A61K 35/26* (2013.01); *A61K 39/001* (2013.01); *A61K 39/0008* (2013.01); *C12N 5/0006* (2013.01); *A61K 2039/5158* (2013.01); *C12N 2501/48* (2013.01)

(58) Field of Classification Search
None
See application file for complete search history.

(56) References Cited

U.S. PATENT DOCUMENTS

| | | |
|---|---|---|
| 2003/0147865 A1* | 8/2003 | Salomon et al. .......... 424/93.21 |
| 2003/0219419 A1 | 11/2003 | Shirwan |
| 2004/0018170 A1 | 1/2004 | Shirwan |
| 2004/0228848 A1 | 11/2004 | Har-Noy |
| 2007/0172947 A1 | 7/2007 | Shirwan |
| 2009/0142308 A1 | 6/2009 | Orban et al. |
| 2010/0092488 A1 | 4/2010 | Suzumura et al. |
| 2010/0260781 A1 | 10/2010 | Murray |
| 2010/0310588 A1 | 12/2010 | Bluestone et al. |

FOREIGN PATENT DOCUMENTS

| | | |
|---|---|---|
| EP | 1241249 A1 | 9/2002 |
| WO | 2010017220 A1 | 2/2010 |

OTHER PUBLICATIONS

Lundy et al., Inf. and Immun. vol. 70: 812-819.*
Rus et al., 2007, J. Immunol. vol. 178: 3962-72.*
O'shea et al. 2002, Nat. Reviews, vol. 21: 37-45.*
Cnop et al., 2005, DIabetes, vol. 54: S97-S107.*
Baatar et al., 2007, J. Immunol. vol. 178: 4891-4900.*
Cheung et al., 2004, Pancreas. vol. 30: 105-114.*
Venet et al., J. Immunol. vol. 177: 6540-6547.*
Yolcu et al., 2008, J. Immunol. vol. 181: 931-939.*
Stephens et al., 2004, Int. Immunol. vol. 16: 365-375.*
Askenasy, N. et al., "Mechanisms of T regulatory cell function", Autoimmunity Reviews, 7:370-375 (2008).
Jin et al., "Simultaneous stimulation of Fas-mediated apoptosis and blockade of costimulation prevent autoimmune diabetes in mice induced by multiple low-dose streptozotocin", Gene Therapy, 11:982-991 (2004).
Miyara, M. et al., "Natural regulatory T cells: mechanisms of suppression", TRENDS in Molecular Medicine, 13(3):108-116, 2007.
Shevach, E. M., "Mechanisms of Foxp3+ T Regulatory Cell-Mediated Suppression", Immunity, 30:636-645 (2009).
Sojka, D. K., et al., "Mechanisms of regulatory T-cell suppression—a diverse arsenal for a moving target", Immunology, 123:13-22 (2008).
Tang et al., "In Vitro-expanded Antigen-specific Regulatory T Cells Suppress Autoimmune Diabetes", The Journal of Experimental Medicine, 199(11) 1455-1465 (2004).
Vignali et al., "How regulatory T cells work", Nat. Rev. Immunol., 8(7):523-532 (2008).
Von Boehmer, H., "Mechanisms of suppression by suppressor T cells", H. Nat. Immunol., 6:338-344 (2005).
Yarkoni et al., "Involvement of IL-2 in homeostasis of regulatory T cells: The IL-2 cycle", BioEssays, 30:875-888 (2008).

(Continued)

*Primary Examiner* — Amy Juedes
(74) *Attorney, Agent, or Firm* — Wood, Phillips, Katz, Clark & Mortimer

(57) ABSTRACT

An isolated immune regulatory cell having an exogenous cell death-inducing moiety attached to a surface thereof is disclosed herein. Additionally, a molecule comprising a cell death-inducing moiety heterologously attached to an immune regulatory cell-specific binding moiety is disclosed herein. Methods of generating and using same as well as pharmaceutical compositions comprising same are also disclosed.

4 Claims, 28 Drawing Sheets

(56) References Cited

OTHER PUBLICATIONS

Yolcu et al., "Cell Membrane Modification for Rapid Display of Proteins as a Novel Means of Immunomodulation: FasL-Decorated Cells Prevent Islet Graft Rejection", Immunity, 17:795-808 (2002).
Yolcu et al., "Apoptosis as a mechanism of T-regulatory cell homeostasis and suppression", Immunology and Cell Biology, 86:650-658 (2008).

* cited by examiner

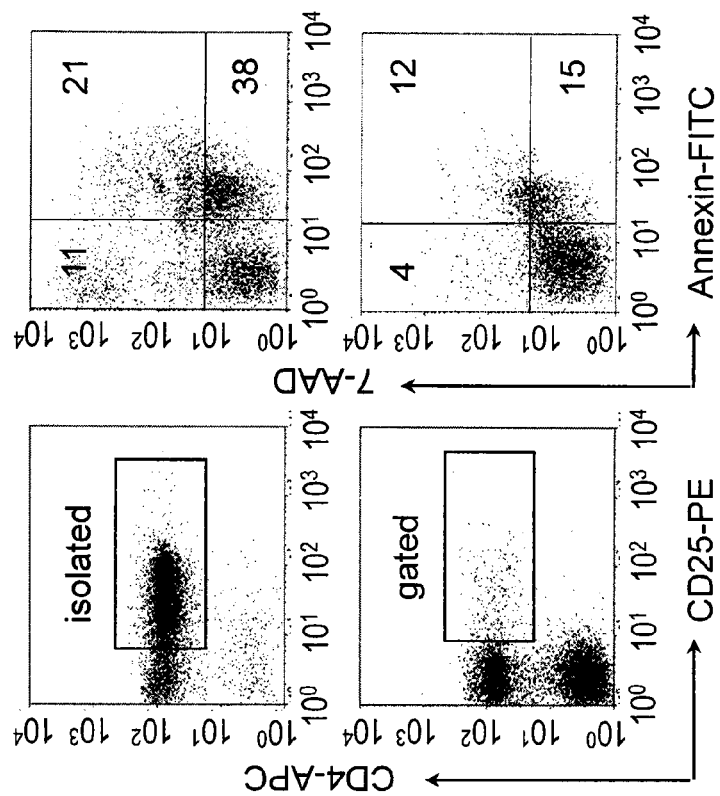
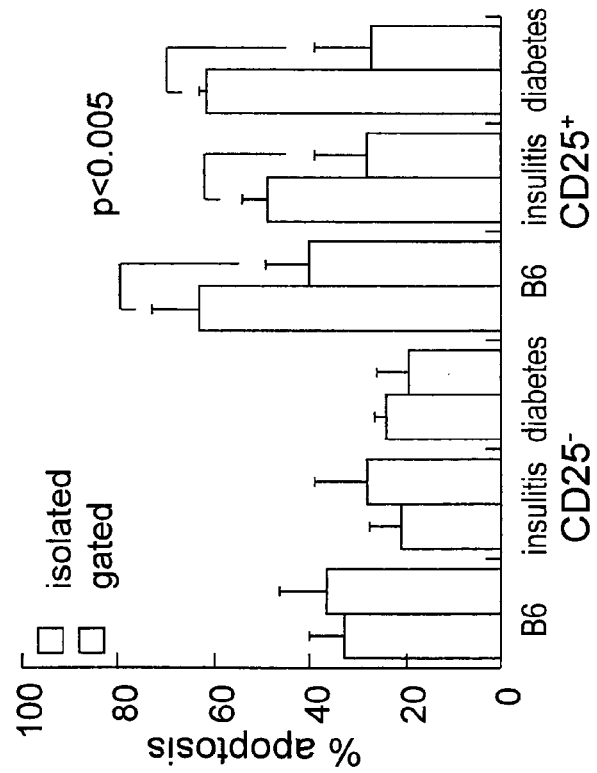

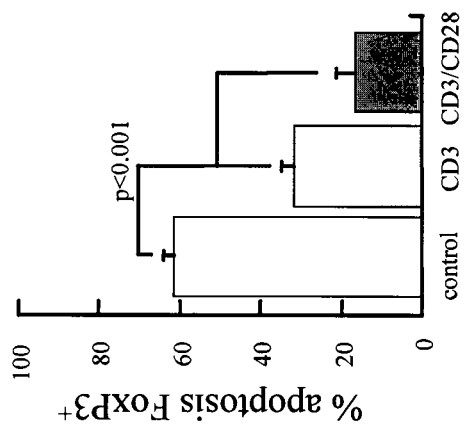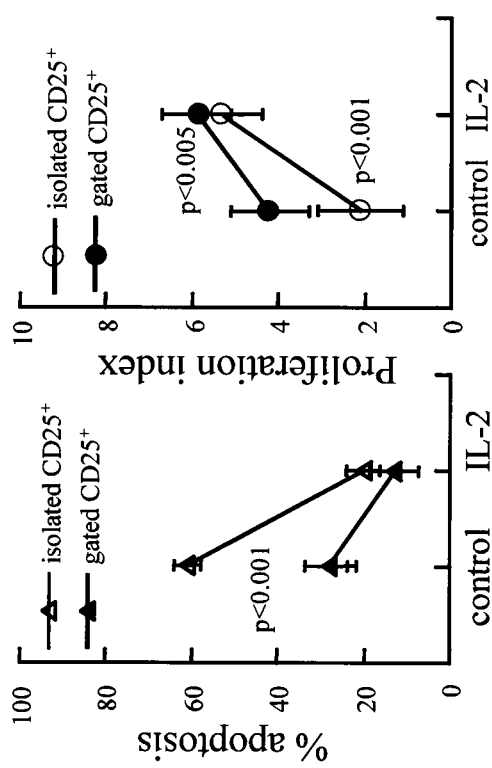

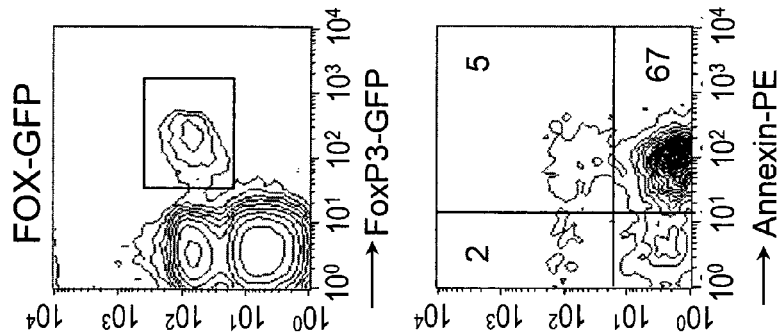
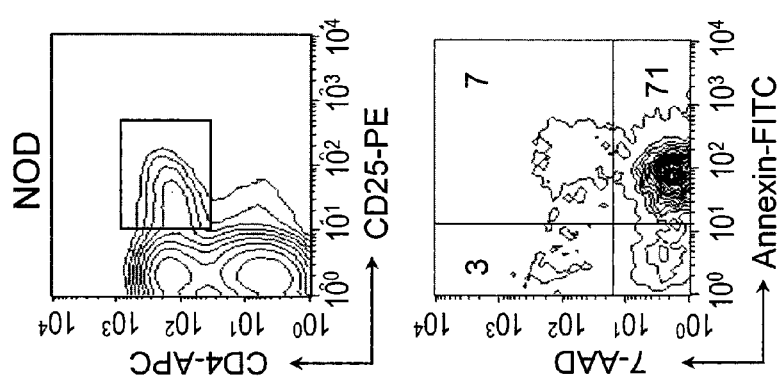
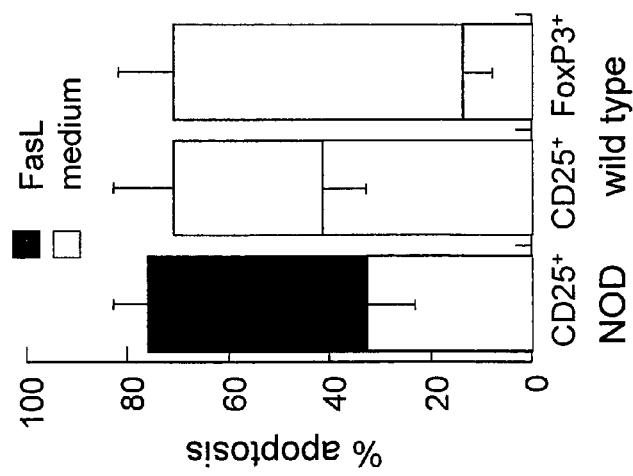

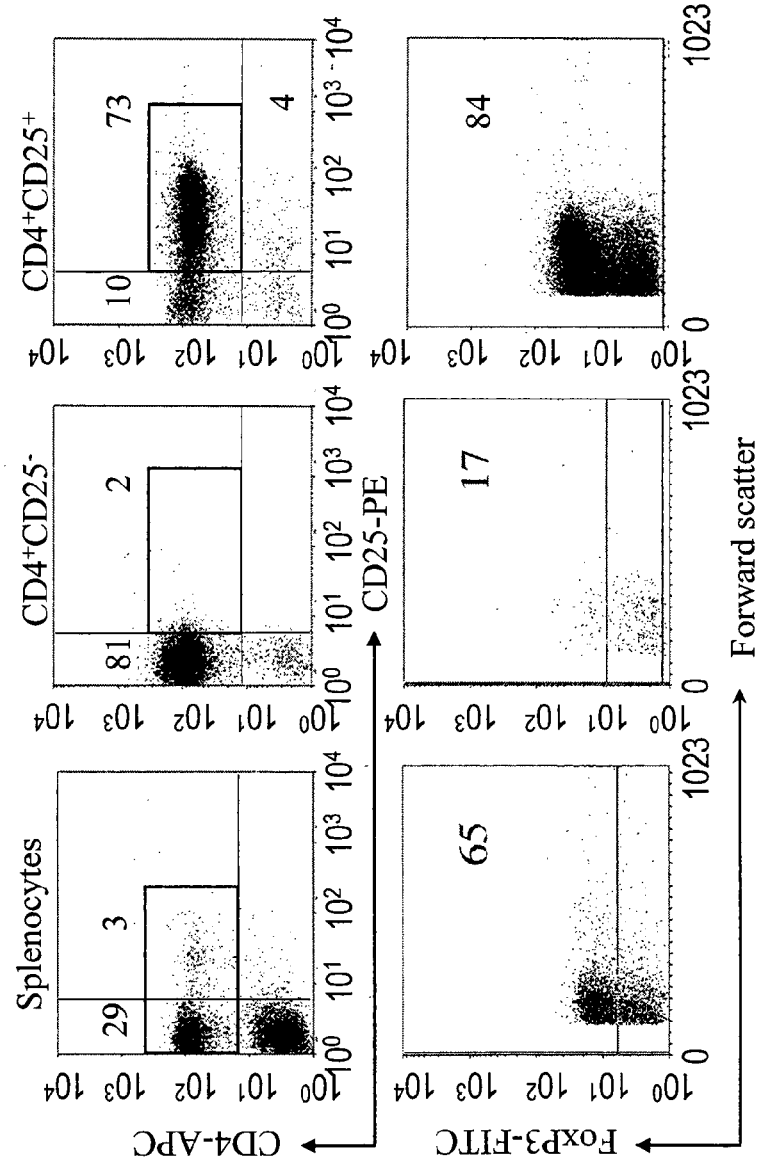

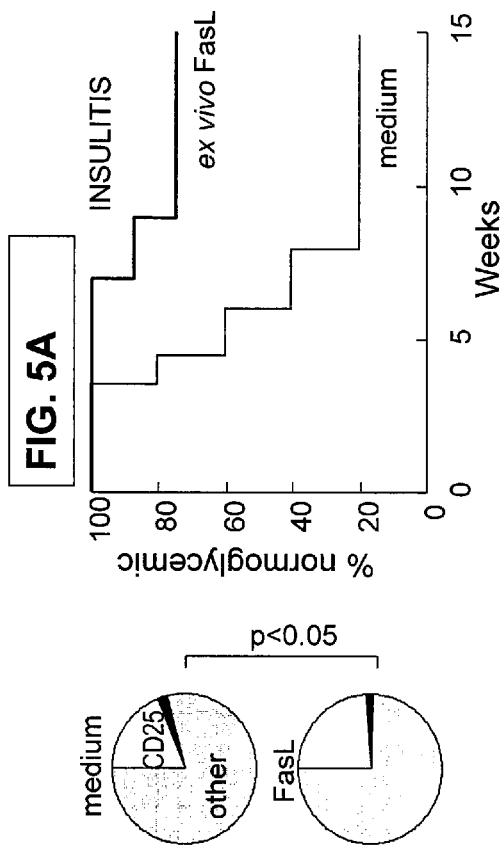
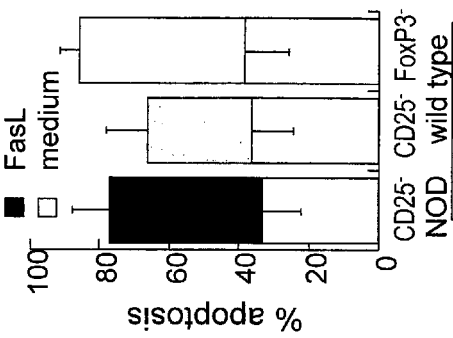
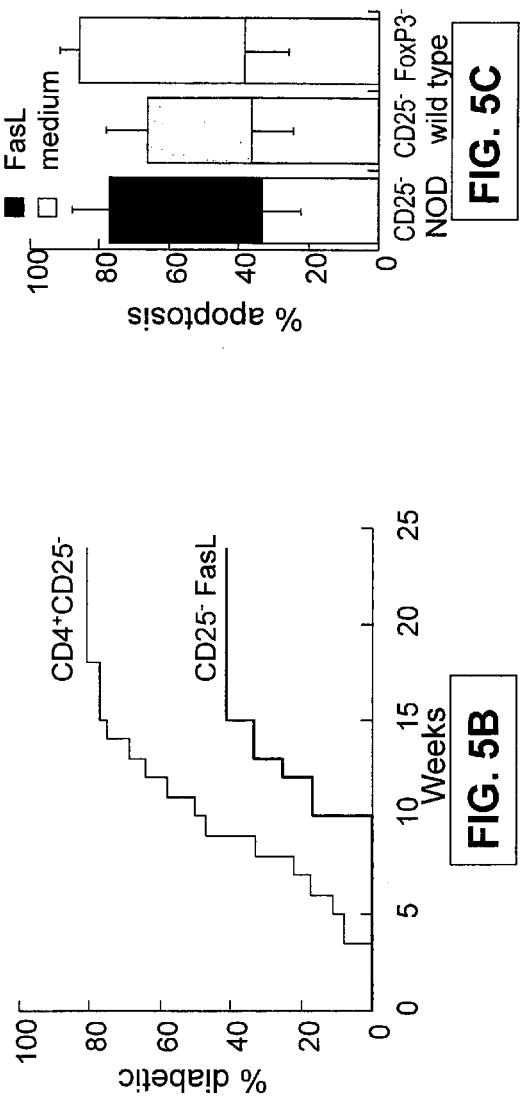

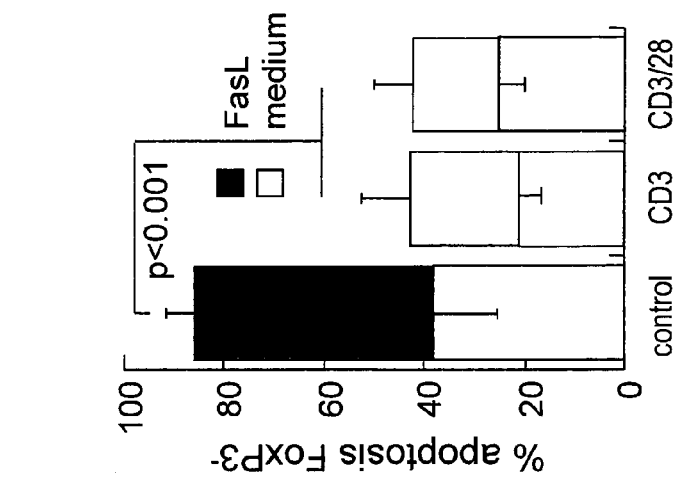
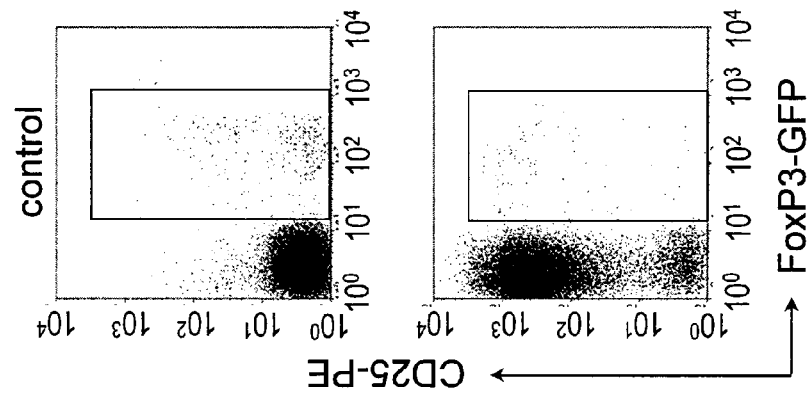
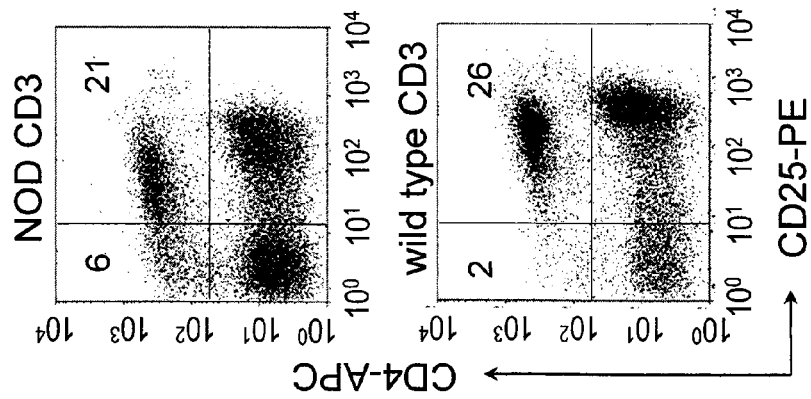

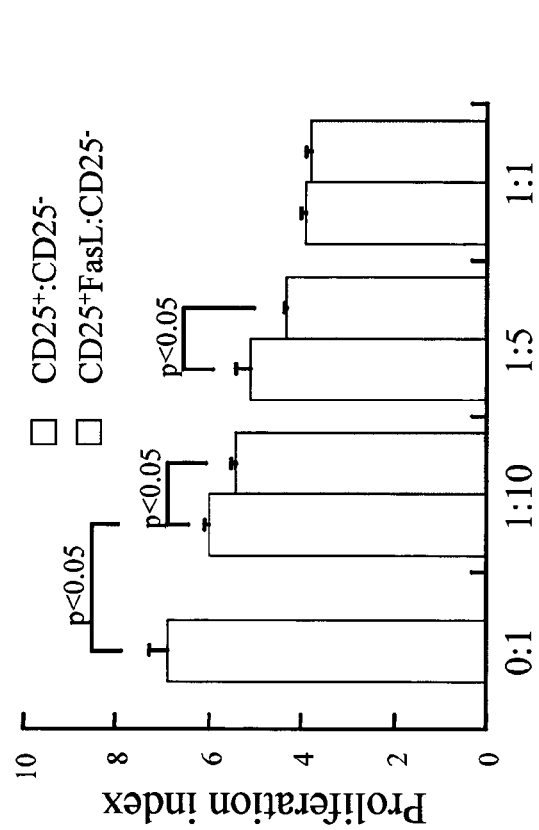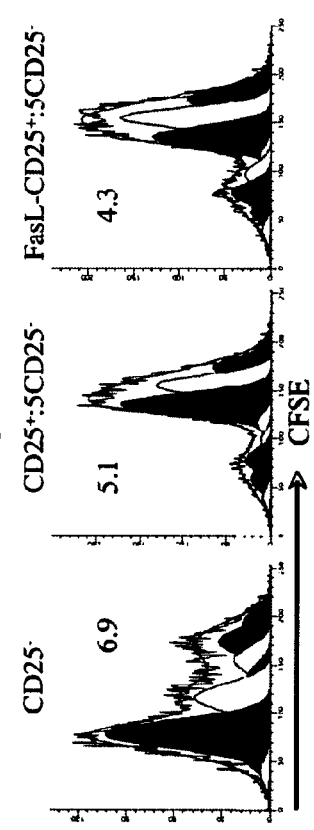

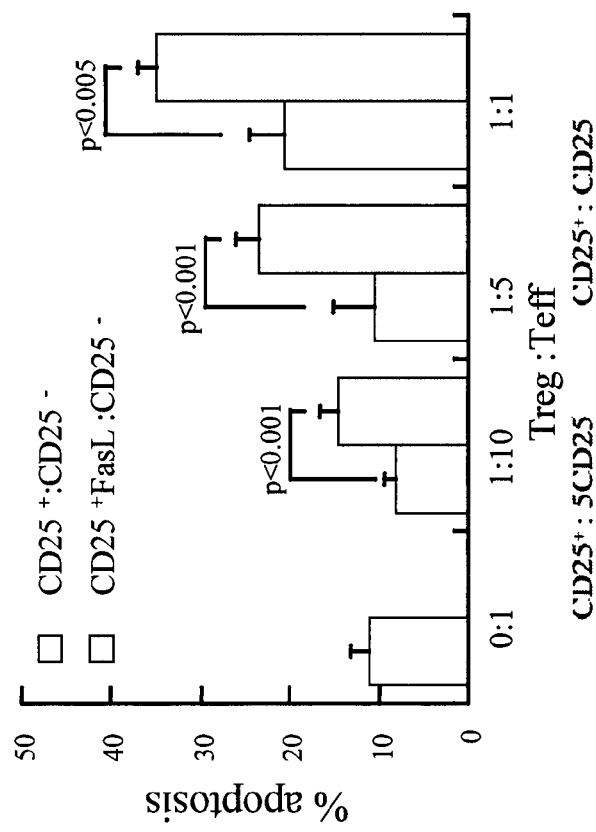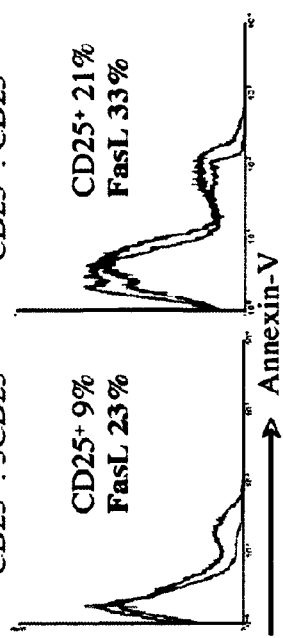
FIG. 6E
FIG. 6F
FIG. 6G

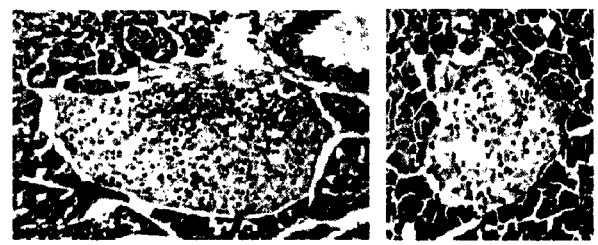
FIG. 7C
FIG. 7D
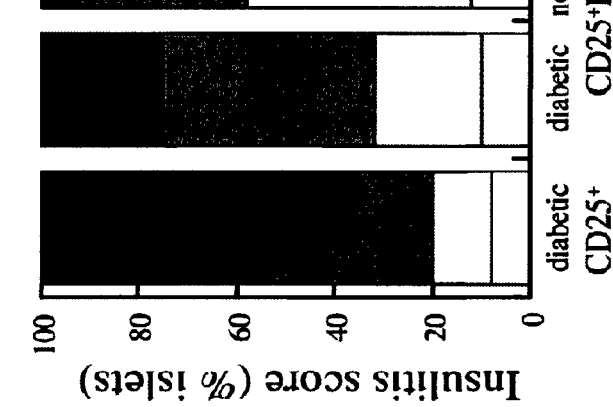
FIG. 7B
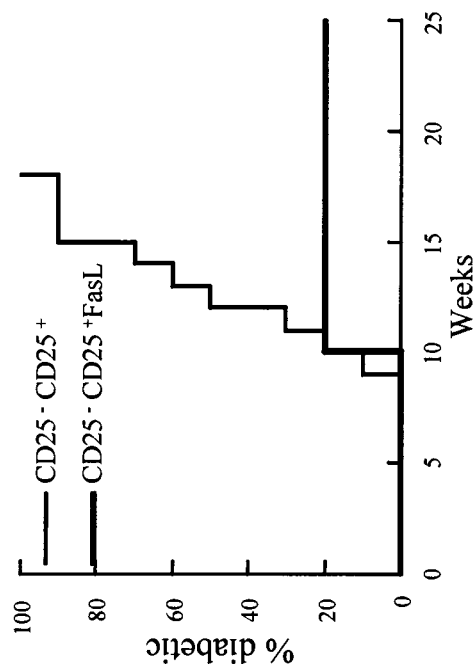
FIG. 7A

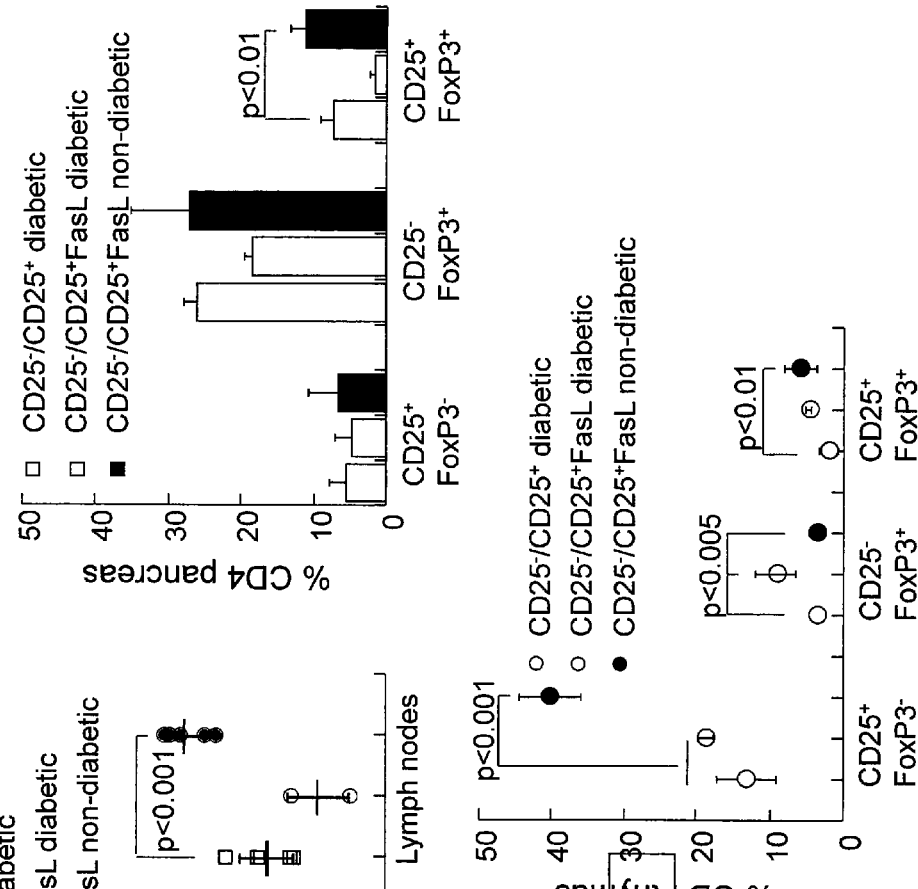
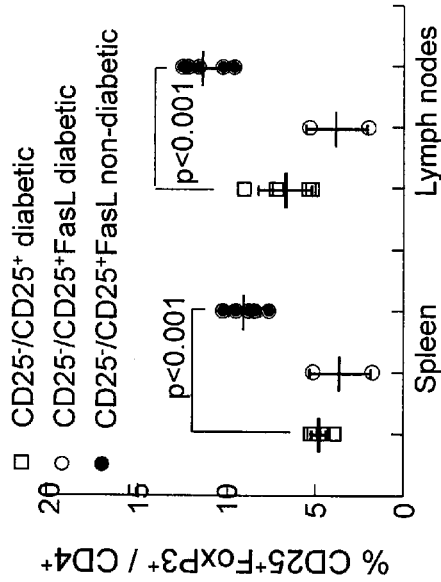

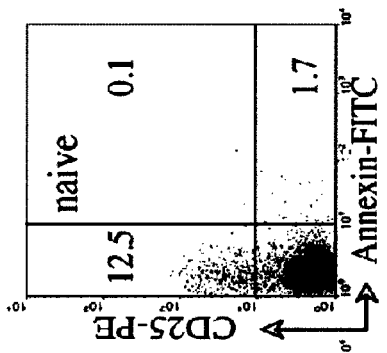
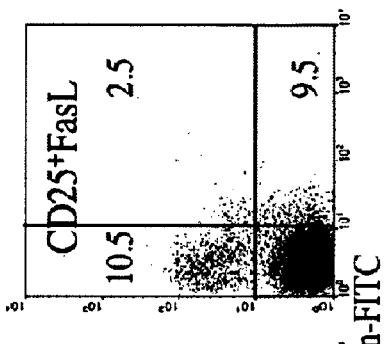
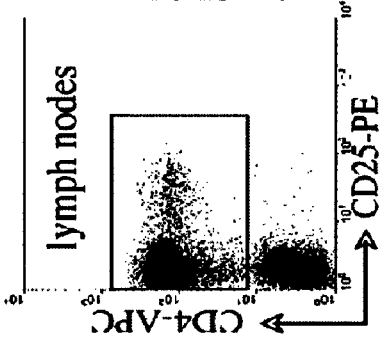
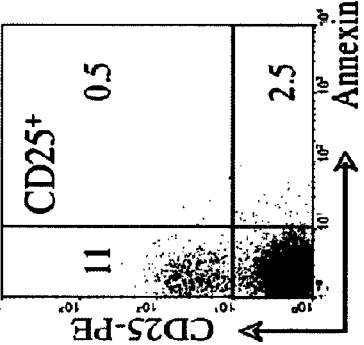
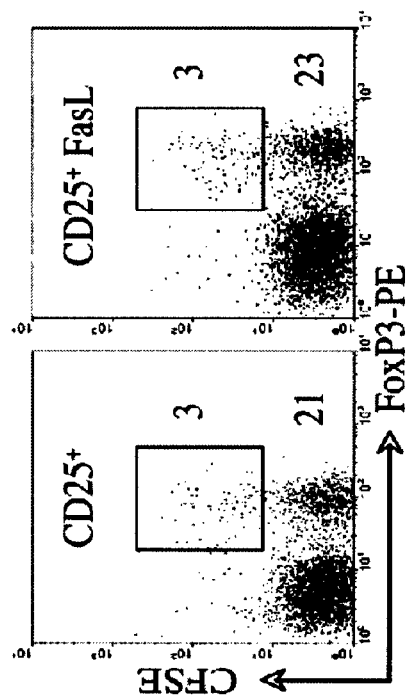
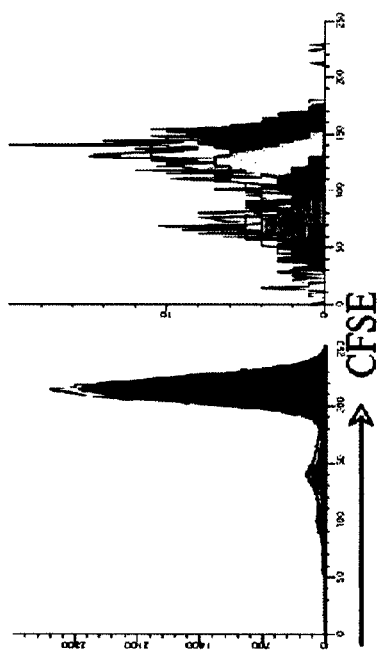

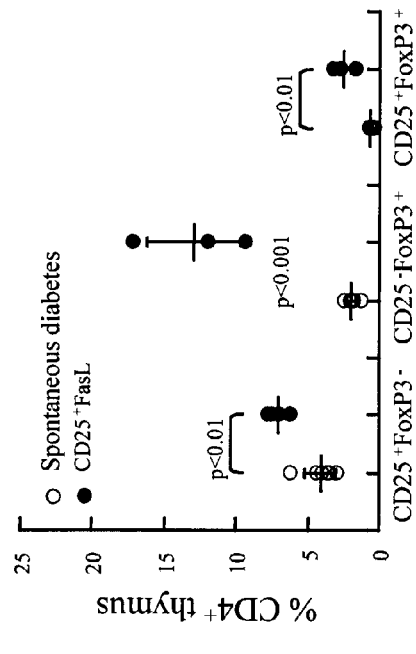
FIG. 9D
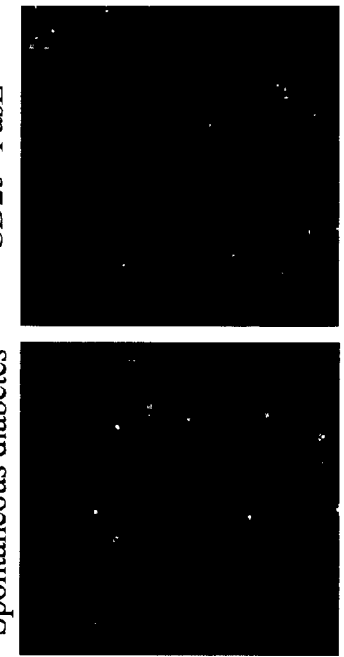
FIG. 9G
FIG. 9F
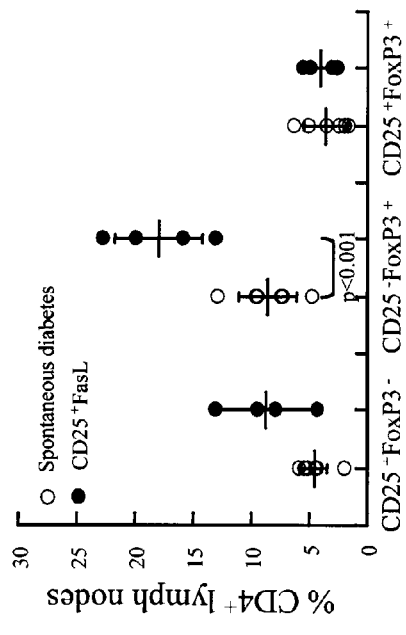
FIG. 9C
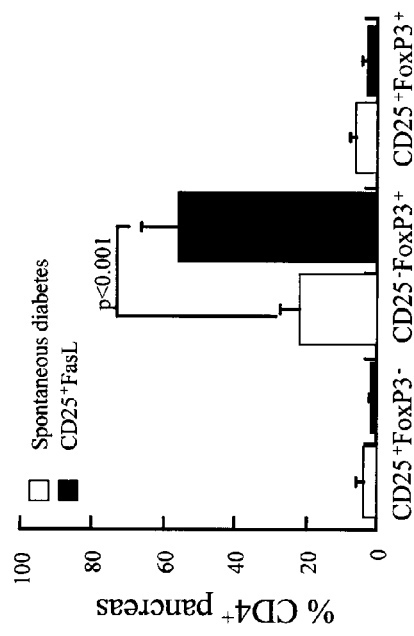
FIG. 9E

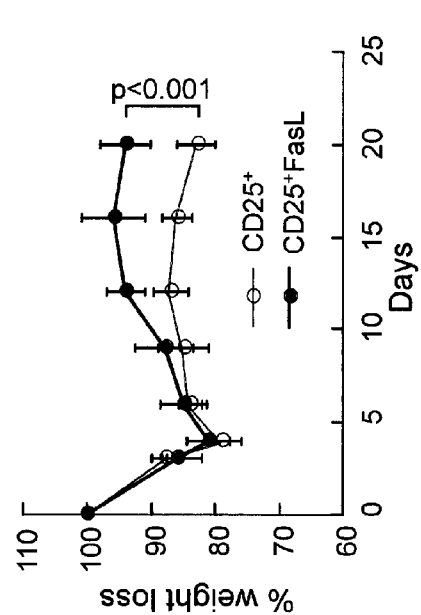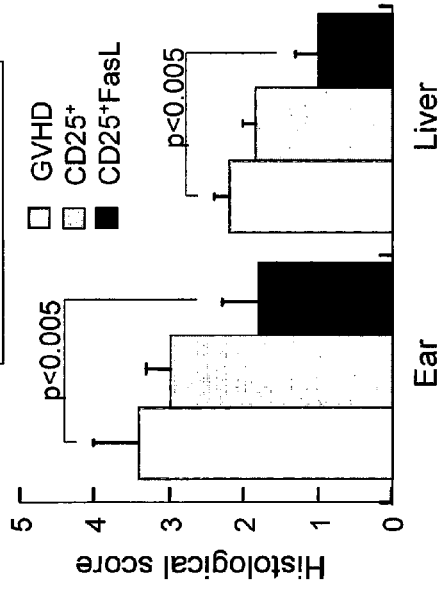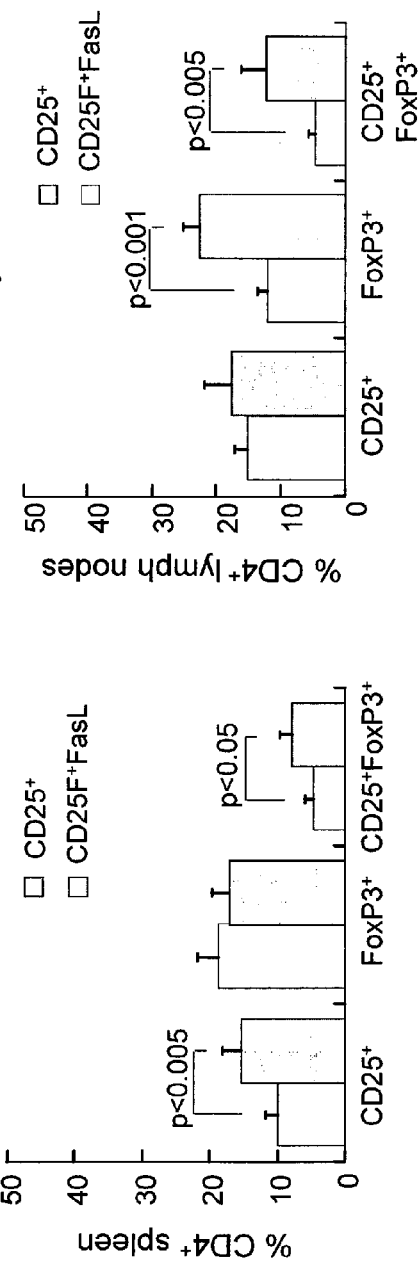

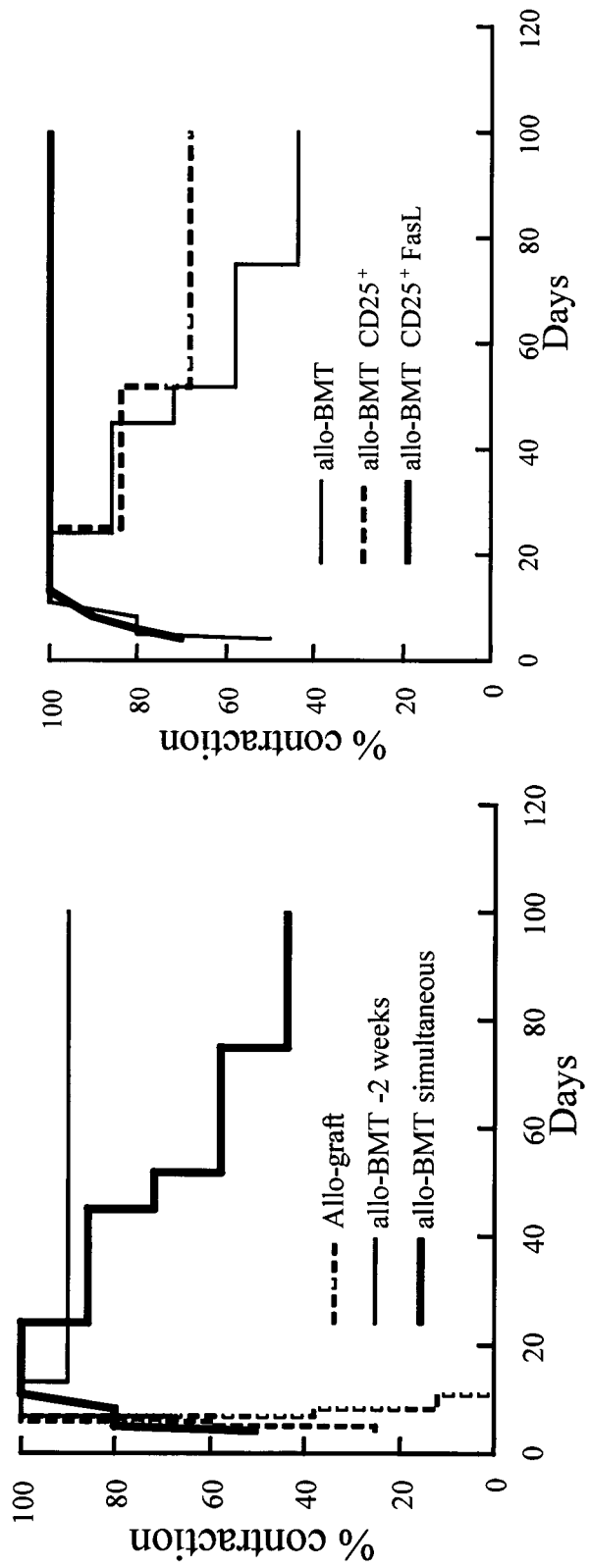

REGULATORY IMMUNE CELLS WITH ENHANCED TARGETED CELL DEATH EFFECT

RELATED APPLICATION DATA

This application is the U.S. National Stage of International Application No. PCT/IL2011/000588, filed Jul. 21, 2011, which claims the benefit of U.S. Provisional Application No. 61/366,545, filed Jul. 22, 2010, the contents of each of which are herein expressly incorporated by reference for all purposes.

FIELD AND BACKGROUND OF THE INVENTION

The present invention, in some embodiments thereof, relates to regulatory immune cells with enhanced apoptotic activity and, more particularly, but not exclusively, to the use thereof for immunomodulation, for treating or for preventing immune related disorders.

Disorders associated with regulatory immune cells include inter alia autoimmune diseases such as for example diabetes type 1, multiple sclerosis, inflammatory bowel disease, chronic inflammatory diseases such as infections, cancer, induced disorders such as graft versus host disease and induced transplant tolerance.

Immunotherapy is a highly desired treatment of such human diseases. The basis for immunotherapy is the manipulation of the immune response, particularly the responses of T cells, which possess complex and subtle systems for controlling their interactions, utilizing numerous receptors and soluble factors for the process. Healthy immune system generally reacts against harmful pathogens while remaining specifically tolerant to autologous tissues. Failure of such self tolerance can result in autoimmune disease, while a failure to respond appropriately can lead to infection, and may result in the growth of tumor cells. For most autoimmune diseases and undesired immune responses, no effective therapeutic agents exist. For example, current therapeutic strategies are often based on chemically induced immunosuppression, which can result in undesirable side effects on the kidney and other organs.

Deficiency or dysfunction of regulatory immune cells has been implicated in the pathogenesis of these diseases. In particular, the suppressor cells were shown to have a particularly important role in maintaining immune system homeostasis. A reduction in their number or function can also elicit tumor immunity, whereas their antigen-specific population expansion can establish transplantation tolerance.

Previous reports have indicated that T regulatory cell elicit suppression of reactive immune cells by several mechanisms including modulation of the cytokine environment at the site of inflammation and by suppression of proliferation and/or cytokine production by effector T cells. The mechanism which involves physical elimination of cytotoxic cells is unanimously considered as a minor mechanism of suppression within the extensive data relating to the functional inhibition of naïve and pathogenic T cells [von Boehmer H. Nat Immunol (2005) 6:338-44; Shevach E M. Immunity (2009) 30:636-645; Miyara M. and Sakaguchi S. Trends Mol Med (2007) 13:108-16; Askenasy N. et al. Autoimmun Rev (2008) 7:370-5; Sojka D K et al. Immunology (2008) 124:13-22; Vignali et al. Nat Rev Immunol (2008) 8: 523-32].

The use of T regulatory cells has been previously implicated for the treatment of autoimmune diseases, these are summarized infra:

U.S. Patent Application No. 20100310588 (to Bluestone J. A. et al.) discloses methods for producing autoantigen-specific regulatory T cells and methods for use of same. According to the teachings of 20100310588, T cells are derived from a subject or from a donor, CD25+CD4+ T regulatory (Treg) cells are selected by immuno-selection and cell sorting, the Treg cells are expanded ex vivo by the use of a TCR/CD3 activator (e.g. anti-CD3 antibody), a TCR costimulator activator (e.g. anti-CD28 antibody) and IL-2 and the expanded population of Treg cells are adoptively transferred to a subject for treatment of autoimmune responses (e.g. diabetes, GVHD, Lupus, etc.).

U.S. Patent Application No. 20100260781 (to Murray L. A.) provides methods and compositions for expanding T regulatory cells ex vivo or in vivo using one or more serum amyloid P(SAP) agonists (e.g. SAP polypeptide). According to their teachings, the use of SAP agonists enriches for regulatory T cells and thus promotes regulatory T cell-mediated suppression of autoimmune disorders or conditions (e.g. diabetes, graft rejection, GVHD, etc.).

U.S. Patent Application No. 20100092488 (to Suzumura A. et al.) provides methods for increasing the number of regulatory T cells by inhibiting midkine (MK). 20100092488 further provides methods for treatment or prevention of diseases (e.g. autoimmune diseases such as diabetes, lupus etc.) associated with the functional disorder of regulatory T cells comprising the administration of a midkine inhibitor.

U.S. Patent Application No. 20090142308 (to Orban T. et al.) provides methods for treating autoimmune diseases (e.g. diabetes) by inducing autoantigen-specific regulatory CD4+ T cells. According to the teachings of 20090142308, treating an autoimmune disease is effected by first administering to the subject a composition comprising an autoantigen (e.g. insulin) and an oil-and-water adjuvant. Next, a blood sample comprising PBMCs is obtained from the subject and autoantigen-specific regulatory T cells are isolated therefrom. The autoantigen-specific regulatory T cells may then be expanded ex vivo to obtain an adequate amount of cells for treatment and the autoantigen-specific regulatory T cells are then administered back to a subject.

PCT Publication No. 2010/017220 (to Kambayashi T. et al.) discloses methods of expanding and enriching a regulatory T-cell population by contacting a leukocytes population having antigen-presenting cells with a granulocyte-macrophage colony stimulating factor (GMCSF), interleukin-3 (IL-3) and/or interleukin-5 (IL-5). The regulatory T cells disclosed therein may be used for suppressing naïve T-cells in a subject and subsequently for the treatment of autoimmune diseases.

In addition, depletion of autoreactive T cells through apoptosis as a means of preventing autoimmune diseases has also been contemplated. Jin et al. [Jin et al. Gene Therapy (2004) 11:982-991] disclosed the use of a CTLA4-Fas ligand (FasL) fusion protein, which simultaneously stimulates the Fas-mediated pathway and blocks co-stimulation of the T cell receptor, for apoptosis of peripheral T lymphocytes.

SUMMARY OF THE INVENTION

According to an aspect of some embodiments of the present invention there is provided an isolated immune regulatory cell having an exogenous cell death-inducing moiety attached to a surface thereof.

According to an aspect of some embodiments of the present invention there is provided an isolated population of cells.

According to an aspect of some embodiments of the present invention there is provided a molecule comprising a cell death-inducing moiety heterologously attached to an immune regulatory cell-specific binding moiety.

According to an aspect of some embodiments of the present invention there is provided a pharmaceutical composition comprising the isolated population of cells or the molecule and a pharmaceutically acceptable carrier or diluent.

According to an aspect of some embodiments of the present invention there is provided a method of generating the cell, the method comprising isolating an immune regulatory cell from a biological sample and expressing- or immobilizing on a surface of the immune regulatory cell a cell-death inducing moiety, thereby generating the cell.

According to an aspect of some embodiments of the present invention there is provided a use of the isolated population of cells or the molecule for the manufacture of a medicament identified for treating a medical condition in which suppression of immune effector cells is therapeutically beneficial.

According to an aspect of some embodiments of the present invention there is provided a method of treating a medical condition in which suppression of immune effector cells is therapeutically beneficial in a subject in need thereof, the method comprising administering to the subject a therapeutically effective amount of the isolated population of cells or the molecule, thereby treating the medical condition.

According to an aspect of some embodiments of the present invention there is provided a method of killing immune effector cells, the method comprising contacting the immune effector cells with the isolated population of cells, thereby killing immune effector cells.

According to an aspect of some embodiments of the present invention there is provided a kit for treating a medical condition in which suppression of immune effector cells is therapeutically beneficial, the kit comprising the isolated population of cells or the molecule and an immunosuppressive agent.

According to some embodiments of the invention, the molecule is isolated.

According to some embodiments of the invention, the method further comprises stimulating the cell prior to, concomitantly with, or following the expressing- or immobilizing a cell-death inducing moiety on the cell.

According to some embodiments of the invention, the cell death-inducing moiety comprises an apoptosis-inducing molecule.

According to some embodiments of the invention, the cell death-inducing moiety comprises a toxic molecule.

According to some embodiments of the invention, the cell death-inducing moiety is an extracellular cell death inducing moiety.

According to some embodiments of the invention, the cell death-inducing moiety is an intracellular cell death inducing moiety.

According to some embodiments of the invention, the cell death-inducing moiety is selected from the group consisting of a toxin, a polypeptide, a lectin or a combination of same.

According to some embodiments of the invention, the apoptosis-inducing molecule is selected from the group consisting of TNF-α, Fas-ligand, TRAIL and Tweak.

According to some embodiments of the invention, the apoptosis-inducing molecule comprises Fas-ligand.

According to some embodiments of the invention, the isolated population of cells or molecule are for treating an inflammatory disease, an autoimmune disease, a cancer, a hypersensitivity and a transplant-related disease.

According to some embodiments of the invention, the therapeutically effective amount is for killing the immune effector cells.

According to some embodiments of the invention, the immune regulatory cell comprises a suppressive activity.

According to some embodiments of the invention, the immune regulatory cell is selected from the group consisting of a T cell, a B cell, a myeloid cell, a natural killer cell and an antigen-presenting cell.

According to some embodiments of the invention, the immune regulatory cell comprises a T regulatory cell.

According to some embodiments of the invention, the T regulatory cell comprise a CD4+CD25+ cell signature.

According to some embodiments of the invention, the immune effector cells are selected from the group consisting of effector T cells, effector B cells, effector myeloid cells, effector natural killer cells and effector antigen-presenting cells.

According to some embodiments of the invention, the immune effector cells comprise effector T cells.

According to some embodiments of the invention, the medical condition is selected from the group consisting of an inflammatory disease, an autoimmune disease, a cancer, a hypersensitivity and a transplant-related disease.

According to some embodiments of the invention, the autoimmune disease is selected from the group consisting of diabetes mellitus type I, diabetes mellitus type II, systemic lupus erythematosis, multiple sclerosis, myasthenia gravis, progressive systemic sclerosis, hyperimmunoglobin E, Hashimoto's thyroiditis, familial Mediterranean fever, Grave's disease, autoimmune haemolytic anemia and primary biliary cirrhosis.

According to some embodiments of the invention, the autoimmune disease is diabetes mellitus type I or type II.

According to some embodiments of the invention, the inflammatory disease is selected from the group consisting of inflammatory bowel disease (IBD), Crohn's disease, ulcerative colitis, rheumatoid arthritis, rheumatoid spondylitis, osteoarthritis, gouty arthritis, arthritic conditions, inflamed joints, eczema, inflammatory skin conditions, inflammatory eye conditions, conjunctivitis, pyresis, tissue necrosis resulting from inflammation, atopic dermatitis, hepatitis B antigen negative chronic active hepatitis, airway inflammation, asthma and bronchitis.

According to some embodiments of the invention, the inflammatory disease is inflammatory bowel disease (IBD).

According to some embodiments of the invention, the transplant-related disease is graft versus host disease (GVHD).

According to some embodiments of the invention, the transplant-related disease is graft rejection.

According to some embodiments of the invention, the biological sample is syngeneic with the subject.

According to some embodiments of the invention, the biological sample is allogeneic with the subject.

According to some embodiments of the invention, the biological sample comprises a blood sample.

According to some embodiments of the invention, the immunosuppressive agent is selected from the group consisting of steroids, rapamycin, fludarabine, methotrexate, cyclophosphamide, cyclosporine, cyclosporin A, chloroquine, hydroxychloroquine, sulfasalazine (sulphasalazopyrine), gold salts, D-penicillamine, leflunomide, azathioprine, anakinra, infliximab, etanercept, TNF alpha blockers, a biological agent that targets an inflammatory cytokine and Non-Steroidal Anti-Inflammatory Drug (NSAIDs).

According to some embodiments of the invention, the immune regulatory cell-specific binding moiety is selected from the group consisting of an antibody and a ligand.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1A is a graph illustrating incidence of spontaneous diabetes in the female (n=312) and male (n=126) NOD colony; FIG. 1B is a graph illustrating distribution of $CD25^+FoxP3^+$ and $CD25^+CD62L^+$ Treg in mesenteric (MLN) and pancreatic lymph nodes (PLN) of NOD females as a function of age and after onset of overt hyperglycemia (n=4-7 at each time point); FIGS. 1C-D are graphs illustrating fractional distribution of CD25 and FoxP3 in regional lymph nodes in advanced stages of insulitis (n=8, ages 14-16 weeks) and new onset diabetic female NOD mice (n=6) in the mesenteric (FIG. 1C) and pancreatic lymph nodes (FIG. 1D); FIG. 1E is a graph illustrating distribution of $CD25^+FoxP3^+$ and $CD25^+CD62L^+$ Treg in pancreatic infiltrates of NOD females as a function of age and after onset of overt hyperglycemia (n=4-7 at each time point); and FIG. 1F is a graph illustrating fractional distribution of CD25 and FoxP3 in pancreatic infiltrates in advanced stages of insulitis (n=5) and after onset of overt diabetes in NOD females (n=5).

FIGS. 2A-H depict the effect of soluble and cellular factors on susceptibility of isolated Treg to apoptosis. FIG. 2A-E are dot plot analysis illustrating apoptosis of $CD4^+CD25^-$ and $CD4^+CD25^+$ subsets measured after 48 hours in isolated cell suspensions (n=5) and by gating in mixed cultures (n=5). Cells were harvested from wild type C57BL/6, prediabetic NOD females aged 14 weeks and new onset diabetic NOD mice. Representative measurements of 7-AAD (death) and Annexin-V (apoptosis) incorporation are shown for isolated and mixed populations (gated) from diabetic NOD females [adapted from Kaminitz A. et al. PLoS One (2010) 31; 5:e15684]; FIGS. 2F-G are graphs illustrating apoptosis and proliferation rates, respectively. Isolated $CD25^+$ T cells from new onset diabetic NOD females were incubated in medium (control) and with 2000 U/ml IL-2 for 48 hours (n=4) for determination of apoptosis (Annexin-V incorporation) and proliferation rates (measured from CFSE dilution using the ModFit software) [adapted from Kaminitz A. et al, supra]; FIG. 2H is a graph illustrating apoptosis rates. Sorted $CD4^+FoxP3^+$ Treg cells from transgenic mice expressing GFP under control of the FoxP3 promoter were submitted to CD3 and CD3/CD28 stimulation for 48 hours, showing marked reduction in fractional apoptosis (n=3).

FIGS. 3A-P depict Treg sensitivity to apoptosis in mixed cultures. FIGS. 3A-E are graphs illustrating apoptosis. Treg were gated in mixed cultures of splenocytes and lymph nodes according to CD25 expression in prediabetic (12-16 weeks old) NOD females (n=5) and B6 mice (wild type, n=7), and on GFP in B6 transgenes expressing the reporter protein under control of the foxP3 promoter (n=5). Apoptosis was determined from Annexin-V incorporation after 48 hours of culture in medium and with 50 μg/ml FasL [adapted from Kaminitz A, PLOS One (2011) in press]; FIG. 3H-M are graphs illustrating results of FACS analysis. Immunomagnetic isolation of T cell subsets according to CD25 expression results in a $CD25^-$ subset with little contamination that expresses FoxP3 at low levels and a $CD25^+$ subset co-expressing FoxP3. Flow cytometry images are representative of 19 isolation procedures; FIGS. 3N-P are graphs illustrating inhibition of proliferation of CFSE-labeled $CD25^-$ T cell responders activated with CD3/CD28 (control) by $CD25^+$ T cells isolated from NOD and wild type mice after incubation with FasL at a Teff:Treg ratio of 3:1. Data are representative of four experiments in which $CD25^+$ suppressor cells were co-incubated with CFSE-labeled $CD25^-$ responders from the same strain (n=3-4) [157].

FIG. 4A is a graph illustrating the efficiency of disease transfer. Disease transfer was similar after adoptive transfer into NOD SCID mice of $2.5 \times 10^7$ $CD4^+CD25^-$ T cells from new onset diabetic (n=6) or from prediabetic NOD mice (insulitis, n=36) aged 12-16 weeks. The disease was not transferred by $2.5-8 \times 10^6$ $CD4^+CD25^+$ T cells (n=14); FIG. 4B is a graph illustrating NOD SCID mice reconstituted with $CD25^-$ T cells from diabetic NOD donors present consistent decreased fractions of $CD25^+FoxP3^+$ Treg in the lymph nodes as compared to recipients of cells from prediabetic NOD donors (n=6-7); FIGS. 4C-D are graphs illustrating immune profiling of CD4+ T cells in mesenteric/pancreatic lymph nodes of NOD SCID mice reconstituted with $CD25^-$ that developed (diabetic, n=5) and did not display overt hyperglycemia (healthy, n=7) and non-diabetic recipients of $CD25^+$ T cells (n=7) from prediabetic (FIG. 4C) and new onset diabetic NOD females (FIG. 4D); FIG. 4E is a graph illustrating incidence of diabetes in NOD SCID mice after co-adoptive transfer of $2.5 \times 10^7$ $CD4^+CD25^-$ T cells, and $2.5 \times 10^6$ $CD4^+CD25^+$ T cells (n=10) as compared to $2.5 \times 10^7$ $CD4^+CD25^-$ T cells alone (n=36); FIG. 4F is a graph illustrating fractional expression of CD25, FoxP3 and their combination in pancreatic inflammatory infiltrates of diabetic NOD.SCID mice after adoptive transfer of CD25⁻ and CD25⁺ (10:1 ratio) from prediabetic (insulitis, n=8) and new onset diabetic NOD females (diabetes, n=5).

FIGS. 5A-H depict that naïve/effector and diabetogenic T cells in NOD mice are submitted to Fas-mediated negative regulation. FIG. 5A is a graph illustrating the incidence of diabetes after adoptive transfer and the composition of cell inoculum (left side). Splenocytes from prediabetic NOD females (14 weeks) were incubated for 48 hours in medium (n=6) and with 50 µg/ml FasL (n=8) before adoptive transfer of $2.5 \times 10^7$ viable splenocytes into NOD SCID mice; FIG. 5B is a graph illustrating diabetic rates. CD25⁻ T cells isolated from prediabetic NOD females (14 weeks) were coated with FasL protein before infusion into NOD SCID mice (n=10), as compared to control infusion of $2.5 \times 10^7$ naïve CD25⁻ T cells (n=36); FIG. 5C is a graph illustrating apoptosis rated. CD4⁺CD25⁻ T cells were gated in mixed cultures of splenocytes and lymph nodes from prediabetic (12-16 weeks old) NOD females (n=5) and B6 mice (wild type, n=7), and on GFP in B6 transgenes expressing the reporter protein under control of the foxP3 promoter (n=5). Apoptosis was determined from Annexin-V incorporation after 48 hours of culture in medium and with 50 µg/ml FasL; FIG. 5D-G illustrated FACS analysis. Isolated CD25⁻ T cells from wild type and NOD mice convert to express CD25 without FoxP3 priming during 48 hours of CD3/CD28 stimulation. Consistently, GFP expression in B6 transgenes expressing the reporter protein under control of the FoxP3 promoter display stable expression under Cd3/CD28 stimulation; FIG. 5H is a graph illustrating apoptosis of CD4⁺FoxP3⁻ T cells from FoxP3-GFP under stimulation with CD3 and CD3/CD28 incubated in medium (n=5) and with 50 µg/ml FasL (n=6) for 48 hours.

FIGS. 6A-G depict that FasL enhances Treg cell-mediated suppression in vitro [adapted from Kaminitz A. et al., J Autoimmun (2011) 37:39-47]. Isolated CD4⁺CD25⁻ responders labeled with CFSE were stimulated with CD3/CD28 immobilized on beads (at a ratio 1:1) for 48 hours. CD4⁺CD25⁺ T cells were added at various ratios with and without overexpression of FasL on their surface via biotinylation. FIG. 6A is a graph illustrating proliferation index in responders at various ratios of co-incubated Treg; FIGS. 6B-D are representative plots that present analysis of CFSE dilution in gated responders using the ModFit software; FIG. 6E is a graph illustrating apoptosis of CD25⁻ T cells incubated with naïve and FasL-coated CD25⁺ T cells at various ratios; FIGS. 6F-G are representative plots of apoptosis, as determined from Annexin-V incorporation, and are presented for gated CFSE-labeled CD25⁻ responders co-incubated with naïve (CD25⁺) and FasL-coated (FasL) CD25⁺ T cells at Treg:Teff ratio of 1:5.

FIGS. 7A-G depict that killer Treg modulate the activity of diabetogenic cells in NOD SCID mice [adapted from Kaminitz A. et al., J Autoimmun (2011) 37:39-47]. FIG. 7A is a graph illustrating incidence of diabetes in NOD SCID mice after co-adoptive transfer of $2.5 \times 10^7$ CD4⁺CD25⁻ T cells and $2.5 \times 10^6$ CD4⁺CD25⁺ T cells with (n=10) and without decoration with FasL protein via biotinylation (n=10); FIG. 7B is a graph illustrating inflammatory score in diabetic recipients of naïve (CD25⁺, n=38 islets) and FasL-coated Treg (CD25⁺FasL) that became diabetic (n=29 islets) and sustained normoglycemia (n=54 islets), accompanied by representative brightfield images (FIGS. 7C-D); FIG. 7E is a graph illustrating CD4⁺CD25⁺FoxP3⁺ T cells in peripheral lymphoid organs of mice that developed diabetes after infusion of naïve (n=5) and FasL-coated CD25⁺ T cells (n=2), and normoglycemic mice (non-diabetic, n=5); FIG. 7F is a graph illustrating fractional expression of CD25, FoxP3 and their combination in the pancreatic inflammatory infiltrates of the corresponding groups of adoptively transferred NOD SCID mice; and FIG. 7G is a graph illustrating fractional CD25 and FoxP3 expression within the CD4⁺ subset in the thymus.

FIG. 8A is a graph illustrating incidence of diabetes after infusion of $3\text{-}4 \times 10^6$ FasL-coated splenocytes (n=11), naïve (n=9) and FasL-coated (n=10) CD4⁺CD25⁺ T cells into 14 weeks old NOD females; FIGS. 8C-F are flow cytometric analysis of the pancreatic infiltrates after adoptive transfer of CFSE-labeled naïve and FasL-coated CD25⁺ T cells detected by staining for FoxP3. Pancreas-homed cells proliferate in situ, as demonstrated by CFSE dilution in the gated FoxP3 cells; FIGS. 8G-J are flow cytometric analysis illustrating detection of apoptotic cells in reference to CD25 expression in the pancreatic lymph nodes of naïve NOD mice (naïve) and recipients of naïve Treg (CD25⁺) and FasL-coated Treg (CD25⁺FasL); FIG. 8O is a photograph of a demonstrative H&E section showing infiltration from the vascular pedicle (lower and upper islets) and a non-inflamed islet (middle);

FIGS. 9A-G depict that FasL-coated CD25⁺ T cells modulate the course of established disease. FIG. 9A is a graph illustrating blood glucose levels exceeding 200 mg/dl in NOD females with spontaneous diabetes (n=23) and after administration (time 0) of $3\text{–}4 \times 10^6$ FasL-coated CD25⁺ T cells (n=7). Arrows: increase in blood glucose to levels exceeding 550 mg/dl in the treated mice; FIG. 9B is a graph illustrating fasting serum insulin three weeks after onset of spontaneous diabetes in untreated (n=5) and immunomodulated mice (n=4); FIGS. 9C-D are graphs illustrating immune profiles of mesenteric/pancreatic lymph nodes (FIG. 9C) and thymus (FIG. 9D) in spontaneously diabetic NOD females (n=6) and mice infused with FasL-coated CD25⁺ T cells (n=3-4); FIG. 9E is a graph illustrating fractional expression of CD25 and FoxP3 in pancreata of NOD females at 6 weeks after onset of spontaneous diabetes (n=6) and after infusion of FasL-coated CD25⁺ T cells (n=4); and FIGS. 9F-G are photographs illustrating detection of CD4⁺FoxP3⁺ Treg by immunohistochemistry in pancreata of spontaneously diabetic mice (FIG. 9F) and after infusion of FasL-coated CD25+ T cells (FIG. 9G, scale bar 40 μm).

FIG. 10A is a graph illustrating the incidence of diabetes in female NOD mice aged 14 weeks sublethally radiated (650 rad, n=14) and infused with $3 \times 10^6$ CD25+ T cells from age matched donors (n=14, rad CD25+) [adapted from Kaminitz A. et al., J Autoimmun (2010) 35:145-52]; FIG. 10B is a graph illustrating the incidence of diabetes in NOD females immunomodulated at the age of 14 weeks with FasL-coated CD25+ T cells from age matched donors with (n=7) and without (n=10) sublethal irradiation; FIG. 10C is a graph illustrating fractional distribution of CD25 and FoxP3 in mesenteric/pancreatic lymph nodes of irradiated (n=5) and non-irradiated NOD females adoptively transferred with killer Treg (3 diabetic and 5 non-diabetic); and FIG. 10D is a graph illustrating fractional distribution of CD25 and FoxP3 in pancreatic infiltrates of the corresponding experimental groups.

FIGS. 11A-B illustrate the disease activity score integrated for several parameters related to intestinal function in healthy (n=10), sick (n=7), and recipients of Cd25+ T cells with (n=7) and without (n=6) FasL protein; FIG. 11C is a graph illustrating changes in body weight; FIG. 11D is a graph illustrating colon length on day 8 after onset of DSS administration; FIG. 11E is a graph illustrating fractional expression of CD62L in CD4+ T cells from mesenteric lymph nodes of sick and treated mice; and FIG. 11F is a graph illustrating fractional distribution of CD25 and FoxP3 in CD4+ T cells from mesenteric lymph nodes.

FIGS. 12A-F depict modulation of graft versus host disease using killer Treg cells. Sublethally irradiated (700 rad) F1 recipients (H2K$^{b/d}$) were grafted with $5 \times 10^6$ T cell depleted bone marrow cells and $2 \times 10^7$ viable splenocytes from parent (H2K$^b$) donors (GVHD). Mice received $4 \times 10^6$ CD25+ T cells with and without FasL protein. FIG. 12A is a graph illustrating outcome of the lethal GVHD model in the experimental groups (n=10); FIG. 12B is a graph illustrating seven days after transplantation, mice were challenged with 10 μg LPS (n=10 in each group), which precipitates death in mice with ongoing GVHD; FIG. 12C is a graph illustrating histological score of ear wedge and liver biopsies according to: 0—no infiltration, 1—scarce infiltrates, 2—patchy infiltration, 3—diffuse infiltration, 4—deterioration of tissue structure; FIG. 12D is a graph illustrating weight loss in recipients of naïve and FasL-coated CD25+ T cells; and FIGS. 12E-F are graphs illustrating immunophenotype of the spleens (FIG. 12E) and mesenteric lymph nodes (FIG. 12F) at 3 weeks after transplantation: fractional distribution of CD25 and FoxP3.

FIGS. 13A-B depict the impact of killer Treg on graft acceptance with simultaneous BMT. Neonatal heart grafts were implanted into the ear pinna of allogeneic mice (H2K$^b$→H2K$^d$) and graft survival was assessed by contractile function. Bone marrow transplantation was performed by infusion of $5 \times 10^6$ bone marrow cells into recipients irradiated at 850 rad; FIG. 13A is a graph illustrating implantation of heart grafts without BMT (n=10), 2 weeks after BMT (n=9) and with simultaneous BMT (n=7); and FIG. 13B is a graph illustrating recipients of simultaneous heart and BMT grafts which were infused on day +2 with $4 \times 10^6$ naïve (n=6) and FasL-coated (n=7) CD25+ T cells.

DESCRIPTION OF SPECIFIC EMBODIMENTS OF THE INVENTION

Figure 1B:
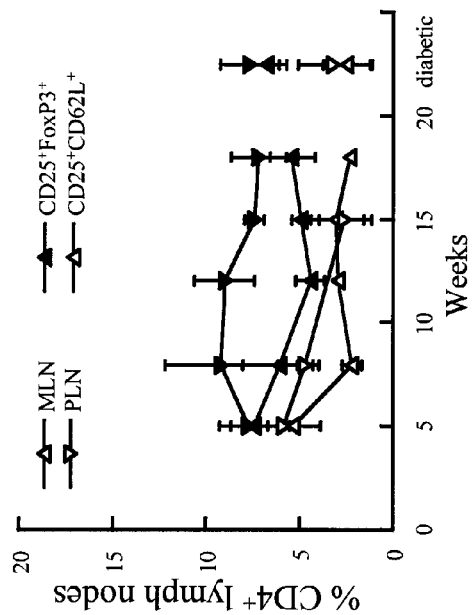
FIGS. 1A-F depict age related variations of Treg in non-obese diabetic (NOD) mice.

The present invention, in some embodiments thereof, relates to regulatory immune cells with enhanced apoptotic activity and, more particularly, but not exclusively, to the use thereof for immunomodulation, for treating or for preventing immune related disorders.

The principles and operation of the present invention may be better understood with reference to the drawings and accompanying descriptions.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Deficiency or dysfunction of regulatory immune cells has been implicated in the pathogenesis of several diseases (e.g. autoimmune diseases, inflammatory diseases) and, thus, immunotherapy is a highly desired treatment of such diseases. The use of T regulatory cells has been previously implicated for the treatment of autoimmune diseases.

The expression of death receptors (e.g. Fas receptor) is upregulated on activated immune cells (e.g. effector T cells) thus sensitizing these cells to activation induced cell death (AICD). Depletion of autoreactive T cells through apoptosis as a means of preventing autoimmune diseases has been previously contemplated. For instance, Jin et al. disclosed the use of a CTLA4-Fas ligand (FasL) fusion protein, which simultaneously stimulates the Fas-mediated pathway and blocks co-stimulation of the T cell receptor, for apoptosis of peripheral T cells [Jin et al. Gene Therapy (2004) 11:982-991].

While reducing the present invention to practice, the present inventors have realized that T regulatory cells can be improved and even modified towards naturally non existing functionalities by expressing death-inducing molecules (e.g. FasL). Due to their ability to home to the site of inflammation, the modified regulatory cells can cause death of effector T cells in an antigen specific manner. Interestingly, since stimulated effector T cells found in the site of inflammation express higher levels of death molecules (e.g. Fas receptor) they are sensitized to killing by the modified regulatory T cells and therefore lower amounts of regulatory cells are required. These findings place the cells of the present invention as a pivotal tool in the treatment of immune-related diseases and infer of other modes of therapy which are further described hereinbelow.

As is illustrated hereinbelow and in the Examples section which follows, the present inventors have generated regulatory T cells (Tregs) with enhanced cell death effect by chemically attaching to the surface of these cells a chimeric Fas-ligand (FasL) protein (see Materials and methods section and Example 6, hereinbelow). The present inventors have demonstrated that overexpression of FasL in Treg cells suppressed and induced apoptosis of CD4+CD25− T regulatory cells of non-obese diabetic (NOD) mice in vitro (see FIG. 6), lowered the efficacy of adoptive transfer of diabetes into NOD SCID mice (see FIG. 7) and postponed diabetes onset while reducing significantly its incidence in prediabetic NOD mice (see FIG. 8). Furthermore, FasL-overexpressing Tregs postponed evolution of the disease after onset of overt hyperglycemia (see FIG. 9). The present inventors have also illustrated that administration of FasL-overexpressing Tregs diminished inflammatory infiltrates at the experimental end point (see FIGS. 7,8) and increased serum insulin levels (see FIG. 9), as expected of physical elimination of the pathogenic cells and upregulation of suppressor mechanisms. Thus, the present results support the use of FasL overexpressing Tregs for suppression of diabetogenic effector cells at the site of inflammation and for diabetes treatment.

Moreover, the present inventors have illustrated the efficiency of modified FasL-overexpressing Tregs in ameliorating the course of DSS-induced colitis, a chronic colitis animal model. Overexpression of FasL on Tregs was superior to naïve Tregs in reducing disease activity score, reducing the frequency of effector cells and increasing the fraction of naturally occurring Treg in the mesenteric lymph nodes (see FIG. 11).

Additionally, the present inventors have substantiated the use of FasL-overexpressing Tregs in alleviation of graft versus host disease (GVHD) and transplant rejection. The present inventors utilized a murine haploidentical model of lethal GVHD and demonstrated that FasL-coated Treg cells have superior preventive efficacy as compared to naïve donor Tregs (see FIG. 12) as demonstrated by superior survival and rescue of 70% of LPS-induced lethal GVHD, improved histological score and amelioration of weight loss. Furthermore, early infusion of FasL-overexpressing Tregs after simultaneous transplants of bone marrow cells and neonatal heart allografts improved survival of the allografts, indicating decreased responsiveness to donor antigens (see FIG. 13).

Taken together, these results substantiate the value of modified Treg cells overexpressing a death molecule, such as FasL, for treatment of immune related diseases.

Thus according to an aspect of the invention there is provided a method of killing immune effector cells, the method comprising contacting the immune effector cells with immune regulatory cells having an exogenous cell death-inducing moiety attached to the surface thereof.

Such a method can be harnessed to clinical conditions in which activated immune cells cause inflammation or disease (e.g. inflammatory disease, autoimmune disease).

Thus, according to one aspect of the present invention there is provided a method of treating a medical condition in which suppression of immune effector cells is therapeutically beneficial in a subject in need thereof.

The method may be effected ex vivo by administering to the subject a therapeutically effective amount of isolated immune regulatory cells having an exogenous cell death-inducing moiety attached to a surface thereof.

As used herein the term "ex vivo" refers to a process in which cells, which are removed from a living organism, are cultured outside the organism (e.g., in a cell culture plate, flask, bag or test tube).

As used herein the term "isolated" refers to at least partially separated from the natural environment e.g., the human body.

As used herein the term "immune regulatory cells" refers to a specialized subpopulation of cells that act to downregulate activation of the immune system (e.g. downregulate reactive immune cells), maintain immune system homeostasis and/or tolerance to self-antigens. The immune regulatory cells typically also suppress autoimmune reactions.

According to an embodiment, the immune regulatory cells comprise a suppressive activity. Methods of measuring suppression are described in further detail hereinbelow.

According to an embodiment, the immune regulatory cells comprise T cells, B cells, myeloid cells, natural killer cells or antigen-presenting cells.

Regulatory T cells (Tregs) of the present invention refer to the subset of T cells which actively suppress or tolerize activation of the immune system (e.g. reactive immune cells), maintain immune system homeostasis and/or prevent pathological self-reactivity. Regulatory T cells of the present invention include cells that express e.g. CD8 and CD122, or CD4, CD25, Foxp3, CD45RB$^{low}$, CD62L$^{high}$ and/or TCD$^{\alpha\beta}$ (e.g. naturally occurring CD4$^+$CD25$^+$FoxP3$^+$ regulatory T cells). However, the term T regulatory cells also encompass other T cells that have suppressive function. The regulatory T cells of the present invention encompass both "naturally-occurring" Tregs as well as Tregs generated in vitro.

Tregs of the present invention are typically capable of suppressing a variety of cells, such as other T cells (e.g. effector T cells), B cells (e.g. effector B cells) and/or antigen presenting cells (e.g. effector APCs such as monocytes and dendritic cells). Typically Tregs exert their function via TCR/MHC class II interaction following cell to cell contact, however, Tregs may also suppress effector cells by secretion of immunosuppressive cytokines (e.g. TGF-beta and IL-10).

Regulatory B cells of the present invention refer to the subset of B cells which actively suppress activation of the immune system (e.g. reactive immune cells) and maintain immune system homeostasis. Regulatory B cells of the present invention include cells that express CD19, CD20, CD21, CD23, CD5, CD1d and/or Foxp3. The regulatory B cells of the present invention encompass both "naturally occurring" regulatory B cells and regulatory B cells generated in vitro.

B regulatory cells of the present invention are typically capable of suppressing a variety of cells, such as other B cells (e.g. effector B cells), T cells (e.g. effector T cells such as CD4+ T cells) and/or antigen presenting cells (e.g. effector APCs). The suppressive activity of B regulatory cells is typically carried out by secretion of immunosuppressive cytokines (e.g. IL-10, IL-17 and TGF-β).

Regulatory natural killer (NK) cells of the present invention refer to the subset of non-cytolytic NKT cells displaying immuno-regulatory functions. The regulatory NK cells of the present invention may express immunosuppressive molecules (e.g. HLA-G) and may secrete immunosuppressive cytokines (e.g. IL-10 and IL-21).

Regulatory NK cells of the present invention are typically capable of suppressing a variety of cells, such as APCs [e.g. dendritic cells such as by reconverting mature myeloid DC (mDC) into immature/tolerogenic DC] and other NK cells (e.g. by blocking cytolytic functions). The regulatory NK cells of the present invention encompass both "naturally occurring" regulatory NK cells and regulatory NK cells generated in vitro.

Regulatory myeloid cells of the present invention refer to the leukocyte subset of cells that are not lymphocytes (e.g. T or B lymphocytes). These cells present polymorphonuclear granulocyte phenotypes, and typically include cells that express CD14, CD33, CD11b, CD43 and/or CD86. Regulatory myeloid cells of the present invention typically comprise high levels of arginase, inducible nitric oxide synthase and/or peroxynitrites. The regulatory myeloid cells of the present invention encompass both "naturally occurring" regulatory myeloid cells and regulatory myeloid cells generated in vitro.

Regulatory antigen-presenting cells (APCs) of the present invention refer to the subset of APCs which are capable of downregulating an immune response system (e.g. reactive immune cells). Regulatory APCs of the present invention may include, for example, dendritic cells (DCs), macrophages, fibroblasts, glial cells, pancreatic beta cells and vascular endothelial cells. The regulatory APCs of the present invention encompass both "naturally occurring" regulatory APCs and regulatory APCs generated in vitro.

According to one embodiment, the regulatory APCs are regulatory dendritic cells. Thus, for example, regulatory DCs (e.g. Foxp3+ DCs) are capable of specifically inhibiting proliferation and Type 1 immune responses of naïve T cells.

According to a specific embodiment, the immune regulatory cell comprises a T regulatory cell (Treg).

Methods of measuring immune suppression are described in further detail hereinbelow.

Regulatory immune cells may be isolated, generated or expanded by any method known to one of ordinary skill in the art [see e.g. Levings M K et al., J Exp Med (2001)193: 1295-302; Tang Q et al., J Exp Med (2004) 199:1455-65; Tarbell K V et al., J Exp Med (2004)199:1467-77; Kretschmer K et al., Nat Immunol (2005) 6:1219-27].

According to one embodiment, the immune regulatory cells are isolated from a biological sample.

As used herein, the phrase "biological sample" refers to any sample that contains regulatory immune cells (e.g. regulatory T cells, regulatory B cells, etc.). The biological sample of the present invention may include a blood sample, a biopsy specimen, a biological fluid or any other tissue or cell preparation, including for example, an isolated cell population, fresh whole blood, fractionated whole blood, bone marrow, spinal fluid and/or cord blood. The cell population may be a primary cell culture or a culture adapted cell line including, but not limited to, a genetically engineered cell line, an immortalized or an immortalizable cell line, a differentiated or a differentiatable cell line, a transformed cell line and the like.

According to a specific embodiment, the biological sample is a blood sample.

According to another embodiment, the biological sample is syngeneic with the subject (i.e. from the subject).

According to another embodiment, the biological sample is non-syngeneic (e.g. allogeneic) with the subject.

The biological sample may be obtained by any method known to one of ordinary skill in the art, as for example, by a needle puncture. In cases where a cell population is used, the cells may be obtained from the subject or from a cell donor (e.g. syngeneic or non-syngeneic donor) by, for example, blood apheresis.

Any method of cell isolation may be used according to the present teachings. One exemplary method of isolation of regulatory cells from peripheral blood comprises centrifugation, with or without a gradient (e.g. Percoll gradient). This technique separates cells based upon density. Another exemplary method which may be used comprises panning and immunomagnetic isolation, using molecules immobilized to surface or magnetic beads, respectively, as for example, antibodies that recognize and bind molecules on the cell surface (e.g. CD4, CD8, CD20, etc.). Molecules immobilized to a surface or conjugated to magnetic beads recognize and bind to one or more of the cell specific surface markers of a particular cell type. Cells that possess one or more cell surface markers are bound by the immobilized molecules or exposure of the bead-conjugated cells to a magnetic field, allowing any other cell to be washed away. In positive selection procedures the cell type of interest is retained, and in negative selection procedures cell type of interest is purged. Another isolation procedure which may used according to the present teachings includes fluorescence activated cell sorting (FACS). Antibodies with fluorescent tags may be used to bind to the cells of interest. The antibodies bind to the cell surface molecules (e.g. CD4, CD8, CD20, etc.), and a FACS sorter may then sort and collect the cells based upon the fluorescence observed. The cells that display certain fluorescence may then be isolated.

Following isolation of the immune regulatory cells, the cells may be further cultured, expanded and/or stimulated.

Ex vivo expansion of isolated immune regulatory cells include, for example, the protocol for T regulatory cells: cells are cultured with CD3/CD28 stimulation (e.g. anti-CD3 antibody and anti-CD28 antibody) in the presence of high IL-2 concentrations, IL-10 and stimulation/education with dendritic cells. Ex vivo expansion of the cells as described herein (i.e. with an antigen presenting cell) may also selectively enrich for antigen-specific immune regulatory cells.

It will be appreciated that the immune regulatory cells may also be expanded in vivo in order to increase the number of these cells prior to isolation and ex vivo manipulation.

One immunomodulatory approach which can be used to increase in vivo the number of immune regulatory cells (e.g. Tregs) comprise a combination treatment with anti-thymocyte globulin, Freund's adjuvant, vasoactive intestinal peptide, dipeptidyl peptidase IV, exendin-4 and rapamycin.

As is shown in the Examples section which follows (see e.g. Example 6), the present inventors have shown that overexpression of a death molecule (e.g. Fas-Ligand) on immune regulatory cells (e.g. Tregs) directs antigen specific killing of effector cells (T effector cells).

Thus, according to the present teachings, an exogenous cell death-inducing moiety is attached to the surface of the immune regulatory cells.

As used herein, the phrase "exogenous cell death-inducing moiety" refers to an agent (e.g. chemical or polypeptide) capable of promoting cell necrosis or programmed cell death of cells. Preferably, the cell death inducing moiety does not affect the regulatory cells. The cell death-inducing moiety may not be typically expressed by the cell. Alternatively, in situations where the cell death-inducing moiety is expressed by the cell, the present invention contemplates overexpressing same as compared to a non-modified cell of the same species.

According to a specific embodiment, the cell death-inducing moiety comprises a toxin, a polypeptide, a lectin or a combination of same.

According to a specific embodiment, the cell death-inducing moiety comprises a polypeptide.

According to an embodiment, the cell death-inducing moiety is an extracellular cell death inducing moiety.

The phrase "extracellular cell death-inducing moiety" refers to a cell-death inducing moiety which exerts its action (i.e., cell death) via interaction with a molecule (e.g. receptor) on the outside surface of a target cell (e.g. effector cell, cancer cell) or by induction of pores within the cell membranes, through which the cell death-inducing moiety can enter the cell. Following such an interaction, an intracellular cascade of reactions is typically initiated which results in cell death.

Thus, for example, Fas-Ligand (FasL) expressed on the immune regulatory cell is capable of specifically binding to Fas-Receptor (FasR) on the target effector cell and initiating a signal transduction cascade. This cascade usually comprises activation of a series of caspases, which then results in the cleavage of a series of vital cellular proteins and ultimately to cell death.

According to another embodiment, the cell death-inducing moiety is an intracellular cell death inducing moiety.

The phrase "intracellular cell death inducing moiety" refers to an agent which exerts its action (i.e., cell death) within a target cell (e.g. effector cell, cancer cell). Such an agent is typically taken up by the target cell (e.g. via endocytosis) and consequently induces cell death from within the target cell. Such agents include toxins, as further detailed hereinbelow.

According to one embodiment, the cell death-inducing moiety comprises an apoptosis-inducing molecule.

As used herein, the phrase "apoptosis-inducing molecule" refers to an agent (e.g. chemical or polypeptide) capable of transmitting apoptotic or necrotic signals to a cell (e.g. effector cell). Such molecules typically cause cell death upon direct contact with the target cell (e.g. extracellular cell death inducing moiety).

It will be appreciated that the apoptosis-inducing molecules of the present invention efficiently target and eliminate activated immune cells (e.g. effector cells) as these cells are intrinsically sensitive to apoptosis (e.g. express cell surface death receptors).

According to one embodiment, the apoptosis-inducing molecule comprises a molecule belonging to the tumor necrosis factor (TNF) superfamily.

Exemplary apoptosis-inducing molecules that may be used in accordance with the present invention include, but are not limited to TNF-α, FasL, TRAIL (Apo2 ligand) and Tweak (Apo3 ligand). Such apoptosis-inducing molecules may be recombinant polypeptides, biochemically synthesized or purified from cell extracts. Recombinant TNF-α, FasL, Trail and Tweak are all commercially available from Companies such as R&D Systems (Minneapolis, Minn.) and Abnova Corporation (Taiwan). Those skilled in the art are aware that many pharmaceutical agents exist that enhance apoptosis. Among such agents are bis-indolylmaleimide-8 and quabain. If desired, these agents may be used in conjunction with the apoptosis-inducing molecules of this invention.

According to a specific embodiment of this aspect of the present invention, the apoptosis-inducing molecule used is FasL. The FasL of the present invention preferably comprises the extracellular domain of FasL.

As used herein, the term FasL refers to at least an active portion of a FasL polypeptide capable of binding the Fas receptor and inducing apoptosis. Preferably the FasL is mammalian, for example human. An exemplary polypeptide sequence of human FasL is set forth in GenBank AAC50124. Thus, according to this aspect of the present invention, the FasL may be a biologically active peptide derivative of the Fas ligand polypeptide, a biologically active peptoid derived from Fas ligand polypeptide, or a small organic molecule agonist of Fas ligand activity. The Fas ligand polypeptide can be a biologically active Fas ligand polypeptide such as a Fas ligand polypeptide variant, a Fas ligand polypeptide derivative, a modified Fas ligand polypeptide, or a truncated Fas ligand polypeptide.

The use of FasL as an apoptosis-inducing molecule cell is advantageous in that Fas-mediated apoptosis both induces tolerance by elimination of antigen-reactive cytotoxic lymphocytes and maintains tolerance through polarization of the immune response towards protective phenotypes.

The present invention also contemplates the use of toxic molecules as cell death-inducing moieties. Such toxic molecules comprise both intracellular cell death inducing moieties and extracellular cell death inducing moieties (as described in detail above).

Exemplary intracellular cell death inducing toxic molecules which are contemplated by the present teachings include, but are not limited to, granzymes (e.g. Granzyme B), lectin, ricin, abrin, viscumin, modecin, diphtheria toxin, cholera toxin, gelonin, *Pseudomonas exotoxin, Shigella* toxin, botulinum toxin, tetanus toxin, calicheamicin, or pokeweed antiviral protein. These molecules typically cause cell death when taken up by the target cell (e.g. intracellular cell death inducing moieties) or, alternatively, may be introduced by regulatory cells during the process of cell-to-cell interaction.

Exemplary molecules that permeabilize the membrane to introduce toxic moieties which are contemplated by the present teachings include, but are not limited to, perforin, defensins and granulysin.

The cell death-inducing moiety of the present invention is preferably attached to the surface of the immune regulatory cell in order to directly bind the target cell (e.g. effector cell) upon direct cell to cell contact.

According to one embodiment, the cell death-inducing moiety is expressed (e.g., recombinantly) or immobilized on the surface of the immune regulatory cell. Any method can be used as long as the regulatory cells remain viable and functional (e.g., home, secrete cytokines etc.).

Any assay assessing cell viability can be used in accordance with the present teachings. Such assays include, for example, fluorescence-based assays detecting cell viability by microscopy, plate reader or flow cytometry (available for example from Invitrogen or Cell Biolabs, Inc.).

Methods of ex vivo immobilized molecules, such as cell death-inducing moieties, to the surface of cells are well known in the art and include, for example, cell coating via adhesion techniques, induction of apoptotic molecule expression on cell surfaces or genetic/epigenetic manipulations Cell coating with cell death-inducing moieties can be effected by any method known to one of ordinary skill in the art [see e.g. Yolcu E S et al, Immunity (2002) 17:795-808; Singh N P et al., Ann NY Acad Sci (2005); 1056:344-58]. Thus, for example, cell membranes may be linked directly to the cell death-inducing moiety or indirectly via bio complexes such as biotin/avidin or biotin/streptavidin system or via a linker (e.g. using for example EZ-Link Sulfo-NHS-LC-Biotin, Pierce, Rockford, Ill.). In these, the extracellular FasL domain is conjugated to streptavidin, core streptavidin or avidin. The membrane is directly biotinylated. Another way is to use a linker, which is typically a lipophilic moiety that incorporates in the cell membrane (e.g. using for example the PKH Cell Linker Kit available from Sigma-Aldrich Co). The lipophilic moiety, as for example that of the palmitate hydrocarbon chains, makes it possible to coat the cell membrane with this linker by insertion into the outer leaflet of the phospholipid bilayer of the cell membrane. An additional method is to conjugate the death ligands to universal or ubiquitous cell surface molecules such as glycophorin A.

According to another embodiment, induction of the surface expression of apoptotic inducing molecules may be obtained by direct adhesion of chimeric molecules to components of the membrane. The chimeric molecules comprise of one moiety that binds structural constituent of the membrane and another moiety that delivers apoptotic signals through ligation of death receptors (such molecules are described in detail hereinbelow).

According to a specific embodiment, FasL is conjugated to a surface (e.g. cell membrane) of the immune regulatory cell such that it is capable of trimerizing a Fas receptor on the target cell and thereby enhancing the efficiency of activation thereof.

The FasL may be cleavable or non-cleavable from the surface, although according to a presently preferred embodiment of the present invention, the FasL is non-cleavable such that trimerization of the Fas receptor may be maintained. An example of a naturally occurring non-cleaved human Fas ligand expressed only in membrane bound form is set forth in Gen Bank No. AAG60017.1. U.S. Pat. No. 6,951,919 teaches Fas ligands with enhanced apoptotic activities by virtue of being less susceptible to proteolysis.

Although the following relates to FasL this does not intend in anyway to limit the present teachings to FasL and the present teachings can be employed when using other cell death inducing moieties.

Alternatively, apoptosis-inducing molecules of the present invention may be expressed in the immune regulatory cells of the present invention. Thus, the present invention further contemplates genetically modified immune regulatory cells which may be used to express higher amount of apoptosis-inducing molecules on their surface. This can be achieved by intracellular insertion of genetic material encoding the molecule, which will be then transferred to and expressed on the cell membrane.

Thus, the invention further provides expression constructs encoding apoptosis-inducing polypeptides, which can be used to express same in the immune regulatory cells of the present invention. For example, a polynucleotide sequence derived from the cloning of mammalian FasL proteins, encoding all or a selected portion of the full-length protein, can be used to generate a recombinant form of a FasL polypeptide. An example of a nucleic acid sequence encoding wild type human FasL is set forth in GenBank No. U1182.1. An example of a nucleic acid sequence encoding naturally occurring non-cleaved human Fas ligand expressed only in membrane bound form is set forth in GenBank No. AF288573.

The nucleic acid construct (also referred to herein as an "expression vector") of the present invention typically includes additional sequences which render this vector suitable for replication and integration in prokaryotes, eukaryotes, or preferably both (e.g., shuttle vectors). In addition, typical cloning vectors may also contain a transcription and translation initiation sequence, transcription and translation terminator and a polyadenylation signal.

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for the present invention include those derived from polyoma virus, human or murine cytomegalovirus (CMV), the long term repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983, and Bell M P et al., J. Immunol. (2007) 179(3):1893-900, both of which are incorporated herein by reference.

In the construction of the expression vector, the promoter is preferably positioned approximately the same distance from the heterologous transcription start site as it is from the transcription start site in its natural setting. As is known in the art, however, some variation in this distance can be accommodated without loss of promoter function.

Polyadenylation sequences can also be added to the expression vector in order to increase the efficiency of the apoptosis-inducing polypeptides' mRNA translation. Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for the present invention include those derived from SV40.

In addition to the elements already described, the expression vector of the present invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

The expression vector of the present invention can further include additional polynucleotide sequences that allow, for example, the translation of several proteins from a single mRNA such as an internal ribosome entry site (IRES) and sequences for genomic integration of the promoter-chimeric polypeptide.

Examples of mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Expression vectors containing regulatory elements from eukaryotic viruses such as retroviruses can be also used. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/A+, pMT010/A+, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

Viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. Thus, the type of vector used by the present invention will depend on the cell type transformed. The ability to select suitable vectors according to the cell type transformed is well within the capabilities of the ordinary skilled artisan and as such no general description of selection consideration is provided herein. For example, bone marrow cells can be targeted using the human T cell leukemia virus type I (HTLV-I) and kidney cells may be targeted using the heterologous promoter present in the baculovirus *Autographa californica* nucleopolyhedrovirus (AcMNPV) as described in Liang C Y et al., (Arch Virol. 2004; 149:51-60).

Recombinant viral vectors are useful for in vivo expression of apoptosis-inducing polypeptides since they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

Various methods can be used to introduce the expression vector of the present invention into immune regulatory cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 1986; 4:504-512] and include, for example, stable or transient transfection, lipofection, electroporation and infection with recombinant viral vectors. In addition, see U.S. Pat. Nos. 5,464,764 and 5,487,992 for positive-negative selection methods.

Introduction of nucleic acids by viral infection offers several advantages over other methods such as lipofection and electroporation, since higher transfection efficiency can be obtained due to the infectious nature of viruses.

The efficacy of conjugation and/or expression of the cell death-inducing moieties as described herein can be evaluated by, for example, flow cytometry (e.g. using for instance anti-FasL, anti-TNFα, anti-TRAIL or anti-Tweak antibodies available from e.g. BD Pharmingen).

The method of the present invention may also be effected in vivo by administering to the subject a molecule comprising a cell death-inducing moiety heterologously attached to an immune regulatory cell-specific binding moiety. Such a molecule will bind the regulatory immune cells and these cells in turn will kill the target cells (e.g., effector cell or cancer cell).

As used herein the term "in vivo" refers to a process which is carried out within the organism (e.g., in the human body).

As used herein the term "heterologously attached" refers to a molecule comprising moieties (i.e. cell death-inducing moiety and immune regulatory cell-specific binding moiety) which are not conjugated in a natural occurring manner.

According to some embodiments the isolated molecule is a soluble synthetic molecule.

It will be appreciated that such a molecule can be used also in the ex vivo settings (as described above) although ex vivo settings are not restricted to higher specificity.

As used herein the term "immune regulatory cell-specific binding moiety" refers to any molecule (e.g. polypeptide) capable of specifically binding an immune regulatory cell and significantly less to other cells e.g., immune effector cells or other cells in a blood sample. The binding affinity of such a molecule to an immune regulatory cell is in the range of $10^{-4}$-$10^{-8}$ M Kd.

According to an embodiment, the immune regulatory cell-specific binding moiety comprises an antibody or a ligand. Preferably the antibody or ligand bind to a receptor on the immune regulatory cell and is presented on a surface thereof.

The term "ligand" as used in this invention includes any polypeptide capable of specifically binding a receptor on an immune regulatory cell.

Exemplary ligands of the present invention comprise, but are not limited to, cell surface markers of the various suppressor cell-phenotypes and molecules expressed preferentially by these cells such as components of the IL-2 receptor (CD25, CD122, CD132), L-selectin (CD62L), glucocorticoid-induced TNF receptor family related protein (GITR), CD134 (OX40), cytotoxic T-lymphocyte-associated antigen (CD152), CD39 and latency-associated peptide (LAP).

The term "antibody" as used in this invention includes intact molecules as well as functional fragments thereof, such as Fab, F(ab')2, and Fv that are capable of binding to macrophages. These functional antibody fragments are defined as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) (Fab)$_2$, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Antibody fragments according to some embodiments of the invention can be prepared by proteolytic hydrolysis of the antibody or by expression in *E. coli* or mammalian cells (e.g. Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab)2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. [Biochem. J. 73: 119-126 (1959)]. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al. [Proc. Nat'l Acad. Sci. USA 69:2659-62 (19720]. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by [Whitlow and Filpula, Methods 2: 97-105 (1991); Bird et al., Science 242:423-426 (1988); Pack et al., Bio/Technology 11:1271-77 (1993); and U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry [Methods, 2: 106-10 (1991)].

Humanized forms of non-human (e.g., murine) antibodies are chimeric molecules of immunoglobulins, immunoglobulin chains or fragments thereof (such as Fv, Fab, Fab', F(ab').sub.2 or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995).

Exemplary regulatory T cell-specific antibodies which may be used in accordance with the present teachings include anti-CD3, anti-CD122, anti-CD8, anti-CD4, anti-CD25, anti-GITR, anti-CTLA-4 and anti-CD62L all available e.g. from Abcam, Abbiotec, Abgent, AbFrontier. and Spring Bioscience.

Exemplary regulatory B cell-specific antibodies which may be used in accordance with the present teachings include anti-CD19, anti-CD20, anti-CD1d, anti-CD21 and anti-CD23 all available e.g. from Abbiotec Exemplary regulatory NK cell-specific binding moieties which may be used in accordance with the present teachings include anti-HLA-G and anti-CD3 available e.g. from ABR, BD Biosciences and BioLegend.

Exemplary regulatory myeloid cell-specific binding moieties which may be used in accordance with the present teachings include anti-CD11b, anti-CD43 and anti-CD86 available e.g. from Abcam, ABR and Abnova Corporation.

Exemplary regulatory APCs-specific binding moieties which may be used in accordance with the present teachings include, anti-B7-2 for dendritic cells (DCs) and anti-CD14, anti-CD11b or anti-CD68 for macrophages available e.g. from GeneTex, AbFrontier Co., Ltd., Novus Biologicals and Abcam.

It will be appreciated that the immune regulatory cell-specific binding moiety of the present invention may comprise a bifunctional (bispeciifc) or trifunctional (trispeciifc) antibody capable of binding two or three different polypeptides, respectively (e.g. CD4 and CD25 or CD62L, CD8 and CD122 on regulatory T cells). Such a bifunctional or tri-functional antibody may increase specificity of the antibody moiety.

As described in detail in the Examples section which follows, the present inventors have illustrated the therapeutic efficacy of the modified FasL-overexpressing Tregs in the treatment of diabetes (see Examples 7-9 hereinbelow), inflammatory bowel disease (see Example 11 hereinbelow) and transplant related diseases (see Examples 12-13 hereinbelow).

Thus, as mentioned, the immune regulatory cells or molecules of the present invention may be used for treating a medical condition in which suppression of immune effector cells is therapeutically beneficial in a subject in need thereof.

As used herein the term "treating" refers to preventing, curing, reversing, attenuating, alleviating, minimizing, suppressing or halting the deleterious effects of a medical condition in which suppression of immune effector cells is beneficial.

As used herein the phrase "medical condition in which suppression of immune effector cells is therapeutically beneficial" refers to any disease or disorder in which limiting or reducing the activity of immune effector cells can prevent an occurrence of a disease or medical symptoms associated therewith or halt disease progression or medical symptoms associated therewith (as further detailed hereinbelow).

As used herein the term "immune effector cells" refers to the cells of the immune system that have been activated by their cognate antigen.

According to one embodiment, the immune effector cells comprise effector T cells, effector B cells, effector myeloid cells, effector natural killer cells or effector antigen-presenting cells.

Effector T cells of the present invention refer to the subset of cytotoxic T cells which are actively involved in eliminating (e.g. killing) different types of cells that are infected with pathogens, or are otherwise damaged or dysfunctional. Effector T cells of the present invention also encompass memory T cells, which are a specialized subpopulation of antigen-specific T cells that persist for a long-term after an infection has resolved. Effector T cells may express the membrane markers CD4+ or CD8+.

Effector B cells of the present invention refer to the subset of B cells which secretes antibodies (also known as plasma cells). Effector B cells of the present invention also encompass memory B cells.

Effector natural killer (NK) cells of the present invention refer to the cytotoxic lymphocytes that are actively involved in eliminating (e.g. killing) cells by releasing perforin and granzyme. Effector NK cells of the present invention do not express T-cell antigen receptors (TCR), Pan T marker CD3 or surface immunoglobulins (Ig) B cell receptors. Effector NK cells of the present invention typically express the surface markers CD16 (FcγRIII) and CD56 and may express CD8.

Effector myeloid cells of the present invention refer to the leukocyte subset of cells that are not lymphocytes (e.g. T or B lymphocytes). These cells include resident and inflammatory granulocytic and monocytic myeloid cells.

Effector antigen-presenting cells (APCs) of the present invention refer to the subset of APCs which are capable of processing and presenting an antigen (via MHC class II and MHC class I molecules) and activating T cells. Effector APCs of the present invention may include, for example, dendritic cells (DCs), macrophages, activated epithelial cells, thymic epithelial cells, thyroid epithelial cells, fibroblasts, glial cells, pancreatic beta cells and vascular endothelial cells.

According to a specific embodiment, the immune effector cells comprise effector T cells.

As used herein the phrases "suppression of immune effector cells" or "suppressing immune effector cells" refers to reducing the activity or level of effector cells by at least about 10%, 20%, 30%, 40%, 50%, 60%, 70%, 80%, 90% or at least by 100% as compared to untreated effector cells.

Measuring the activity or level of immune effector cells (e.g. effector T cells) can be carried out using any method known to one of ordinary skill in the art, as for example, by measuring increased cell apoptosis (e.g. via cell staining of Anexin 5 expression on effector cells and flow cytometric analysis), by measuring decreased cell proliferation (e.g. via thymidine (3H) uptake), and by measuring reduced cytokine secretion such as INF-γ, TNF-α, IL-2 and IL-17 (e.g. via ELISA) by effector T cells In addition, T regulatory cell (Treg) suppression assay can be used to measure the suppression of effector T cells in-vitro. Thus, for example, effector T cells can be incubated with T regulatory cells in the presence of CCL1 (about 100-500 ng), stimulatory agents, e.g. anti-CD3 antibody and/or anti-CD28 antibody (about 0.5-2 μg/ml) and APCs for several days (e.g. 2-5 days). Proliferation can then be measured by thymidine (3H) uptake during the last 16 hours of incubation [see, for example, Thornton and Shevach (1998). "CD4+CD25+ immunoregulatory T cells suppress polyclonal T cell activation in vitro by inhibiting interleukin 2 production." Journal of Experimental Medicine 188(2): 287-296].

The medical condition may comprise, for example, an inflammatory disease, an autoimmune disease, a cancer, a hypersensitivity and a transplant-related disease.

Thus, the immune regulatory cells or molecules of the present invention may be used to treat inflammatory diseases.

The phrase "inflammatory disease", as used herein, refers to any disease or disorder which includes a component of inflammation, which is imperative to disease onset or progression. The inflammatory disease may be a chronic inflammatory disease, an acute inflammatory disease or a relapsing remitting disease.

According to an embodiment of the present invention, the inflammatory disease comprises inflammatory bowel disease (IBD), Crohn's disease, ulcerative colitis, rheumatoid arthritis, rheumatoid spondylitis, osteoarthritis, gouty arthritis, arthritic conditions, inflamed joints, eczema, inflammatory skin conditions, inflammatory eye conditions, conjunctivitis, pyresis, tissue necrosis resulting from inflammation, atopic dermatitis, hepatitis B antigen negative chronic active hepatitis, airway inflammation, asthma and bronchitis.

According to an embodiment of the present invention, the disease is inflammatory bowel disease (IBD).

According to an embodiment of the present invention, the disease is colitis.

According to an embodiment of the present invention, the disease is Crohn's disease.

According to another embodiment, the inflammatory disease is associated with hypersensitivity.

Examples of hypersensitivity include, but are not limited to, Type I hypersensitivity, Type II hypersensitivity, Type III hypersensitivity, Type IV hypersensitivity, immediate hypersensitivity, antibody mediated hypersensitivity, immune complex mediated hypersensitivity, T lymphocyte mediated hypersensitivity and DTH.

Type I or immediate hypersensitivity, such as asthma.

Type II hypersensitivity include, but are not limited to, rheumatoid diseases, rheumatoid autoimmune diseases, rheumatoid arthritis (Krenn V. et al., Histol Histopathol 2000 July; 15 (3):791), spondylitis, ankylosing spondylitis (Jan Voswinkel et al., Arthritis Res 2001; 3 (3): 189), systemic diseases, systemic autoimmune diseases, systemic lupus erythematosus (Erikson J. et al., Immunol Res 1998; 17 (1-2):49), sclerosis, systemic sclerosis (Renaudineau Y. et al., Clin Diagn Lab Immunol. 1999 March; 6 (2):156); Chan O T. et al., Immunol Rev 1999 June; 169:107), glandular diseases, glandular autoimmune diseases, pancreatic autoimmune diseases, diabetes, Type I diabetes (Zimmet P. Diabetes Res Clin Pract 1996 October; 34 Suppl:S125), thyroid diseases, autoimmune thyroid diseases, Graves' disease (Orgiazzi J. Endocrinol Metab Clin North Am 2000 June; 29 (2):339), thyroiditis, spontaneous autoimmune thyroiditis (Braley-Mullen H. and Yu S, J Immunol 2000 Dec. 15; 165 (12):7262), Hashimoto's thyroiditis (Toyoda N. et al., Nippon Rinsho 1999 August; 57 (8):1810), myxedema, idiopathic myxedema (Mitsuma T. Nippon Rinsho. 1999 August; 57 (8):1759); autoimmune reproductive diseases, ovarian diseases, ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), repeated fetal loss (Tincani A. et al., Lupus 1998; 7 Suppl 2:S107-9), neurodegenerative diseases, neurological diseases, neurological autoimmune diseases, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83), motor neuropathies (Kornberg A J. J Clin Neurosci. 2000 May; 7 (3):191), Guillain-Barre syndrome, neuropathies and autoimmune neuropathies (Kusunoki S. Am J Med. Sci. 2000 April; 319 (4):234), myasthenic diseases, Lambert-Eaton myasthenic syndrome (Takamori M. Am J Med. Sci. 2000 April; 319 (4):204), paraneoplastic neurological diseases, cerebellar atrophy, paraneoplastic cerebellar atrophy, non-paraneoplastic stiff man syndrome, cerebellar atrophies, progressive cerebellar atrophies, encephalitis, Rasmussen's encephalitis, amyotrophic lateral sclerosis, Sydeham chorea, Gilles de la Tourette syndrome, polyendocrinopathies, autoimmune polyendocrinopathies (Antoine J C. and Honnorat J. Rev Neurol (Paris) 2000 January; 156 (1):23); neuropathies, dysimmune neuropathies (Nobile-Orazio E. et al., Electroencephalogr Clin Neurophysiol Suppl 1999; 50:419); neuromyotonia, acquired neuromyotonia, arthrogryposis multiplex congenita (Vincent A. et al., Ann N Y Acad. Sci. 1998 May 13; 841:482), cardiovascular diseases, cardiovascular autoimmune diseases, atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), granulomatosis, Wegener's granulomatosis, arteritis, Takayasu's arteritis and Kawasaki syndrome (Praprotnik S. et al., Wien Klin Wochenschr 2000 Aug. 25; 112 (15-16):660); anti-factor VIII autoimmune disease (Lacroix-Desmazes S. et al., Semin Thromb Hemost. 2000; 26 (2):157); vasculitises, necrotizing small vessel vasculitises, microscopic polyangiitis, Churg and Strauss syndrome, glomerulonephritis, pauci-immune focal necrotizing glomerulonephritis, crescentic glomerulonephritis (Noel L H. Ann Med Interne (Paris). 2000 May; 151 (3):178); antiphospholipid syndrome (Flamholz R. et al., J Clin Apheresis 1999; 14 (4):171); heart failure, agonist-like β-adrenoceptor antibodies in heart failure (Wallukat G. et al., Am J. Cardiol. 1999 Jun. 17; 83 (12A):75H), thrombocytopenic purpura (Moccia F. Ann Ital Med. Int. 1999 April-June; 14 (2):114); hemolytic anemia, autoimmune hemolytic anemia (Efremov D G. et al., Leuk Lymphoma 1998 January; 28 (3-4):285), gastrointestinal diseases, autoimmune diseases of the gastrointestinal tract, intestinal diseases, chronic inflammatory intestinal disease (Garcia Herola A. et al., Gastroenterol Hepatol. 2000 January; 23 (1):16), celiac disease (Landau Y E. and Shoenfeld Y. Harefuah 2000 Jan. 16; 138 (2):122), autoimmune diseases of the musculature, myositis, autoimmune myositis, Sjogren's syndrome (Feist E. et al., Int Arch Allergy Immunol 2000 September; 123 (1):92); smooth muscle autoimmune disease (Zauli D. et al., Biomed Pharmacother 1999 June; 53 (5-6):234), hepatic diseases, hepatic autoimmune diseases, autoimmune hepatitis (Manns M P. J Hepatol 2000 August; 33 (2):326) and primary biliary cirrhosis (Strassburg C P. et al., Eur J Gastroenterol Hepatol. 1999 June; 11 (6):595).

Type IV or T cell mediated hypersensitivity, include, but are not limited to, rheumatoid diseases, rheumatoid arthritis (Tisch R, McDevitt H O. Proc Natl Acad Sci U S A 1994 Jan. 18; 91 (2):437), systemic diseases, systemic autoimmune diseases, systemic lupus erythematosus (Datta S K., Lupus 1998; 7 (9):591), glandular diseases, glandular autoimmune diseases, pancreatic diseases, pancreatic autoimmune diseases, Type 1 diabetes (Castano L. and Eisenbarth G S. Ann. Rev Immunol. 8:647); thyroid diseases, autoimmune thyroid diseases, Graves' disease (Sakata S. et al., Mol Cell Endocrinol 1993 March; 92 (1):77); ovarian diseases (Garza K M. et al., J Reprod Immunol 1998 February; 37 (2):87), prostatitis, autoimmune prostatitis (Alexander R B. et al., Urology 1997 December; 50 (6):893), polyglandular syndrome, autoimmune polyglandular syndrome, Type I autoimmune polyglandular syndrome (Hara T. et al., Blood. 1991 Mar. 1; 77 (5):1127), neurological diseases, autoimmune neurological diseases, multiple sclerosis, neuritis, optic neuritis (Soderstrom M. et al., J Neurol Neurosurg Psychiatry 1994 May; 57 (5):544), myasthenia gravis (Oshima M. et al., Eur J Immunol 1990 December; 20 (12):2563), stiff-man syndrome (Hiemstra H S. et al., Proc Natl Acad Sci USA 2001 Mar. 27; 98 (7):3988), cardiovascular diseases, cardiac autoimmunity in Chagas' disease (Cunha-Neto E. et al., J Clin Invest 1996 Oct. 15; 98 (8):1709), autoimmune thrombocytopenic purpura (Semple J W. et al., Blood 1996 May 15; 87 (10):4245), anti-helper T lymphocyte autoimmunity (Caporossi A P. et al., Viral Immunol 1998; 11 (1):9), hemolytic anemia (Sallah S. et al., Ann Hematol 1997 March; 74 (3):139), hepatic diseases, hepatic autoimmune diseases, hepatitis, chronic active hepatitis (Franco A. et al., Clin Immunol Immunopathol 1990 March; 54 (3):382), biliary cirrhosis, primary biliary cirrhosis (Jones D E. Clin Sci (Colch) 1996 November; 91 (5):551), nephric diseases, nephric autoimmune diseases, nephritis, interstitial nephritis (Kelly C J. J Am Soc Nephrol 1990 August; 1 (2):140), connective tissue diseases, ear diseases, autoimmune connective tissue diseases, autoimmune ear disease (Yoo T J. et al., Cell Immunol 1994 August; 157 (1):249), disease of the inner ear (Gloddek B. et al., Ann N Y Acad Sci 1997 Dec. 29; 830:266), skin diseases, cutaneous diseases, dermal diseases, bullous skin diseases, pemphigus vulgaris, bullous pemphigoid and pemphigus foliaceus.

Examples of delayed type hypersensitivity include, but are not limited to, contact dermatitis and drug eruption.

Examples of types of T lymphocyte mediating hypersensitivity include, but are not limited to, helper T lymphocytes and cytotoxic T lymphocytes.

Examples of helper T lymphocyte-mediated hypersensitivity include, but are not limited to, $T_h1$ lymphocyte mediated hypersensitivity and $T_h2$ lymphocyte mediated hypersensitivity.

According to an embodiment of the present invention, the medical condition is an inflammatory autoimmune disease.

Herein, the phrase "autoimmune disease" refers to a disease resulting from a disordered immune reaction (e.g., antibody production) generated against components of one's own body (i.e. auto-antigens). According to the present teachings the autoimmune disease is associated at least in part with uncontrolled (increased) immune effector cell activity (e.g. T effector cell). The immune system of the subject then activates an inflammatory cascade aimed at cells and tissues presenting those specific self antigens. The destruction of the antigen, tissue, cell type, or organ attacked by the individual's own immune system gives rise to the symptoms of the disease.

According to one embodiment, the autoimmune disease comprises diabetes mellitus type I, diabetes mellitus type II, systemic lupus erythematosis, multiple sclerosis, myasthenia gravis, progressive systemic sclerosis, hyperimmunoglobin E, Hashimoto's thyroiditis, familial Mediterranean fever, Grave's disease, autoimmune haemolytic anemia or primary biliary cirrhosis.

According to a specific embodiment of the present invention, the disease is diabetes mellitus type I or diabetes mellitus type II.

As used herein "diabetes" refers to a disease resulting either from an absolute deficiency of insulin (type 1 diabetes) due to a defect in the biosynthesis or production of insulin, or a relative deficiency of insulin in the presence of insulin resistance (type 2 diabetes), i.e., impaired insulin action, in an organism. The diabetic patient thus has absolute or relative insulin deficiency, and displays, among other symptoms and signs, elevated blood glucose concentration, presence of glucose in the urine and excessive discharge of urine.

Additional autoimmune diseases which may be treated according to the present methods include, but are not limited to, cardiovascular diseases, rheumatoid diseases, glandular diseases, gastrointestinal diseases, cutaneous diseases, hepatic diseases, neurological diseases, muscular diseases, nephric diseases, diseases related to reproduction, connective tissue diseases and systemic diseases.

Examples of autoimmune cardiovascular diseases include, but are not limited to atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), Wegener's granulomatosis, Takayasu's arteritis, Kawasaki syndrome (Praprotnik S. et al., Wien Klin Wochenschr 2000 Aug. 25; 112 (15-16):660), anti-factor VIII autoimmune disease (Lacroix-Desmazes S. et al., Semin Thromb Hemost. 2000; 26 (2):157), necrotizing small vessel vasculitis, microscopic polyangiitis, Churg and Strauss syndrome, pauci-immune focal necrotizing and crescentic glomerulonephritis (Noel L H. Ann Med Interne (Paris). 2000 May; 151 (3):178), antiphospholipid syndrome (Flamholz R. et al., J Clin Apheresis 1999; 14 (4):171), antibody-induced heart failure (Wallukat G. et al., Am J. Cardiol. 1999 Jun. 17; 83 (12A):75H), thrombocytopenic purpura (Moccia F. Ann Ital Med. Int. 1999 April-June; 14 (2):114; Semple J W. et al., Blood 1996 May 15; 87 (10):4245), autoimmune hemolytic anemia (Efremov D G. et al., Leuk Lymphoma 1998 January; 28 (3-4):285; Sallah S. et al., Ann Hematol 1997 March; 74 (3):139), cardiac autoimmunity in Chagas' disease (Cunha-Neto E. et al., J Clin Invest 1996 Oct. 15; 98 (8):1709) and anti-helper T lymphocyte autoimmunity (Caporossi A P. et al., Viral Immunol 1998; 11 (1):9).

Examples of autoimmune rheumatoid diseases include, but are not limited to rheumatoid arthritis (Krenn V. et al., Histol Histopathol 2000 July; 15 (3):791; Tisch R, McDevitt H O. Proc Natl Acad Sci units S A 1994 Jan. 18; 91 (2):437) and ankylosing spondylitis (Jan Voswinkel et al., Arthritis Res 2001; 3 (3): 189).

Examples of autoimmune glandular diseases include, but are not limited to, pancreatic disease, Type I diabetes, thyroid disease, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome. diseases include, but are not limited to autoimmune diseases of the pancreas, Type 1 diabetes (Castano L. and Eisenbarth G S. Ann. Rev. Immunol. 8:647; Zimmet P. Diabetes Res Clin Pract 1996 October; 34 Suppl: S125), autoimmune thyroid diseases, Graves' disease (Orgiazzi J. Endocrinol Metab Clin North Am 2000 June; 29 (2):339; Sakata S. et al., Mol Cell Endocrinol 1993 March; 92 (1):77), spontaneous autoimmune thyroiditis (Braley-Mullen H. and Yu S, J Immunol 2000 Dec. 15; 165 (12): 7262), Hashimoto's thyroiditis (Toyoda N. et al., Nippon Rinsho 1999 August; 57 (8):1810), idiopathic myxedema (Mitsuma T. Nippon Rinsho. 1999 August; 57 (8):1759), ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), autoimmune prostatitis (Alexander R B. et al., Urology 1997 December; 50 (6):893) and Type I autoimmune polyglandular syndrome (Hara T. et al., Blood. 1991 Mar. 1; 77 (5):1127).

Examples of autoimmune gastrointestinal diseases include, but are not limited to, chronic inflammatory intestinal diseases (Garcia Herola A. et al., Gastroenterol Hepatol. 2000 January; 23 (1):16), celiac disease (Landau Y E. and Shoenfeld Y. Harefuah 2000 Jan. 16; 138 (2):122), colitis, ileitis and Crohn's disease.

Examples of autoimmune cutaneous diseases include, but are not limited to, autoimmune bullous skin diseases, such as, but are not limited to, pemphigus vulgaris, bullous pemphigoid and pemphigus foliaceus.

Examples of autoimmune hepatic diseases include, but are not limited to, hepatitis, autoimmune chronic active hepatitis (Franco A. et al., Clin Immunol Immunopathol 1990 March; 54 (3):382), primary biliary cirrhosis (Jones D E. Clin Sci (Colch) 1996 November; 91 (5):551; Strassburg C P. et al., Eur J Gastroenterol Hepatol. 1999 June; 11 (6):595) and autoimmune hepatitis (Manns M P. J Hepatol 2000 August; 33 (2):326).

Examples of autoimmune neurological diseases include, but are not limited to, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83; Oshima M. et al., Eur J Immunol 1990 December; 20 (12):2563), neuropathies, motor neuropathies (Kornberg A J. J Clin Neurosci. 2000 May; 7 (3):191); Guillain-Barre syndrome and autoimmune neuropathies (Kusunoki S. Am J Med. Sci. 2000 April; 319 (4):234), myasthenia, Lambert-Eaton myasthenic syndrome (Takamori M. Am J Med. Sci. 2000 April; 319 (4):204); paraneoplastic neurological diseases, cerebellar atrophy, paraneoplastic cerebellar atrophy and stiff-man syndrome (Hiemstra H S. et al., Proc Natl Acad Sci units S A 2001 Mar. 27; 98 (7):3988); non-paraneoplastic stiff man syndrome, progressive cerebellar atrophies, encephalitis, Rasmussen's encephalitis, amyotrophic lateral sclerosis, Sydeham chorea, Gilles de la Tourette syndrome and autoimmune polyendocrinopathies (Antoine J C. and Honnorat J. Rev Neurol (Paris) 2000 January; 156 (1):23); dysimmune neuropathies (Nobile-Orazio E. et al., Electroencephalogr Clin Neurophysiol Suppl 1999; 50:419); acquired neuromyotonia, arthrogryposis multiplex congenita (Vincent A. et al., Ann N Y Acad. Sci. 1998 May 13; 841:482), neuritis, optic neuritis (Soderstrom M. et al., J Neurol Neurosurg Psychiatry 1994 May; 57 (5):544) and neurodegenerative diseases.

Examples of autoimmune muscular diseases include, but are not limited to, myositis, autoimmune myositis and primary Sjogren's syndrome (Feist E. et al., Int Arch Allergy Immunol 2000 September; 123 (1):92) and smooth muscle autoimmune disease (Zauli D. et al., Biomed Pharmacother 1999 June; 53 (5-6):234).

Examples of autoimmune nephric diseases include, but are not limited to, nephritis and autoimmune interstitial nephritis (Kelly C J. J Am Soc Nephrol 1990 August; 1 (2): 140).

Examples of autoimmune diseases related to reproduction include, but are not limited to, repeated fetal loss (Tincani A. et al., Lupus 1998; 7 Suppl 2:S107-9).

Examples of autoimmune connective tissue diseases include, but are not limited to, ear diseases, autoimmune ear diseases (Yoo T J. et al., Cell Immunol 1994 August; 157 (1):249) and autoimmune diseases of the inner ear (Gloddek B. et al., Ann N Y Acad Sci 1997 Dec. 29; 830:266).

Examples of autoimmune systemic diseases include, but are not limited to, systemic lupus erythematosus (Erikson J. et al., Immunol Res 1998; 17 (1-2):49) and systemic sclerosis (Renaudineau Y. et al., Clin Diagn Lab Immunol. 1999 March; 6 (2):156); Chan O T. et al., Immunol Rev 1999 June; 169:107).

The immune regulatory cells or molecules of the present invention may also be used to treat transplantation related disease.

Herein, the phrase "transplantation related disease", refers to any disease or disorder which occurs following or as a result of a transplantation procedure or preconditioning thereto. The transplantation related disease may be a chronic disease or an acute disease and may occur at any stage or time following transplantation of a graft (e.g. several hours, several days, several weeks, several months or several years following transplantation).

It will be appreciated that the present teachings contemplate treatment of a transplantation related disease following transplantation of any graft including, for example, a solid organ or tissue graft (e.g. kidney, heart, lung, spleen, liver, skin, intestines, etc.) or a cell graft such as immature hematopoietic cells, including stem cells, which can be derived, for example, from bone marrow, mobilized peripheral blood (by for example leukapheresis), fetal liver, yolk sac and/or cord blood of a donor (e.g. non-syngeneic donor).

Examples of diseases associated with transplantation of a graft include, but are not limited to, graft rejection, chronic graft rejection, subacute graft rejection, hyperacute graft rejection, acute graft rejection and graft versus host disease (GVHD).

According to a specific embodiment, the transplantation related disease is graft versus host disease (GVHD).

According to another embodiment, the transplantation related disease is graft rejection.

It will be appreciated that the immune regulatory cells of the present invention may further induce tolerance to a graft.

The immune regulatory cells or molecules of the present invention may also be used to treat allergic diseases.

Examples of allergic diseases include, but are not limited to, asthma, hives, urticaria, pollen allergy, dust mite allergy, venom allergy, cosmetics allergy, latex allergy, chemical allergy, drug allergy, insect bite allergy, animal dander allergy, stinging plant allergy, poison ivy allergy and food allergy.

The immune regulatory cells or molecules of the present invention may also be used to treat cancerous diseases.

Examples of cancer include but are not limited to carcinoma, lymphoma, blastoma, sarcoma, and leukemia. Particular examples of cancerous diseases but are not limited to: Myeloid leukemia such as Chronic myelogenous leukemia. Acute myelogenous leukemia with maturation. Acute promyelocytic leukemia, Acute nonlymphocytic leukemia with increased basophils, Acute monocytic leukemia. Acute myelomonocytic leukemia with eosinophilia; Malignant lymphoma, such as Birkitt's Non-Hodgkin's; Lymphoctyic leukemia, such as Acute lumphoblastic leukemia. Chronic lymphocytic leukemia; Myeloproliferative diseases, such as Solid tumors Benign Meningioma, Mixed tumors of salivary gland, Colonic adenomas; Adenocarcinomas, such as Small cell lung cancer, Kidney, Uterus, Prostate, Bladder, Ovary, Colon, Sarcomas, Liposarcoma, myxoid, Synovial sarcoma, Rhabdomyosarcoma (alveolar), Extraskeletel myxoid chonodrosarcoma, Ewing's tumor; other include Testicular and ovarian dysgerminoma, Retinoblastoma, Wilms' tumor, Neuroblastoma, Malignant melanoma, Mesothelioma, breast, skin, prostate, and ovarian.

It will be appreciated that the present teachings do not contemplate treating conditions in which suppression of effector cells can be harmful. Thus, for example, the present teachings contemplate the treatment of cancer following chemoablation or radioablation or in situations in which the natural immune system is malfunctioning.

As used herein, the term "subject" or "subject in need thereof" refers to a mammal, preferably a human being, male or female at any age that is in need of suppression of immune effector cells (e.g. CD4+ or CD8+ effector T cells, effector B cells, etc.). Typically, the subject has been diagnosed with an inflammatory disease, an autoimmune disease, a cancer, a hypersensitivity or a transplant-related disease, however, the subject may also have been diagnosed with any other disease which is amenable to treatment via suppression of immune effector cells. The subject may or may not have received previous treatment for the disease. Examples of such disorders are provided hereinabove.

For ex vivo therapy, immune regulatory cells are preferably treated as to comprise an exogenous cell death-inducing moiety (as detailed in further detail hereinabove), following which they are administered to the subject in need thereof.

Administration of the ex vivo treated cells of the present invention can be effected using any suitable route of introduction, such as intravenous, intraperitoneal, intra-kidney, intra-gastrointestinal track, subcutaneous, transcutaneous, intramuscular, intracutaneous, intrathecal, epidural, and rectal. According to presently preferred embodiments, the ex vivo treated cells of the present invention are introduced directly to a site of inflammation.

As mentioned, the immune regulatory cells may be obtained from any syngeneic or non-syngeneic (i.e., allogeneic) donor.

Since non-syngeneic cells are likely to induce an immune reaction when administered to the body several approaches have been developed to reduce the likelihood of rejection of non-syngeneic cells. These include either suppressing the recipient immune system or encapsulating the non-syngeneic cells in immunoisolating, semipermeable membranes before transplantation.

Encapsulation techniques are generally classified as microencapsulation, involving small spherical vehicles, and macroencapsulation, involving larger flat-sheet and hollow-fiber membranes (Uludag, H. et al. (2000). Technology of mammalian cell encapsulation. Adv Drug Deliv Rev 42, 29-64).

Methods of preparing microcapsules are known in the art and include for example those disclosed in: Lu, M. Z. et al. (2000). Cell encapsulation with alginate and alpha-phenoxycinnamylidene-acetylated poly(allylamine). Biotechnol Bioeng 70, 479-483; Chang, T. M. and Prakash, S. (2001) Procedures for microencapsulation of enzymes, cells and genetically engineered microorganisms. Mol Biotechnol 17, 249-260; and Lu, M. Z., et al. (2000). A novel cell encapsulation method using photosensitive poly(allylamine alpha-cyanocinnamylideneacetate). J Microencapsul 17, 245-521.

For example, microcapsules are prepared using modified collagen in a complex with a ter-polymer shell of 2-hydroxyethyl methylacrylate (HEMA), methacrylic acid (MAA), and methyl methacrylate (MMA), resulting in a capsule thickness of 2-5 µm. Such microcapsules can be further encapsulated with an additional 2-5 µm of ter-polymer shells in order to impart a negatively charged smooth surface and to minimize plasma protein absorption (Chia, S. M. et al. (2002). Multi-layered microcapsules for cell encapsulation. Biomaterials 23, 849-856).

Other microcapsules are based on alginate, a marine polysaccharide (Sambanis, A. (2003). Encapsulated islets in diabetes treatment. Diabetes Thechnol Ther 5, 665-668), or its derivatives. For example, microcapsules can be prepared by the polyelectrolyte complexation between the polyanions sodium alginate and sodium cellulose sulphate and the polycation poly(methylene-co-guanidine) hydrochloride in the presence of calcium chloride.

It will be appreciated that cell encapsulation is improved when smaller capsules are used. Thus, for instance, the quality control, mechanical stability, diffusion properties, and in vitro activities of encapsulated cells improved when the capsule size was reduced from 1 mm to 400 µm (Canaple, L. et al. (2002). Improving cell encapsulation through size control. J Biomater Sci Polym Ed 13, 783-96). Moreover, nanoporous biocapsules with well-controlled pore size as small as 7 nm, tailored surface chemistries, and precise microarchitectures were found to successfully immunoisolate microenvironments for cells (See: Williams, D. (1999). Small is beautiful: microparticle and nanoparticle technology in medical devices. Med Device Technol 10, 6-9; and Desa T. A. (2002). Microfabrication technology for pancreatic cell encapsulation. Expert Opin Biol Ther 2, 633-646).

Examples of immunosuppressive agents which may be used in conjunction with the ex vivo treatment include, but are not limited to, steroids, rapamycin, fludarabin methotrexate, cyclophosphamide, cyclosporine, cyclosporin A, chloroquine, hydroxychloroquine, sulfasalazine (sulphasalazopyrine), gold salts, D-penicillamine, leflunomide, azathioprine, anakinra, infliximab (REMICADE.sup.R), etanercept, TNFα. blockers, a biological agent that targets an inflammatory cytokine, and Non-Steroidal Anti-Inflammatory Drug (NSAIDs). Examples of NSAIDs include, but are not limited to acetyl salicylic acid, choline magnesium salicylate, diflunisal, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, Cox-2 inhibitors and tramadol.

According to another embodiment of the present invention, treatment is effected by administering to the subject a molecule comprising a cell death-inducing moiety heterologously attached to an immune regulatory cell-specific binding moiety.

For in vivo therapy, the molecule (as detailed in further detail hereinabove) is administered to the subject as is or as part of a pharmaceutical composition.

Thus, the immune regulatory cells or the molecules of the present invention can be administered to the individual per se or as part of a pharmaceutical composition which also includes a physiologically acceptable carrier.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the agent accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, inrtaperitoneal, intranasal, or intraocular injections.

Alternately, one may administer the pharmaceutical composition in a local rather than systemic manner, for example, via injection of the pharmaceutical composition directly into a tissue region of a patient.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuos infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients (immune regulatory cells or molecules of the present invention) effective to prevent, alleviate or ameliorate symptoms of a disorder (e.g., autoimmune disease) or prolong the survival of the subject being treated.

According to a specific embodiment, the therapeutically effective amount is for killing the immune effector cells to the extent of amelioration, arrest or abrogation of immune reactivity against self or foreign antigens.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide ample levels of the active ingredient which are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

According to one embodiment, the subject is administered at least about $0.6 \times 10^6$ Treg cells per kg, about $1.2 \times 10^6$ Treg cells per kg, about $0.6 \times 10^7$ Treg cells per kg, about $1.2 \times 10^7$ Treg cells per kg, about $0.6 \times 10^8$ Treg cells per kg, about $0.8 \times 10^8$ Treg cells per kg, about $1.0 \times 10^8$ Treg cells per kg, about $1.2 \times 10^8$ Treg cells per kg, about $1.4 \times 10^8$ Treg cells per kg, about $1.6 \times 10^8$ Treg cells per kg, about $1.8 \times 10^8$ Treg cells per kg or about $2.0 \times 10^8$ Treg cells per kg.

Depending on the severity and responsiveness of the condition to be treated, dosing can be of a single or a plurality of administrations, with course of treatment lasting from several days to several weeks or until cure is effected or diminution of the disease state is achieved.

It will be appreciated that in order to treat existing diseases or prevent disease occurrence repeated administration of the immune regulatory cells or molecules of the present invention are contemplated.

Furthermore, the immune regulatory cells or molecules of the present invention may be administered at different stages of the disease. Thus, for example, the immune regulatory cells or molecules of the present invention may be administered before symptoms of a disease occur (i.e. in order to prevent disease occurrence), alternatively, the immune regulatory cells or molecules may be administered during an acute inflammatory condition or during disease remission.

The amount of a composition to be administered will, of course, be dependent on the subject being treated, the severity of the affliction, the manner of administration, the judgment of the prescribing physician, etc. The dosage and timing of administration will be responsive to a careful and continuous monitoring of the individual changing condition.

It will be appreciated that animal models exist by which the immune effector cells or molecules of the present invention of the present invention may be tested prior to human treatment. For example, Type I diabetes models include, pancreatectomy in dogs, spontaneous rodent models (e.g. BBDP rats and the NOD mice). Type II diabetes models and obese animal models include, db/db (diabetic) mice, Zucker diabetic fatty (ZDF) rats, sand rats (*Psammomys obesus*) and obese rhesus monkeys. Likewise, animal models for inflammatory bowel disease include the murine models of experimentally-induced colitis e.g., by administration of dextran sodium sulfate (DSS) in drinking water or by rectal administration of trinitrobenzene sulfonic acid (TNBS). Animal models for transplantation include allograft and xenograft transplantation models (see e.g. emice(dot)nci(dot)nih(dot)gov/aam/mouse/transplantation-mouse-models-1).

Regardless of the above, the immune regulatory cells or the molecules of the present invention are administered at an amount selected to avoid unwanted side-effects associated with elevated concentrations thereof.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

The agents of the invention can be suitably formulated as pharmaceutical compositions which can be suitably packaged as an article of manufacture. Such an article of manufacture comprises a label for use in treating disease (e.g. autoimmune disease, inflammatory disease, transplant-related disease etc.), the packaging material packaging a pharmaceutically effective amount of the immune regulatory cells or the molecules of the present invention.

It will be appreciated that treatment of the medical conditions as mentioned above may be combined with any other method known in the art. For example, treatment of autoimmune diseases, inflammatory diseases and transplantation related diseases according to the present invention may be combined with other treatment methods known in the art (i.e., combination therapy).

Thus, for example, diabetes may be treated with the immune regulatory cells or the molecules of the present invention in conjunction with e.g. insulin including short-acting insulin [e.g. lispro (Humalog) or aspart (NovoLog)] and longer acting insulin [e.g. Neutral Protamine Hagedorn (NPH), Lente, glargine (Lantus), detemir, or ultralente] and oral medication for control of blood sugar levels e.g. sulfonylurea or biguanide [metformin Glucophage)].

Inflammatory diseases may be treated with the immune regulatory cells or the molecules of the present invention in conjunction with other agents including, but not limited to, NSAIDs (Non-Steroidal Anti-inflammatory Drugs e.g. aspirin, ibuprofen or naproxen), corticosteroids (such as prednisone), anti-histamines, and other medications e.g. methotrexate, sulfasalazine, leflunomide, anti-TNF medications, cyclophosphamide and mycophenolate.

Transplantation related diseases (e.g. GVHD) may be treated with the immune regulatory cells or the molecules of the present invention in conjunction with other agents including, but not limited to, immunosuppressive drugs such as CTLA4-Ig, anti-CD40 antibodies, anti-CD40 ligand antibodies, anti-B7 antibodies, anti-CD3 antibodies (for example, anti-human CD3 antibody OKT3), methotrexate (MTX), rapamycin, prednisone, methyl prednisolone, azathioprene, cyclosporin A (CsA), tacrolimus, cyclophosphamide and fludarabin, mycophenolate mofetil, daclizumab [a humanized (IgG1 Fc) anti-IL2R alpha chain (CD25) antibody], and anti-T-lymphocyte antibodies conjugated to toxins (for example, cholera A chain, or *Pseudomonas* toxin). Furthermore, the present methods may be combined with irradiation therapy or chemotherapy.

The present invention therefore contemplates articles of manufacture comprising the immune regulatory cells or the molecules of the present invention and an additional agent (e.g. an immunosuppressive agent) being packaged in a packaging material and identified in print, in or on the packaging material for use in the treatment of the medical condition (e.g. transplant-related disease).

In addition, the present invention further contemplates administration of cytokines which may prolong the activity of the ex vivo administered immune regulatory cells. Such cytokines may include, for example, IL-2 (e.g. conjugated IL-2 complexes), IL-10, TGF-β, TNF-α, TRAIL, G-CSF or GM-CSF.

The immune regulatory cells or molecules of the present invention may be administered prior to, concomitantly with or following administration of the latter.

As mentioned, the immune regulatory cells of the present invention may be obtained from a syngeneic or non-syngeneic donor.

Thus, according to one embodiment, in order to induce graft tolerance the immune regulatory cells are obtained from the donor (i.e. non-syngeneic).

Thus, according to another embodiment, in order to alleviate GVHD the immune regulatory cells are obtained from the donor (i.e. non-syngeneic).

Thus, according to another embodiment, in order to alleviate graft rejection the immune regulatory cells are obtained from the subject (i.e. syngeneic).

Thus, according to another embodiment, in order to treat or prevent an autuoimmune disease (e.g. diabetes) or inflammatory disease (e.g. IBD) the immune regulatory cells are preferably obtained from the subject (i.e. syngeneic).

In order to test treatment efficacy, the subject may be evaluated by physical examination as well as using any method known in the art, as for example, for diabetes by finger stick blood glucose test, fasting plasma glucose test, oral glucose tolerance test, glycosylated hemoglobin or hemoglobin A1c, body mass index (BMI) and the like.

It is expected that during the life of a patent maturing from this application many relevant regulatory cell markers and cell-death inducing molecules (e.g., apoptotic inducing molecules) will be developed and the scope of the terms regulatory cell markers and cell-death inducing molecules are intended to include all such new technologies a priori.

As used herein the term "about" refers to ±10%.

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton &

Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials And Experimental Procedures

Mice and Diabetes Monitoring: Mice used in this study were C57BL/6 (wild type), B6.Cg-Foxp3$^{tm2Tch}$ transgenic mice (expressing GFP under control of the FoxP3 promoter), non-obese diabetic (NOD) and NOD SCID mice purchased from Jackson Laboratories (Bar Harbor, Me.). The inbred NOD colony was housed in a barrier facility. The Institutional Animal Care Committee approved all procedures.

Diabetes Monitoring: Blood glucose was monitored between 9-11 AM in tail blood samples at weekly intervals using a glucometer (Accu-Chek Sensor, Roche Diagnostics, USA). Diabetes was defined as two consecutive blood glucose measurements above 200 mg/dl. Glucose tolerance test was performed by intraperitoneal administration of 2 g glucose and measurement of blood glucose at 30, 60 and 120 minutes.

Radiation: Recipients were conditioned by sublethal dose of total body irradiation (TBI) of 650 rad using an X-ray irradiator (RadSource 2000, Brentwood, Tenn.) at a rate of 106 rad/min.

Cell Preparation: Spleens and lymph nodes were harvested and gently minced on a 40 μM nylon mesh in HBSS (Kibbutz Beit Haemek, Israel) to prepare single cell suspensions. The cells were aspirated with an 18 G needle to obtain single cell suspensions. Isolation of lymphocytes was performed by centrifugation over 1.5 ml Lympholyte-M (Cedarlane, Ontario, Canada) and T cells were collected after immunomagnetic depletion using antibodies against MAC-1, GR-1 and B220. All antibodies were obtained from hybridoma cell cultures (ATCC, Manassas, Va.). Antibody-coated cells were washed twice with PBS containing 2% FCS and were incubated with sheep-anti-rat IgG conjugated to M-450 magnetic beads at a ratio of 4-5 beads per cell (Dynal Inc.). Conjugated cells were precipitated by exposure to a magnetic field. The purity of T cell elution was reassessed by flow cytometry using primary labeled monoclonal antibodies against CD4 and CD8. For flow cytometry, the red cells were removed by ammonium chloride lysis for 4 minutes at room temperature. The reaction was arrested with excess ice-cold solution and cells were washed. T cell depleted BMC (TCD-BMC) were prepared with mAb against CD4, CD5 and CD8 (hybridoma cell cultures), and lineage-negative (lin$^-$) BMC with mAb against CD5, MAC-1, GR-1. NK1.1 and B220 (hybridoma) and Ter119 (eBioscience, San Diego, Calif.).

Flow Cytometry: Cells were labeled by incubation for 45 minutes at 4° C. with the appropriate antibodies conjugated to fluorescein isothyocyanite (FITC), phycoerythrin (PE), allophycocyanin (APC) and peridinin chlorophyll a-protein (PerCP, BD Pharmingen, San Diego, Calif.): CD4 (clone R M 4-5), CD8 (clone 53-6.7), CD25 (clone PC61.5). Cells were washed in PBS, incubated for 45 min at 4° C. with labeled primary mAb or counterstained with a fluorochrome-labeled secondary mAb. FoxP3 was determined following permeabilization and intracellular staining with a PE-labeled antibody (Foxp3 staining buffer set NRRF-30, eBioscience). Antibodies were purchased from BD Pharmingen and eBioscience. Apoptosis and early death were determined using Annexin-V (IQ Products, Groningen, The Netherlands) and non-specific membrane permeabilization was assessed with 7-aminoactinomycin-D (7-AAD, Sigma). Positive staining was determined on a log scale, normalized with control cells stained with isotype control antibodies.

Isolation of Cells According to CD25 Expression: CD25$^-$ and CD25$^+$ subsets of CD4$^+$ T cells were isolated from the spleens and mesenteric lymph nodes using the CD4$^+$CD25$^+$ Regulatory T cell isolation kit (Miltenyi Biotec, Bergisch-Gladbach, Germany). First, lymphocytes were mixed with a cocktail of biotinylated antibodies against CD8, CD11b, CD45R, CD49b and Ter-119 and incubated with magnetic beads conjugated to anti-biotin antibody. Elution through a column under a magnetic field enriched the unlabeled CD4+ T cells. Next, CD25$^+$ cells were stained with PE-labeled monoclonal antibodies, mixed with anti-PE magnetic microbeads and positively selected by passage through a second column under a magnetic field. Purity was evaluated using FITC-labeled monoclonal antibodies.

In Vitro Apoptosis: A concentration of 2×10$^6$ cells/ml was prepared in DMEM supplemented with 2 mM L-glutamine, 1 mM sodium pyruvate, 13.6 μM folic acid, 270 μM L-asparagine, 548 μM L-arginine HCL, 10 mM HEPES, 50 μM 2β-Mercaptoethanol, 100 mg/ml streptomycin, 100 U/ml penicillin and 5% heat-inactivated fetal bovine serum (FBS) (MLR medium). All the ingredients were purchased from Beit Haemek and Sigma (St. Lois, Mo.). The cells were challenged by addition of 75-250 ng/ml streptavidin-FasL chimeric protein for 18-24 hours or CD25$^+$ T cells and apoptosis/death were determined by flow cytometry. Cell death and apoptosis were determined in cells incubated with 5 μg/ml 7-aminoactinomycin-D (7-AAD, Sigma, St. Lois, Mo.) and Annexin-V (IQ products, Groningen, The Netherlands).

Histology: Pancreata were excised from mice euthanized by CO$_2$ asphyxiation, and were fixed in ice-cold PBS containing 1.5% fresh paraformaldehyde for 2 hours at 0-4° C. before overnight immersion in 30% sucrose. Tissues were embedded in OCT (Sakura Finetek, Torrance, Calif.), frozen in isopentane suspended in liquid nitrogen, sectioned (3-6 μm) with a Cryotome (Termo Shandon, Cheshire, UK) and stained with hematoxylin and eosin.

For Immunohistochemistry, sections fixed in acetone (10 minutes at −20° C.) were permeabilized by incubation with 0.2% Saponin, 1% BSA and 0.1% Triton-100, stained with primary antibodies for one hour, washed and counterstained with respective secondary antibodies (30 minutes at room temperature). Nuclei were labeled with Hoechst-33342 (1:1000, Molecular Probes, Eugene, Oreg.), and sections were mounted in anti-fade medium (Dako, Glostrup, Denmark) and air-dried. Pancreatic cryosections were immunostained with primary antibodies: guinea pig anti-insulin (Dako), rat anti-mouse CD4 (BD Pharmingen), biotinylated anti-mouse CD45 (1:100, Biolegend, San Diego, Calif.), FITC-conjugated rat anti-FoxP3 antibody (eBioscience) and FasL was stained with a FITC-conjugated MFL4 antibody (BD Pharmingen). Primary antibodies against insulin and CD4 were counterstained with AlexaFluor-647 and AlexaFluor-555 secondary antibodies (Dako, eBioscience) respectively, and biotinylated antibodies were conjugated with Cy3-labeled Streptavidin (1:400, Jackson Immunoresearch, West Grove, Pa.). Brightfield and fluorescence images were collected with an Axioplan 2 Microscope (C. Zeiss, Göttingen, Germany).

Proliferation Assay: Cells were plated in plastic dishes ($5 \times 10^7$) and after 45 minutes the non-adherent lymphocytes were collected and washed. The lymphocytes were incubated at room temperature for 7 minutes with 10 µM 5-(and 6-)-carboxyfluorescein diacetate succinimidyl ester (CFSE, Molecular Probes, Carlsbad, Calif.), after which labeling was arrested by addition of 50% FCS and washed with PBS. Stained cells were cultured at 37° C. in a humidified 5% $CO_2$ atmosphere for 3 days in MLR medium containing 1% heat-inactivated mouse serum. Cells were stimulated with 5 µM concanavalin A (ConA, Sigma) and 20 units interleukin-2 (IL-2, Peprotech, London, UK) and were related to unstimulated cells. All proliferation assays were performed in triplicates. Suppression of T cell proliferation was performed in stimulated mixed cultures. Isolated $CD4^+CD25^-$ T cells were labeled with CFSE and stimulated with an equal number of CD3/CD28 beads (Invitrogen, Oslo, Norway). Proliferation was assessed after 48 hours with and without the addition of $CD4^+CD25^+$ T cells at various ratios. CFSE dilution was analyzed in flow cytometry by gating on the live lymphocytes and proliferation was quantified the ModFit software (Verity Software House, Topsham, Me.).

Adsorption of FasL Protein on the Surface of Cells: Cells were suspended in 5 µM freshly prepared EZ-Link Sulfo-NHS-LC-Biotin (Pierce, Rockford, Ill.) in PBS for 30 minutes at room temperature. After two washes with PBS the cells were incubated with streptavidin-FasL chimeric protein (100 ng protein/$10^6$ cells) in PBS. The efficiency of adsorption was evaluated by flow cytometry using primary goat anti-streptavidin mAb (Zymed, San Francisco, Calif.) counterstained with secondary porcine anti-goat IgG (R&D Systems, Minneapolis, Minn.), and anti-FasL antibodies (clone MFL-4, BD Pharmingen).

Determination of Blood Insulin: Serum from NOD mice was collected by centrifugation (no anti-coagulant) after clotting at room temperature for 30 min. Samples were assessed in 96 wells Microtiter Assay Plates (Millipore, Billerica, Mass.) using the Rat/Mouse Insulin ELISA Kit (R&D Systems, Minneapolis, Minn.). Absorbance at 450 nm and 590 nm was determined using an ELISA PowerWave-10 in a plate reader (BioTeK, Winooski, Vt.). Insulin standards were used to determine a calibration curve.

Inflammatory Bowel Disease Murine Model: Murine model of chronic colitis (lymphocytic) was induced in BALB/c mice by repeated cycles of 5% (w/v) dextran sodium sulfate (DSS) administration in drinking water (ad libitum): four cycles of 5 days DSS interrupted by 3 days of recovery [as previously described, see e.g. Yarkoni S. et al. Eur J Immunol (2009) 39:2850-64]. $3 \times 10^6$ $CD25^+$ T cells derived from the lymph nodes of mice with chronic colitis were administered at the onset of the third dextran sodium sulfate (DSS) cycle.

Murine Model of Graft Versus Host Disease: Sublethally irradiated (700 rad) F1 recipient mice ($H2K^{b/d}$) were grafted with $5 \times 10^6$ T cell depleted bone marrow cells (TCD-BMC) and $2 \times 10^7$ splenocytes from parent donors ($H2K^b$), simulating a haploidentical transplant.

Cardiac Tissue Grafting: Implantation of neonate hearts (1-2 days old) was performed using a modified procedure: hearts were dissected into two halves and were thoroughly washed with cold solution to remove residual blood. Ear pinna was pierced with a blunt 8 french needle to create a tunnel in between the skin and the cartilage and a liquid pouch was created by infusion of physiological solution. The heart was introduced using a plastic guide through the needle. Graft function was visually inspected at using a surgical stereoscope at low magnification. As allogeneic heart started to beat before acute rejection within a week, failure to assume spontaneous contraction was considered as technical failure.

EXAMPLE 1

Modulation of Autoimmune Diabetes in NOD Mice

Quantitative Variations in Treg Subsets in Prediabetic and Diabetic NOD Mice

Figure 1D:
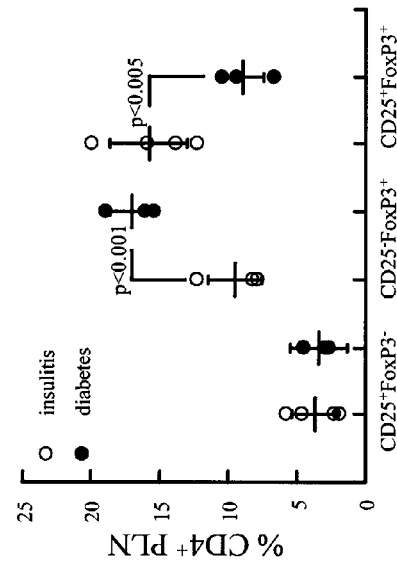
Figure 1A:
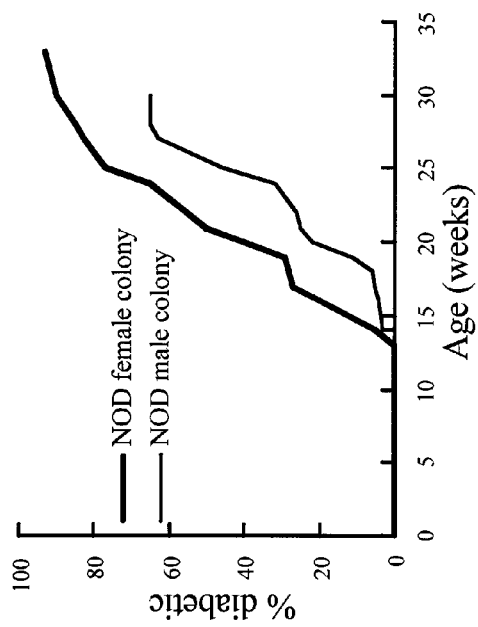
Figure 1C:
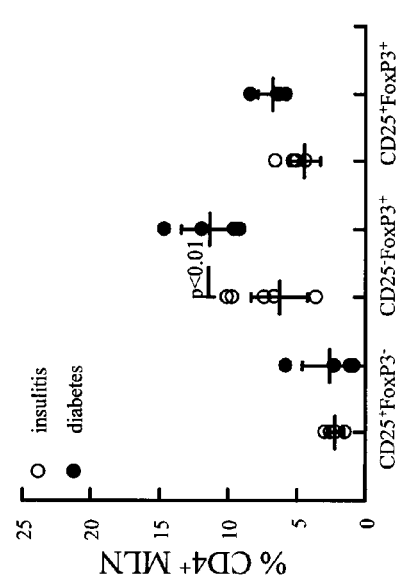
Figure 1F:
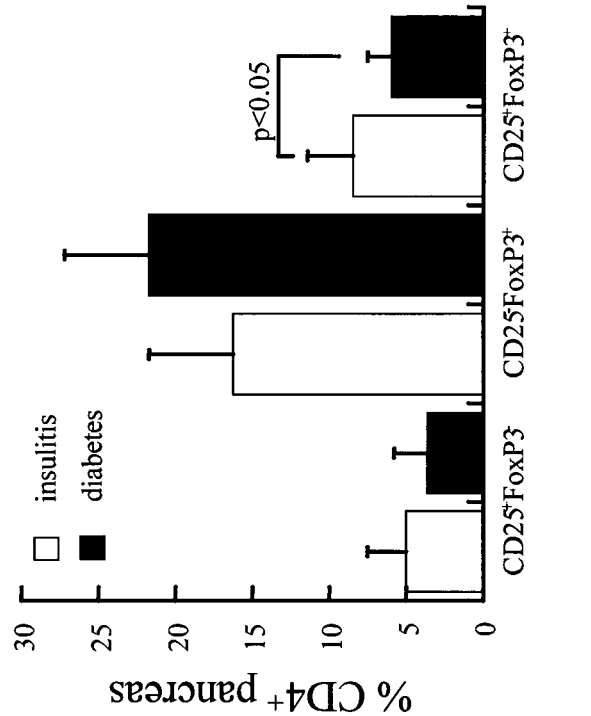
Figure 1E:
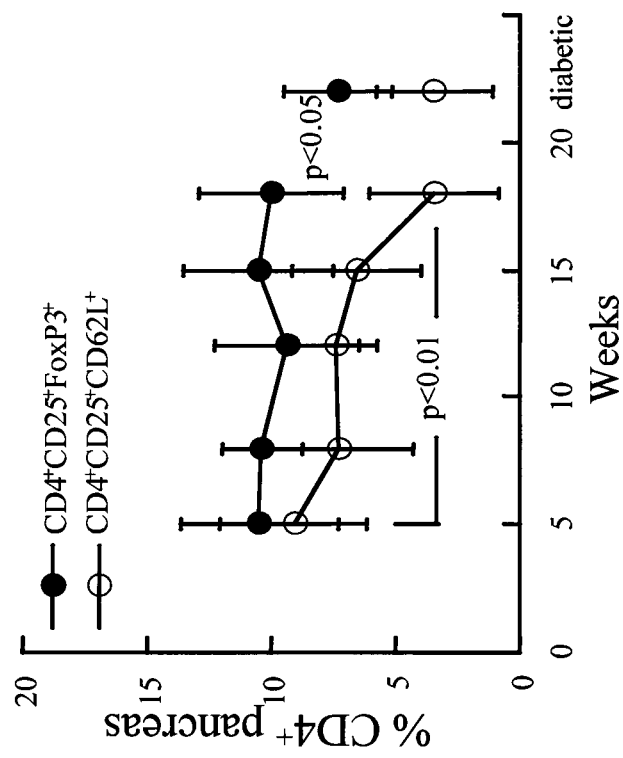

Immune imbalance in non-obese diabetic (NOD) mice and human diabetics has been attributed to a decline in the number of Treg, however this contention has been challenged in other studies. In the present study, female NOD colony overt hyperglycemia commenced at the age of 14 weeks and included 83% of the mice aged 30 weeks (FIG. 1A). Immune phenotyping of NOD females as a function of age revealed balanced distribution of $CD25^+FoxP3^+$ Treg, with an early decrease in and $CD25+CD62L^+$ Treg at early age (FIG. 1B). The variability in composition of inflammatory infiltrates was evident from the different profiles of the mesenteric (MLN, FIG. 1C) and pancreatic lymph nodes (PLN, FIG. 1D): increased $CD25^-FoxP3^+$ subsets were accompanied by reduced $CD25^+FoxP3^+$ Treg only in the PLN of diabetic NOD mice. These changes might originate from down-regulation of CD25 expression, possibly caused by IL-2 deficiency, which does not impair the suppressive activity of these cells. In the pancreatic infiltrates there was a substantial decrease in levels of cells expressing CD62L within the $CD4^+CD25^+$ subset, and a borderline decline in $FoxP3^+$ cells within this subset (FIG. 1E). Overall, there were minor differences in composition of the pancreatic infiltrates between prediabetic and diabetic NOD mice (FIG. 1F). The present data corroborated the steady levels of naturally occurring Treg cells expressing CD25 and FoxP3 in the peripheral lymphoid organs of NOD mice, similar to the steady levels in peripheral blood of human. Increased fractions of FoxP3+ Treg in the regional lymph nodes early after onset of diabetes might be reactive to the terminal stages of destructive insulitis, with marked variations in subsets expressing various putative Treg markers. For further experimentation the present inventors chose to focus on $CD4^+CD25^+$ Treg, the levels of which are relatively stable in advanced stages of inflammatory insulitis.

EXAMPLE 2

Sensitivity of CD4+ T Cells to Apoptosis is Affected by Isolation

Defective Treg function in diabetics has been attributed to the apparent increased susceptibility of these cells to apoptosis in vitro. However, measurements of apoptosis performed in isolated subsets showed a very different situation from the patterns of apoptosis of gated CD4$^+$ T cell subsets within mixed splenocyte populations. Whereas the sensitivity of CD25$^-$ naïve/effector T cells was stable, isolated CD25$^+$ Treg display markedly increased susceptibility to spontaneous apoptosis [FIGS. 2A-E, adapted from Kaminitz A. et al., PLoS One (2010) 31; 5:e15684]. Therefore, increased mortality of CD25$^+$ T cells was primarily a result of the isolation procedure, a technical bias caused by the absence of other cell subsets. In subsequent studies the present inventors have used measurements of gated populations within mixed cultures, which was a better surrogate to the inflammatory conditions under which these cells operate.

The present inventors identified two main factors that affect Treg susceptibility to apoptosis. The first mechanism was cytokine deprivation, primarily deficiency in IL-2, which is known to be an essential cytokine for Treg development and function. IL-2 is produced only by effector and some adaptive Treg, but not by naturally occurring Treg cells, and inhibition of IL-2 secretion from naïve/cytotoxic T cells is a major mechanism of Treg-mediated suppression. Exogenous supplementation of IL-2 reduced significantly spontaneous death of isolated CD25$^+$ T cells, and in parallel stimulated their proliferation in vitro (FIGS. 2F-G). It is likely that robust Treg cycling is one of the factors responsible for decreased fractional apoptosis by dilution the fraction of dead cells. This mechanism of protection of Treg viability by IL-2 is significant in regulation of the state of inflammation. Treg inhibit IL-2 production in effector T cells as a mechanism of suppression, increasing the susceptibility of effector cells to apoptosis through cytokine deprivation. Since peripheral Treg function is dependent on IL-2, the ensuing state of deficiency serves as a regulatory feedback mechanism that downsizes Treg function towards termination of the inflammatory reaction. Inventors do not exclude the possibility that the isolation procedure also induced deficiency in other cytokines released by adjacent cells that simulate the activity of IL-2 through activation of other receptors, although IL-2 deficiency has been associated with conditions of severe inflammation within the pancreatic islets.

An additional pathway of cell stimulation through the TCR receptor has significant consequences on the sensitivity to activation induced cell death (AICD), serving as survival signaling independent of IL-2. TCR associated stimulation by CD3 ligation has been widely used for cell activation, with and without associated CD28 co-stimulation. Exposure of CD4$^+$ T cells from wild type and diabetic NOD females to CD3/CD28 stimulation resulted in significant upregulation of CD25 but not FoxP3. CD3 and CD3/CD28 stimulation improved significantly Treg viability (FIG. 2H), indicating that these signals have the capacity to protect Treg cells in situ. These data were consistent with the observed reciprocal effects between Teff and Treg cells. Treg cells received anti-apoptotic signals in the form of IL-2, TCR activation and CD28 co-stimulation, while Teff were submitted to pro-apoptotic signals in mixed cultures, emphasizing that isolation procedure was a dominant drawback in evaluation of sensitivity to apoptosis. Furthermore, in the context of ongoing autoimmune reactions, these data emphasized the capacity of the microenvironment to modulate the susceptibility to apoptosis and AICD-type negative regulation.

EXAMPLE 3

Sensitivity of CD4+ Treg Cells to Fas-Mediated Apoptosis

Figure 3G:
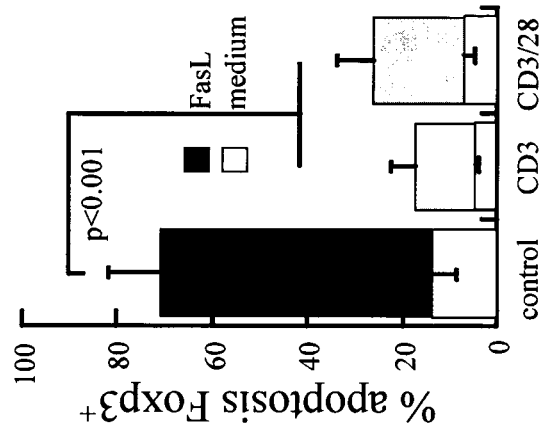
FIG. 3G is a graph illustrating apoptosis rates. Apoptosis was determined in control medium and with 50 μg/ml FasL under CD3 and CD3/CD28 stimulation in gated $FoxP3^+$ T cells (n=6) in mixed cultures of splenocytes from transgenic FoxP3-GFP mice [adapted from Kaminitz A, supra.
Figure 3F:
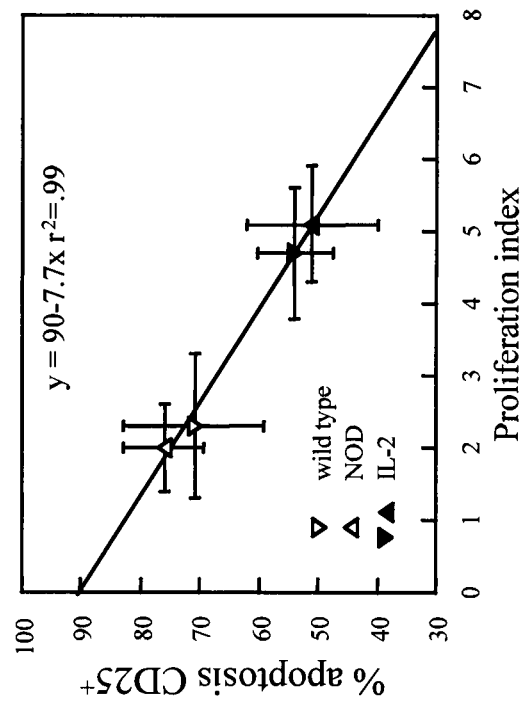
FIG. 3F is a graph illustrating fas-mediated apoptosis of $CD4^+CD25^+$ T cells in mixed cultures of splenocytes from NOD and wild type mice as a function of proliferation rates measured from CFSE dilution, with (n=4-5, closed triangles) and without (n=5-7) exogenous supplementation of IL-2 (open triangles, n=4-5) [adapted from Kaminitz A, supra]

Conflicting evidence has been reported in NOD mice and humans under various experimental conditions, ranging from resistance to excessive susceptibility of Treg to AICD. Most prior studies have used isolated Treg populations, disregarding the significant impact of reciprocal interactions between effector and suppressor T cells on sensitivity to apoptosis. Exposure of mixed cultures to FasL in vitro revealed that Treg are submitted to AICD-type negative regulation by Fas cross-linking [FIGS. 3A-E, adapted from Kaminitz A. et al., PLOS One (2011) 6:e21630]. Comparative analysis of apoptosis in gated subsets within mixed populations of splenocytes and lymph node cells showed similar sensitivity of CD25$^+$ Treg from NOD mice to spontaneous and Fas-mediated apoptosis as the CD25$^+$ and FoxP3$^+$ subsets in wild type mice (FIGS. 3A-E), suggesting that evolution of inflammatory insulitis is not caused by intrinsic deficits in AICD. To determine the relative sensitivities of Treg to apoptosis under stimulatory conditions, the same measurements were performed following supplementation of exogenous IL-2 and CD3/CD28 stimulation. IL-2 induced proliferation of CD25$^+$ Treg in vitro and reduced the sensitivity of Treg to Fas cross-linking (FIG. 3F). Likewise, FoxP3$^+$ Treg subsets displayed reduced susceptibility to Fas-cross-linking under CD3 and CD3/CD28 stimulation (FIG. 3G), indicating sustained viability by TCR-associated activation and costimulation. In variance from correlated cycling and sensitization to apoptosis of CD25$^-$ naïve/effector T cells by IL-2, proliferation and sensitivity to FasL were dissociated in CD25$^+$ Treg: IL-2 and CD3 stimulation cause dilution of dead cells due to robust expansion of viable cells. Uncoupling between proliferation and Fas-dependent negative regulation evolves as a particular Treg characteristic, which maintains viability of this subset with intrinsic state of activated suppressor activity under steady state conditions and evidently under inflammatory conditions.

Figures 3N, 3O, 3P:
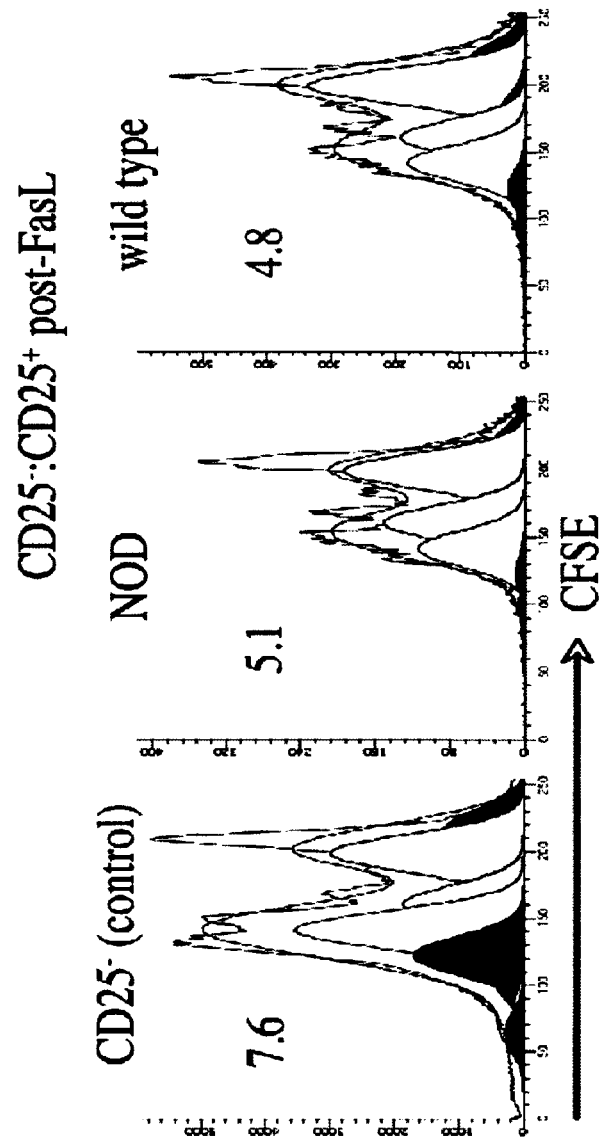

To determine whether FasL downregulates the suppressive activity of Treg in NOD and wild type mice, CD4$^+$ cells from the spleen and mesenteric/pancreatic lymph nodes were isolated in reference to CD25 expression (FIGS. 3D-M): immunomagnetically isolated CD4$^+$CD25$^+$ T cells (83% purity) expressed FoxP3 at high levels (84%), as compared to significantly lower expression in CD4$^+$CD25$^-$ T cells. CD4$^+$CD25$^+$ cells were exposed to the ligand prior to co-incubation with CD3/CD28 stimulated responders. These FasL-pre-exposed NOD Treg inhibited CD25$^-$ T cell proliferation similar to cells from wild type mice (FIGS. 3N-P), and importantly, the suppressive activity of Treg was not downsized by FasL in both strains. In addition to the demonstration that the suppressive activity of Treg is sustained following exposure to Fas-ligand, these data do not substantiate relative resistance of diabetogenic effectors to negative regulation in NOD mice.

EXAMPLE 4

Modeling Diabetes in Immuno-Compromised Mice

Figure 4B:
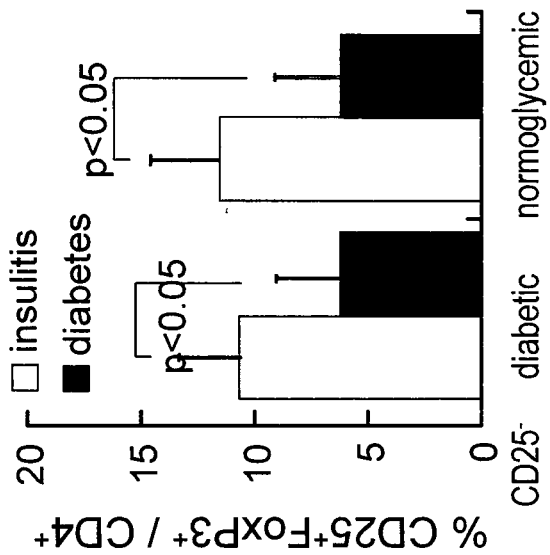
FIGS. 4A-F depict adoptive transfer of diabetes into NOD SCID mice.
Figure 4A:
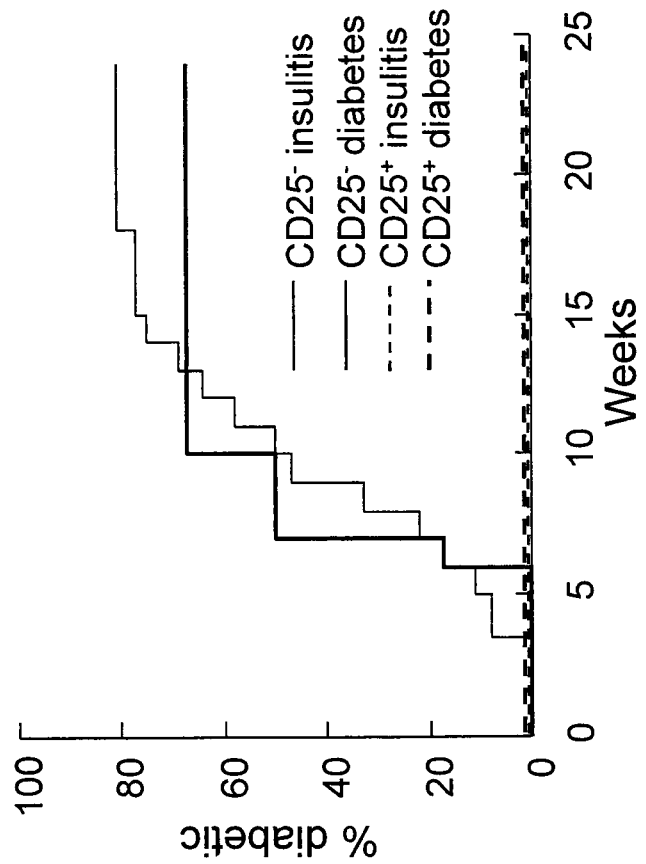
Figure 4D:
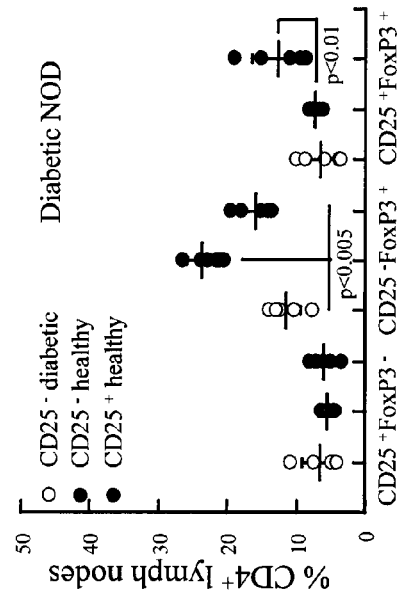

Autoimmune insulitis is effectively induced in immuno-compromised mice by adoptive transfer of immune cells, which expand robustly through lymphopenia-induced proliferation. Inventors questioned which T cells transfer the disease and whether there are differences in diabetogenic cell activity between prediabetic and new onset diabetic NOD females. Functional mechanisms considered to contribute to development of diabetes include decreased suppressive efficacy of Treg cells in aging NOD mice and human diabetics, and decreased susceptibility of pathogenic cells to Treg-mediated suppression in mice and human diabetics. Adoptive transfer of cells into (immuno-compromised) NOD SCID mice has the advantage of amplification of cell subsets through homeostatic expansion in lymphocyte-deficient hosts. Adoptive transfer of $2.5 \times 10^7$ CD25$^-$ T cells derived from spleens and mesenteric/pancreatic lymph nodes of prediabetic and diabetic NOD females induced the disease in NOD SCID mice at similar frequencies (FIG. 4A). In variance, $8 \times 10^6$ CD25$^+$ T cells from NOD mice at late stages of insulitis did not transfer the disease (FIG. 4A) and the islets were largely free of inflammation (not shown). Immune profiles of diabetic and normoglycemic mice revealed: a) In both diabetic and normoglycemic NOD SCID recipients of CD25$^-$ T cells from overtly diabetic NOD females the CD25+FoxP3+ Treg subset is lower than in recipients of cells from prediabetic donors (FIG. 4B), at similar incidence of disease induction. b) Adoptive transfer of CD25$^+$ T cells from prediabetic (FIG. 4C) and diabetic donors (FIG. 4D) resulted in increased fractions of CD25$^-$ FoxP3$^+$ T cells in the lymph nodes as compared to recipients of CD25$^-$ T cells. c) There were no significant differences in profiles of lymph nodes and pancreata of diabetic and normoglycemic NOD SCID mice adoptively transferred with CD25$^-$ T cells. The homeostatic expansion of T cells in NOD SCID mice gave rise to all subsets as evidence of dynamic expression of T cell markers, with relatively little influence of the nature of infused cells on the composition of lymphoid organs.

Figure 4F:
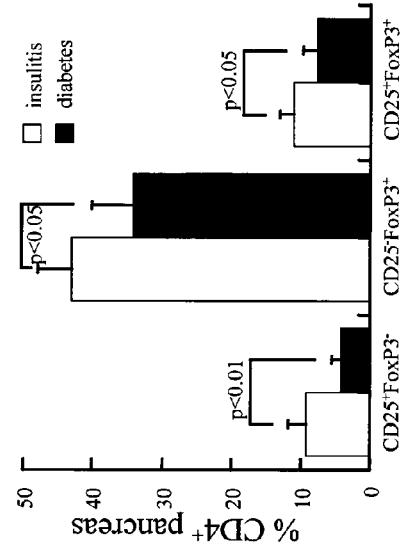
Figure 4C:
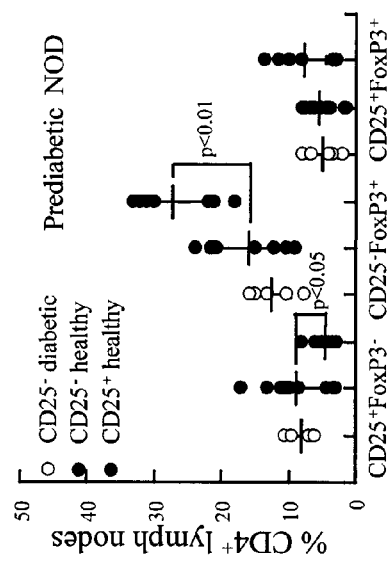
Figure 4E:
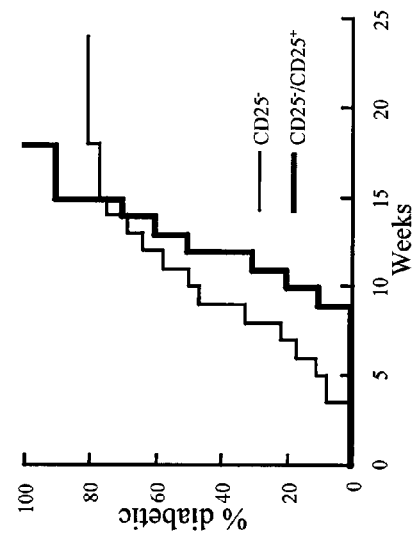

In the next stage, NOD SCID mice were co-adoptively transferred with a combination of CD25$^-$ and CD25$^+$ T cells. Adoptive transfer at a Teff:Treg ratio of 10:1 was ineffective in prevention of destructive insulitis (FIG. 4E). Consistent with adoptive transfer of CD25$^-$ T cells alone, recipients of cells from diabetic NOD females displayed reduced fractional reconstitution with T cells expressing CD25 and FoxP3 (FIG. 4F). Therefore, cells from diabetic mice appeared to be more restricted in induction of CD25$^+$FoxP3$^+$ Treg as compared to prediabetic NOD donors.

EXAMPLE 5

CD4+ Effectors are Submitted to Negative Regulation by Fas Cross-Linking

Relative resistance of naïve/effector T cells to AICD in NOD mice has been attributed a significant role in disease evolution through dominant effect of effector cells without true deficiency in regulatory cells. Reduced sensitivity of diabetogenic cells to negative regulation by AICD in NOD mice may be an intrinsic immune abnormality since thymocytes are also more resilient to apoptosis in NOD mice. For evaluation of the sensitivity to apoptosis inventors used FasL, which is a common executioner of apoptosis in the TNF superfamily. A previous study showed that exposure of T cells from NOD mice to FasL ex vivo decreased significantly their capacity of adoptive disease transfer into immunocompromized mice [Franke D D et al., Mol Immunol (2007) 44:2884-92]. The present inventors reproduced this result (FIG. 5A) and extended this finding by showing that direct decoration of diabetogenic effectors from new onset diabetic NOD females with FasL prior to adoptive transfer into NOD SCID mice reduced their activity in vivo [FIG. 5B, adapted from Kaminitz A. et al., PLOS One (2011) 6:e21630]. These data clearly demonstrate that diabetogenic T cells are sensitive to AICD mediated by Fas cross-linking in NOD mice.

Assessment of apoptosis of CD25$^-$ effector T cells from NOD mice, endowed with the potential of adoptive diabetes transfer, showed robust death induced by Fas cross-linking (FIG. 5C). In fact, naïve/effector T cells in prediabetic and diabetic NOD mice were as sensitive to Fas-mediated AICD as CD25$^-$ and Foxp3$^-$ T cells from wild type mice (FIG. 5C). To evaluate the influence of CD3/CD28 stimulation on cell sensitivity to Fas-mediated apoptosis, inventros used FoxP3 in mixed cultures, because this stimulation induced robust upregulation of CD25 expression (FIGS. 5D-G). Both CD3 activation and CD28 co-stimulation induced proliferation thereby decreasing fractional apoptosis (FIG. 5H). Consistent with reduced diabetogenic activity of cells under the influence of Fas ligation, these data do not substantiate resistance of effector T cells to apoptosis as a significant cause of inflammatory insulitis in NOD mice.

Taken together, these data indicate: (a) Cell isolation dominated the apparent sensitivity of Treg to apoptosis, due to removal of anti-apoptotic factors released from other cell subsets. (b) Increased Treg susceptibility to apoptosis was caused in part by cytokine withdrawal, in particular deficiency in IL-2. The protective effect of IL-2 on these cells within mixed cultures indicated that the full protective effect has not been reached because exogenous supplementation further supported Treg viability. (c) Suppressor CD4$^+$ T cell subsets were submitted to negative regulation by Fas-mediated AICD. (d) Treg in NOD and wild type mice were characterized by dissociation between proliferation and sensitivity to Fas cross-linking. (e) Diabetogenic T cells in NOD mice were responsive to negative regulation by Fas cross-linking and were as sensitive to AICD as cells from wild type mice. (f) FasL-mediated depletion of naïve/effector T cells reduced the diabetogenic activity. (g) Susceptibility to autoimmune insulitis in NOD mice could not be attributed to variations in sensitivity of both effector and suppressor subsets to negative regulation by Fas cross-linking.

EXAMPLE 6

Fas-Ligand Enhances Treg-Mediated Suppression In Vitro

Previous studies have indicated that reversible inhibition of effector cell function by Treg is suboptimal to abrogation of the diabetogenic potential, and the disease might persist and recur when the suppressive mechanisms are downregulated [see e.g. Klein L et al., Proc Natl Acad Sci USA (2003) 100:8886-8891]. The present inventors hypothesized that targeted simulation of the process of activation-induced cell death (AICD) at the site of inflammation would ameliorate inflammatory insulitis. For proof of concept of Treg-mediated cell killing as a mechanism of suppression, inventors used a chimeric FasL protein that could be conjugated to cell surfaces (killer Treg), to transduce apoptotic signals in an antigen-specific manner in cells only upon physical engagement and during the process of antigen presentation. First, inventors assessed the inhibitory activity of killer Treg in vitro. Co-incubation of CD25$^-$ T cells from prediabetic female NOD mice aged 14 weeks with escalating numbers of CD25$^+$ T cells resulted in graded inhibition of proliferation in response to CD3/CD28 stimulation (FIGS. 6A-D). Overexpression of FasL protein on the surface of CD25$^+$ cells further inhibited proliferation (p<0.05), increasing the effective suppressor activity at Treg:Teff ratios of 1:10 and 1:5 [FIGS. 6A-D, adapted from Kaminitz A et al., J Autoimmun (2011) 37:39-47] and induced apoptosis in a dose dependent manner (FIGS. 6E-G). Considering that effective suppression using naïve Treg cells required a minimal Treg:Teff ratio of 1:2 and a ratio of 1:9 attained with ex vivo expanded Treg cells, overexpression of FasL evolved as an effective mechanism of suppression with the advantage of definitive effector cell elimination.

EXAMPLE 7

Treg Cells and FasL Attenuate Adoptive Transfer of Diabetes

While the minimal effective Treg:Teff ratio documented was 1:2 to suppress adoptive transfer of diabetes [see e.g. Lepault F et al., J Immunol (2000) 164:240-7], effective suppression at a Treg:Teff ratio of 1:9 was observed with ex vivo expanded Treg cells (CD3/CD28 stimulation in the presence of very high IL-2 concentrations) [see e.g. Jaeckel E et al., Diabetes (2005) 54:306-310]. However, inhibition was attained at a lower ratio in antigen-specific Treg subsets (BDC2.5) whereas a Treg:Teff cell ratio of 1:5 cells from NOD mice was ineffective in blocking adoptive transfer of diabetes [Weber S E et al., J Immunol (2006) 176:4730-9]. Considering that Treg in diabetic mice and humans share islet-antigen-specific antigenic responsiveness with Teff and antigen-specific Treg are more potent than polyclonal Treg, inventors used Treg from age and sex-matched donors for inhibition of adoptive disease transferred into NOD SCID mice. Co-transfer of $2.5 \times 10^7$ $CD25^-$ and $2.5 \times 10^6$ $CD25^+$ T cells postponed the first disease occurrence to 9 weeks and delayed mean onset time (MOT) to 12.9±2.5 weeks (p<0.01 vs. 9.4±3.6 weeks with $CD25^-$ cells alone, FIG. 7A), but did not prevent disease progression. In contrast, overexpression of FasL protein on the surface of adoptively transferred $CD25^+$ T cells reduced the incidence of diabetes to 20% (2/10), demonstrating that FasL augments the suppressive function of $CD25^+$ cells in vivo. Analysis of the pancreas at the experimental end point showed significant reduction in severity of inflammation in mice that sustained glycemic control (FIGS. 7B-D), consistent with reduced disease incidence. Normoglycemic mice displayed high fractions of $CD25^+FoxP3^+$ Treg cells in the peripheral lymphoid organs (p<0.001 vs. naïve $CD25^+$ cells, FIG. 7E) and pancreatic infiltrates (p<0.01, FIG. 7F). These data associate overexpression of FasL with protection from adoptive disease transfer through increased fractions of Treg cells. Therefore, enforced FasL expression in $CD25^+$ T cells, which included naturally occurring and adaptive Treg, induced apoptosis of effector cells in vitro, and protected NOD SCID mice from adoptive disease transfer more efficiently compared to autocrine and paracrine apoptosis induced by death ligand expression on the effector cells (FIG. 5B).

EXAMPLE 8

FasL Attenuates the Course of Diabetes in Prediabetic NOD Mice

Figure 8A:
FIGS. 8A-O depict that killer Treg modulate the course of disease in prediabetic NOD females [adapted from Kaminitz A. et al., J Autoimmun (2011) 37:39-47].
Figure 8B:
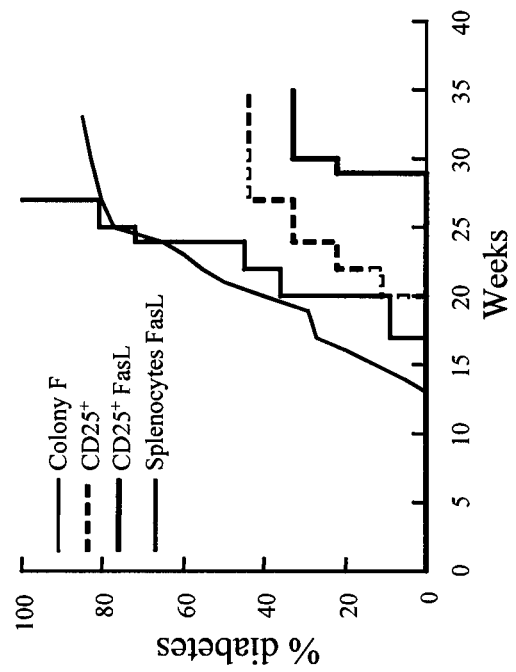
FIG. 8B is a photograph illustrating homing of CFSE-labeled CD25⁺ T cells (green) to the pancreatic lymph nodes delineated by the pan-hematopoietic marker CD45-PE (red). Immunohistochemistry was performed one day after adoptive cell transfer.
Figure 8L:
FIG. 8L is a photograph illustrating detection of CD4⁺FoxP3⁺ Treg within the inflammatory infiltrates cuffing the pancreatic islets in a 24-week old female NOD mouse.
Figure 8K:
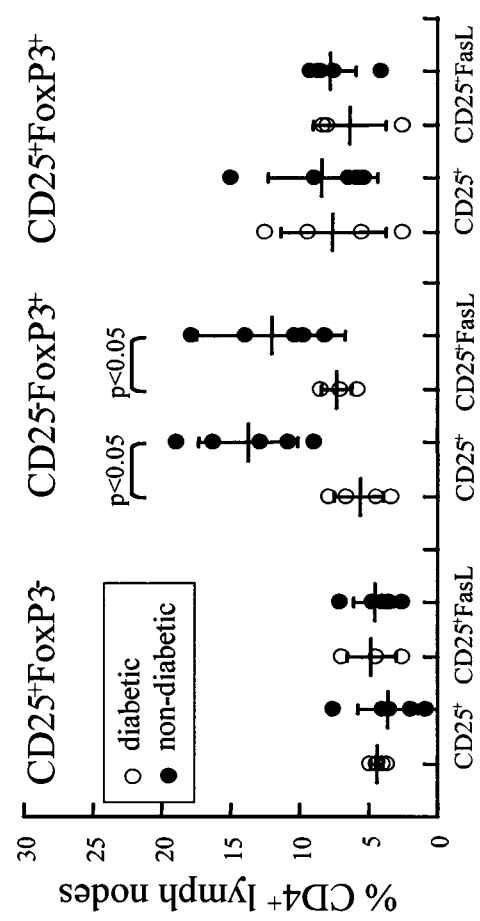
FIG. 8K is a graph illustrating fractional expression of CD25 and FoxP3 in the lymph nodes of NOD females adoptively transferred with naïve CD25⁺ T cells (4 diabetic and 5 non-diabetic) and FasL-coated CD25⁺ cells (3 diabetic and 5 non-diabetic)
Figure 9B:
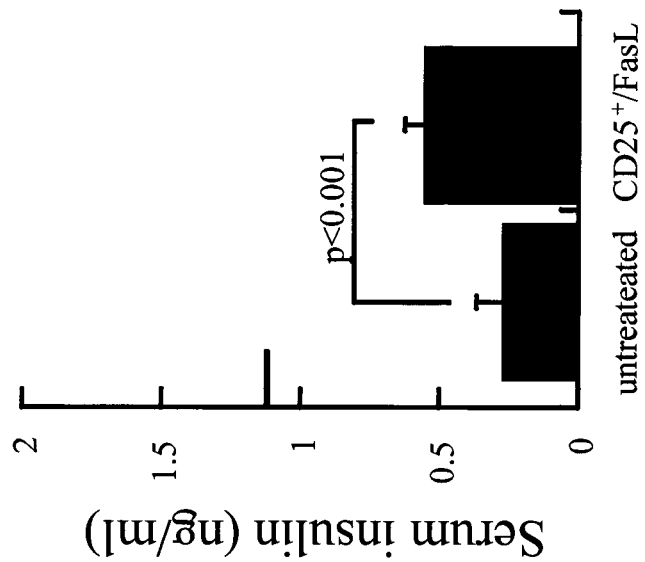
Figure 9A:
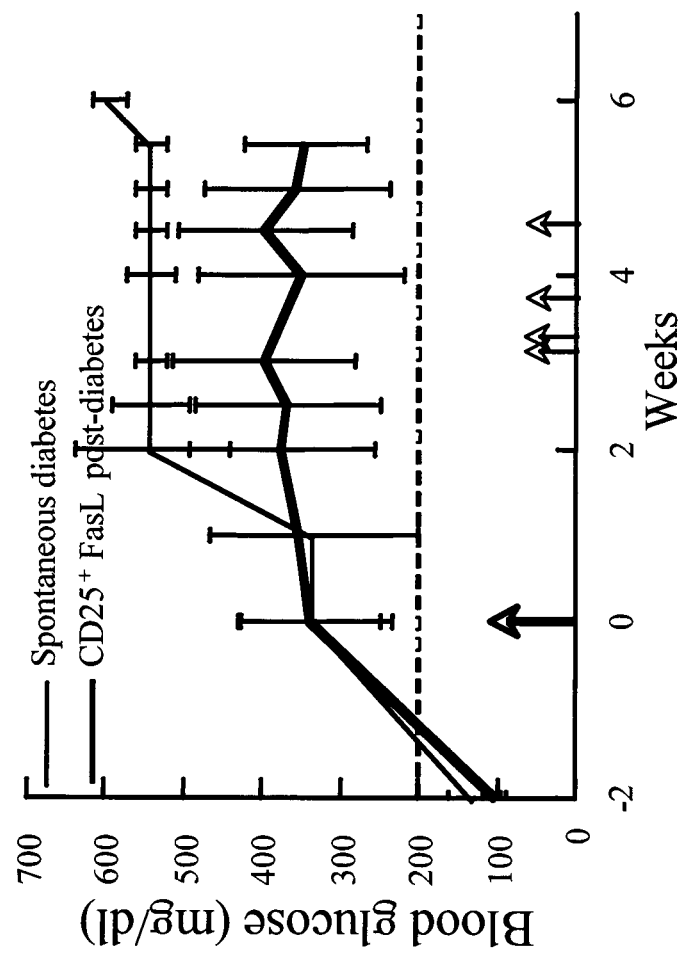

To determine the impact of killer Treg on the course of inflammatory insulitis, prediabetic NOD females were infused with $3-4 \times 10^6$ $CD25^+$ T cells coated with FasL protein. Adoptive transfer of naïve and FasL-coated $CD25^+$ T cells lowered the incidence of hyperglycemia to 33-44% (FIG. 8A). However, killer Treg caused a significant delay in disease appearance (P<0.005) with a mean onset time (MOT) of 29.3±0.7 weeks as compared to naïve Treg (MOT=23±2.7 weeks). To determine whether modulation of disease course is a consequence of bystander activity of FasL-coated cells, mice were infused with equivalent numbers of splenocytes expressing FasL. These cells did not affect the tempo of disease onset (MOT=22.6±2.7 weeks) as compared to the female colony, but all mice progressed to overt hyperglycemia. Modulation of disease course is therefore attributed both to suppressor T cells that reduced disease incidence and to FasL that caused a significant delay in disease onset.

To evaluate the mechanism of killer Treg activity, inventors first monitored the early events of homing of the infused cells to the target organs and their activity, considering that Treg are relatively limited in their navigation capacity as compared to Teff. Modulation of inflammation would be best achieved by direct homing of the killer Treg cells to the inflicted islets, in particular when the FasL protein persists in vivo for short periods of time ($t_{1/2}$~4 days). FasL-coated $CD25^+$ T cells labeled with CFSE and PKH membrane linkers homed to the regional lymph nodes (FIG. 8B) and to the pancreatic islets (FIGS. 8C-F) early after administration, emphasizing efficient homing of syngeneic Treg to the site of inflammation. Flow cytometric analysis of the pancreatic infiltrates showed similar homing efficiency of naïve and FasL-coated Treg, which proliferated early after homing to the pancreas (FIGS. 8C-F). The infused cells consisted of 11.5±2.8% and 15±4.2% of $CD4^+FoxP3^+$ cells in pancreata and lymph nodes, respectively, representing a relatively small fraction of the endogenous FoxP3 subset. Recipients of killer Treg displayed increased fractions of apoptotic $CD25^-$ T cells (8.2±2.4%) as compared to naïve Treg (1.2±0.7%) (p<0.001, FIGS. 8G-J), indicating that the protective effect of killer Treg was mediated by early depletion of naïve/effector cells at the site of inflammation and reduced pathogenic burden. These data indicate that the significant clinical outcome is achieved primarily through immunomodulation rather than adjustment of the local Teff: Treg ratio by quantitative contribution of the infused cells. The proposed explanation is based on antigen-specific sensitization of Treg in NOD mice, which: (a) facilitated their navigation to the target organ, (b) initiated Treg proliferation, which depends on T cell receptor (TCR) stimulation, (c) suppressed cytotoxic cell activity in an antigen-specific manner, and (d) mediated antigen-specific depletion of autoreactive immune cells at the site of inflammation.

Figures 8M, 8N, 8O:
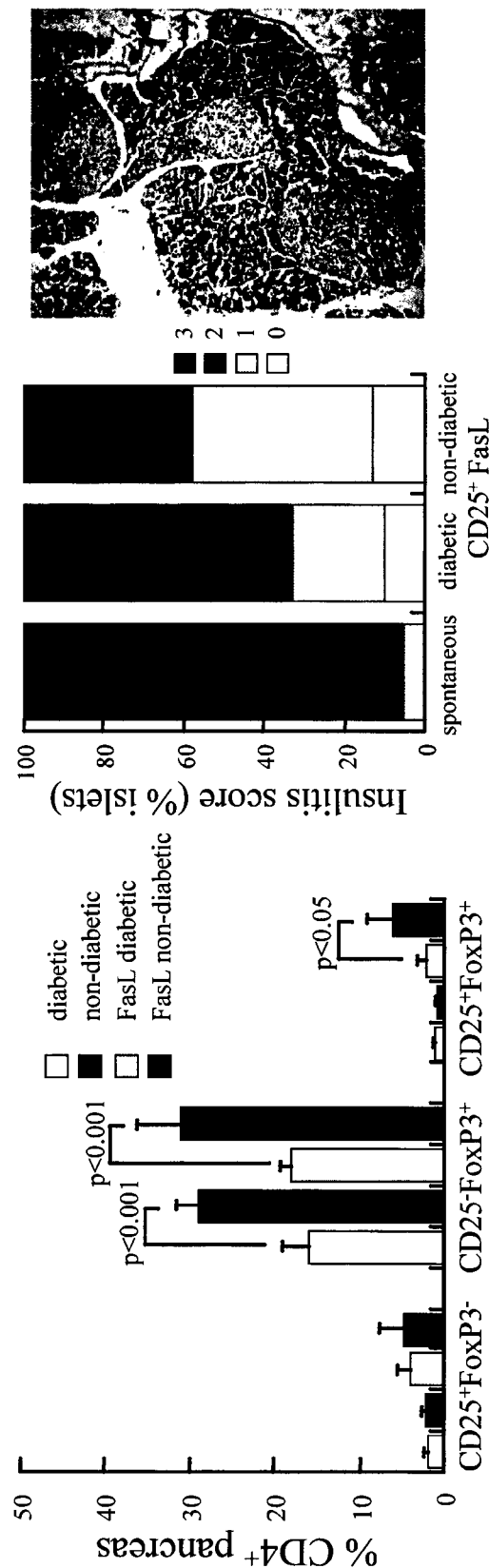
FIG. 8M is a graph illustrating fractional expression of CD25, FoxP3 and their combination in pancreatic inflammatory infiltrates in NOD mice after infusion of naïve CD25⁺ T cells (4 diabetic and 5 non-diabetic) and FasL-coated CD25⁺ cells (3 diabetic and 5 non-diabetic)
FIG. 8N is a graph illustrating insulitis score representing spontaneous diabetes (40 islets from 3 mice), diabetic (69 islets from 3 mice) and non-diabetic (80 islets from 4 mice) NOD females immunomodulated with FasL-coated CD25⁺ T cells: 0—no inflammation, 1—peri-insulitis, 2—inflammatory infiltration less than 50% of islet area, 3-inflammation more than 50% of islet area and islet structure disruption.

Long-term consequences of immunomodulation were assessed at the experimental end point in the pancreas and draining lymph nodes. Normoglycemic recipients of both naïve and killer Treg presented enriched $CD25^-FoxP3^+$ subset in the regional lymph nodes (p<0.05 vs. diabetic, FIG. 8K) and much more pronounced enrichment in this subset in the pancreas (p<0.001 vs. diabetic, FIGS. 8L-M). Only recipients of killer Treg displayed elevated contents of $CD25^+FoxP3^+$ T cells in the pancreas (p<0.05, FIG. 8M), which was confirmed by immunohistochemical analysis of the tissue. Taken together, enrichment in $CD4^+$ T cells expressing markers of naturally occurring Treg in the pancreas and regional lymphatics are directly linked to reduced severity of islet inflammation, associated with delayed onset and reduced incidence of overt hyperglycemia. Adoptive transfer of killer Treg resulted in reduced inflammatory scores of islets of prediabetic NOD females, which were more pronounced in mice that sustained glycemic control (FIGS. 8N-O).

EXAMPLE 9

FasL Attenuates the Course of Diabetes after Onset of Hyperglycemia

Few studies have succeeded to ameliorate the course of autoimmune insulitis after onset of hyperglycemia, when the reserve is about 20% of the β-cell mass. Typically, large numbers of naïve or ex vivo expanded Treg were required to arrest autoimmune insulitis, which was achieved primarily by ex vivo expansion (see e.g. Klein L. et al., supra). In view of the data gathered in prediabetic NOD females, inventors reasoned that large numbers of Treg might be substituted by a smaller number of killer Treg. Adoptive transfer of 3–4×$10^6$ FasL-coated $CD25^+$ T cells stabilized the blood glucose levels (FIG. 9A), and delayed the progression to high blood glucose levels to 36.3±7.9 days ($p<0.005$ vs. untreated mice). Similar to decreased incidence of overt hyperglycemia in prediabetic mice (40%) after administration of killer Treg, 3 out of 7 mice sustained blood glucose levels of about 350 mg/dl for periods exceeding 6 weeks. Stable blood glucose of about 350 mg/dl in the treated mice was consistent with higher serum insulin levels (FIG. 9B), suggesting that killer Treg slowed the pace of destructive insulitis.

Infusion of killer Treg into new onset diabetic NOD mice resulted in a marked increase in $CD25^-FoxP3^+$ T cells in the lymph nodes ($p<0.01$, FIG. 9C), without apparent modulation of the $CD25^+FoxP3^+$ subset. Importantly, adoptive transfer of killer Treg increased significantly the thymic contents of $CD4^+$ T cells expressing either CD25 ($p<0.01$) or FoxP3 ($p<0.001$, FIG. 9D), suggesting that cell enrichment in the periphery was partially due to thymic export of regulatory subsets. Stabilization of glucose levels induced by infusion of killer Treg after onset of overt hyperglycemia was accompanied by a marked increase in $CD25^-FoxP3^+$ T cells in the pancreatic infiltrates (FIG. 9E). Although pancreatic islets display marked structural and inflammatory variability in advanced stages of autoimmune insulitis, the quantitative increase in $FoxP3^+$ T cells caused by immunomodulation was confirmed by more abundant FoxP3 expression in some regions of pancreas (FIGS. 9F-G). These data correlate the stable glucose and the elevated insulin levels to relative dominance of $FoxP3^+$ Treg in the inflamed pancreas. These data demonstrate that Treg can serve as vehicles for targeted delivery of apoptotic signals, extending the period of time that might be required for implementation of therapies aiming to indefinitely abrogate autoimmunity. Slowing and arresting autoimmunity prior to extinction of the β cell mass is particularly important for approaches to regenerate the pancreas and restore glycemic control.

EXAMPLE 10

Lymphodepletion is Detrimental to Immunomodulation

Figure 10A:
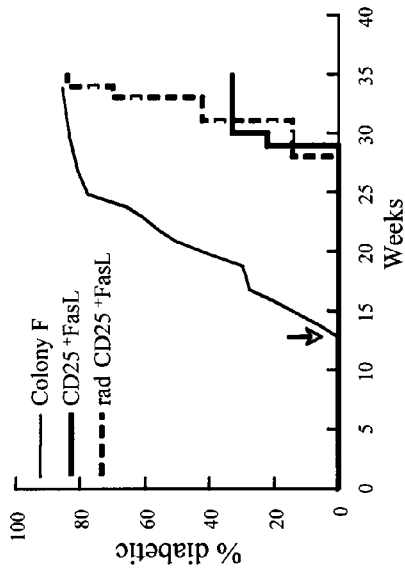
FIGS. 10A-D depict the detrimental impact of lymphodepletion on immunomodulation with killer Treg.
Figure 10B:
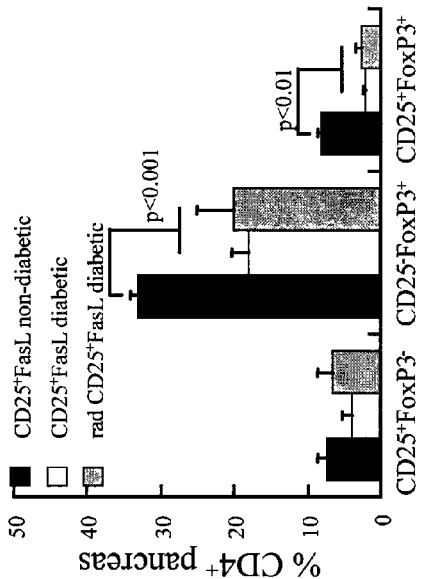
Figure 10C:
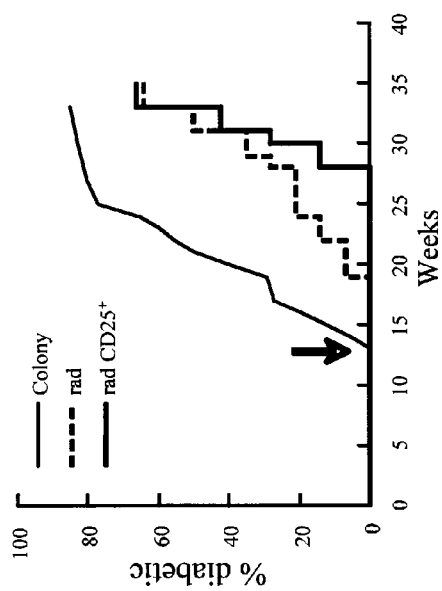
Figure 10D:
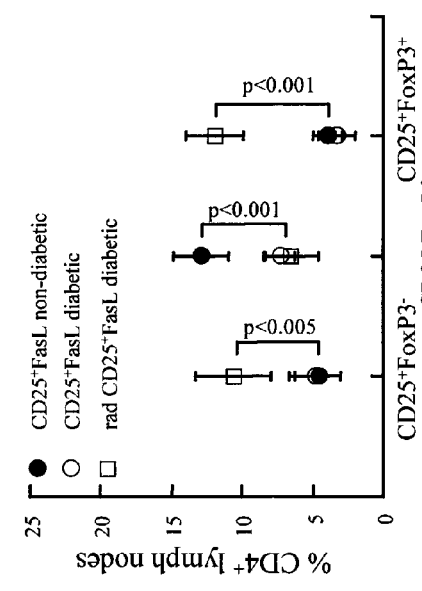

Because the immunomodulatory activities of $CD25^+$ T cells and FasL were effective early after adoptive transfer, inventors reasoned that selective lymphoid reconstitution of lymphopenic mice might be more effective. In recent studies inventors have demonstrated that sublethal irradiation postpones the onset of overt hyperglycemia, however destructive insulitis proceeds in two thirds of the mice [FIG. 10A, adapted from Kaminitz A et al., J Autoimmun (2010) 35:145-52]. Furthermore, adoptive transfer of splenocytes triggered diabetes and naïve $CD25^+$ Treg postponed the disease onset without affecting its incidence [Kaminitz A et al., supra]. Likewise, adoptive transfer of killer Treg into sublethally irradiated NOD females postponed disease onset but abolished the protective effect of these cells in 65% of the mice, resulting in full disease expression (FIG. 10B). Radiation-induced lymphopenia was accompanied by increased fractional expression of CD25 in both $FoxP3^-$ and $FoxP3^+$ subsets as compared to non-irradiated recipients (FIG. 10C), which is likely caused by lymphopenia-induced proliferation of the adoptively transferred cells. The pancreatic infiltrates of irradiated mice displayed reduced FoxP3+ subsets, with and without accompanying CD25 expression, resembling the profiles of non-irradiated mice that became diabetic after adoptive transfer of killer Treg (FIG. 10D). Evidently, lymphopenia induced by sublethal irradiation abolishes the protective effect of killer Treg and paradoxally reduces the fractions of naturally occurring Treg in the pancreas. The likely mechanism is the robust preferential expansion of naïve/effector T cells under lymphopenia, including residual diabetogenic clones, which proliferate without adequate surveillance by peripheral mechanisms of negative regulation. Dominant expansion of naïve/effector cells and delayed recovery of Treg after generalized lymphodepletion is common to failure of autologous immunohematopoietic reconstitution to reset immune homeostasis an abolish the diabetogenic activity in NOD mice. It is therefore essential to apply killer Treg-mediated immunomodulation in the absence of immunosuppressive therapy and preexisting lymphopenia.

EXAMPLE 11

Immunomodulation of Inflammatory Bowel Disease

Figures 11A, 11B:
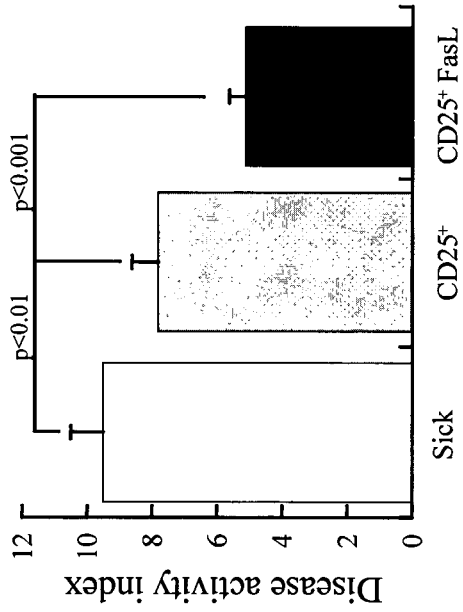
FIGS. 11A-F depict that killer Treg modulate the course of inflammatory bowel disease. Mice were fed with Dextran Sodium Sulfate (DSS) ad libitum in drinking water for 7 days (sick) and were infused on day 4 with $3 \times 10^6$ naïve and FasL-coated CD25+ T cells.
Figure 11D:
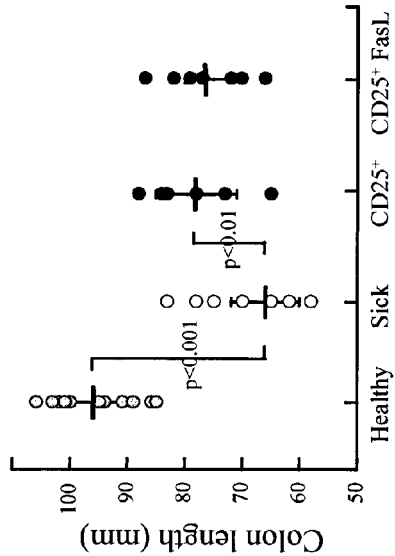
Figure 11F:
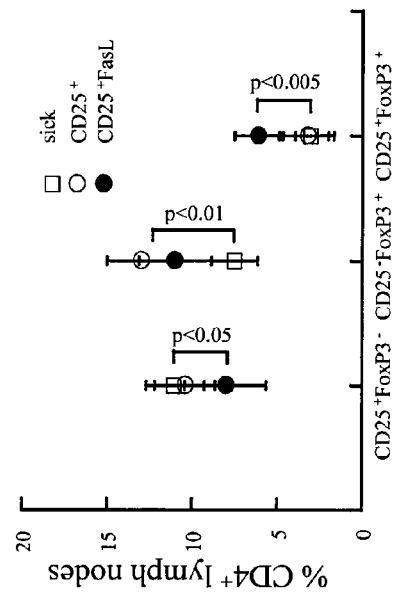
Figure 11C:
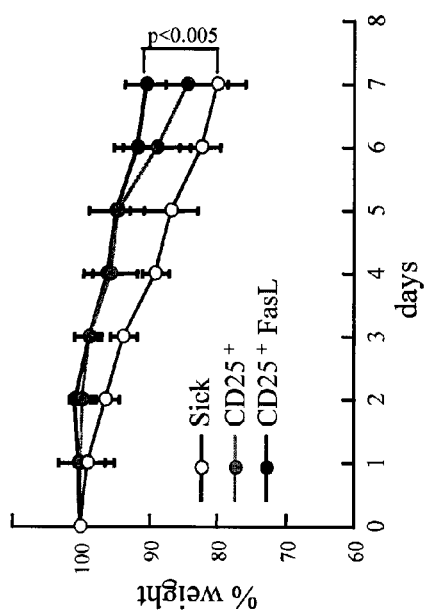
Figure 11E:
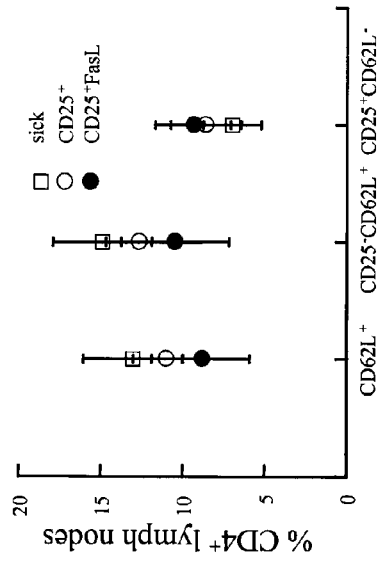

Inflammatory bowel disease (IBD) is difficult to simulate in murine models, considering the multiple aberrations in regulation of apoptosis that characterize colitogenic cells in patients. Colitogenic activity has been activated by IL-2 neutralization, by adoptive transfer of lymphocytes from bacteria-challenged wild type mice into immunocompromised recipients and by exposure to toxins. Because neutrophil activation is dominant in models of toxic colitis and lymphocyte activation is secondary, CD25+ T cells were harvested from a model of chronic colitis (lymphocytic) induced by repeated cycles of dextran sodium sulfate (DSS) administration (as described in detail in the materials and experimental procedures section, above). BALB/c mice were administered 5% (w/v) DSS in drinking water (ad libitum), and infused at the onset of the third cycle with $3\times10^6$ $CD25^+$ T cells derived from the lymph nodes of mice with chronic colitis. Killer Treg had a significant protective effect on disease activity score (FIGS. 11A-B), exceeding the benefit conferred by naïve Treg, which was also evident from better preserved body weight (FIG. 11C). Reduced disease activity score was consistent with preservation of colon length (FIG. 11D), reduced fractions of colitogenic $CD4^+CD62L^+$ T cells and increased fractions of suppressor $CD25^+CD62L^-$ T cells in the mesenteric lymph nodes (FIG. 11E). More significant differences were observed in fractions of naturally occurring $CD4^+CD25^+FoxP3^+$ Treg and a general trend in fractional FoxP3 expression in the mesenteric lymph nodes (FIG. 11F). Consistent with the lower disease activity score, increased representation of suppressor cells after immunomodulation with killer Treg cells suggest effective depletion of pathogenic cells.

EXAMPLE 12

Graft Versus Host Disease

Figure 12B:
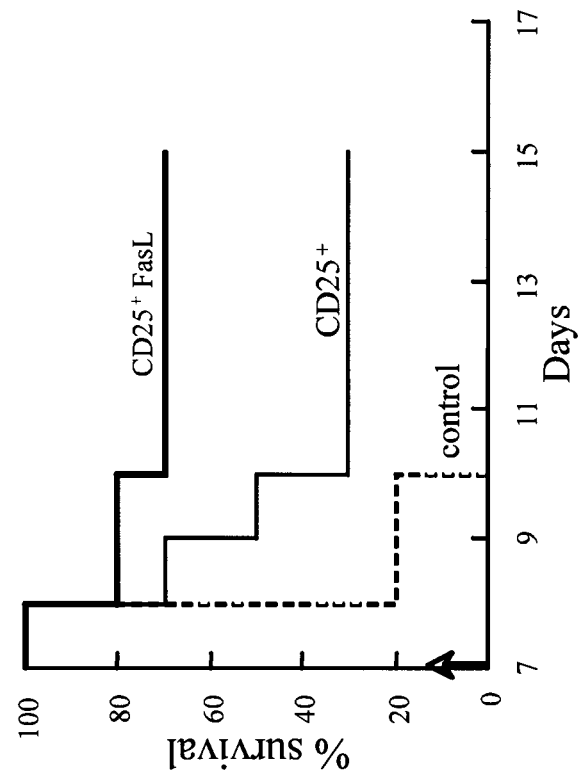
Figure 12A:
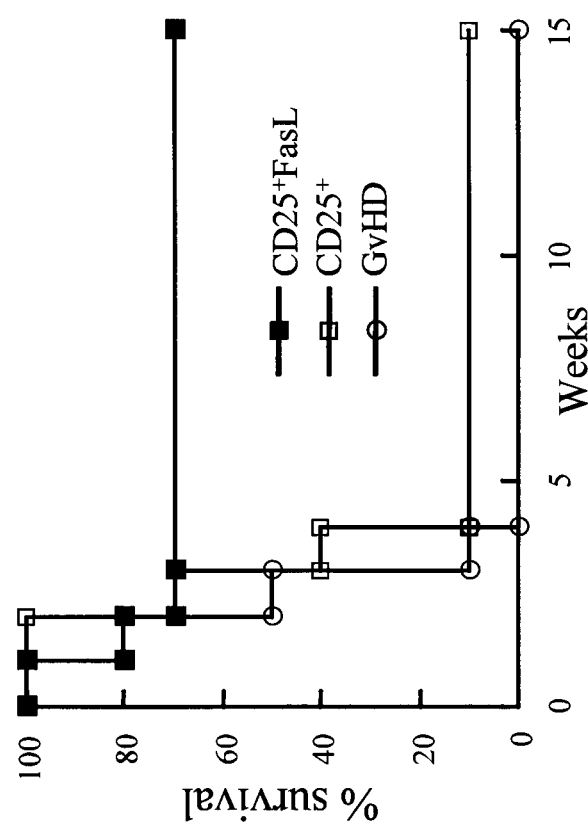

Graft versus host disease (GVHD) is mediated by mature donor T cells, which can be prevented by depletion of these cells from the donor inoculum. However, donor T cells play a significant role in support of hematopoietic cell engraftment, and their absence may lead to failure of engraftment or rejection. Prior studies have demonstrated that adoptive transfer of donor Treg ameliorates GVHD without impairing the graft versus tumor activity of the allograft. Inventors used a murine model of GVHD (as described in detail in the materials and experimental procedures section, above). All mice grafted under these conditions displayed lethal GVHD and died within 4 weeks (FIG. 12A). While adoptive transfer of $4 \times 10^6$ CD25$^+$ T cells (1:5 Treg:splenocyte ratio) had an insignificant protective effect, adoptive transfer of the same number of FasL-coated CD25$^+$ T cells rescued 70% of the mice (FIG. 12A). To refine the effect of killer Treg on survival, mice were challenged with 10 µg lipopolysacharide (LPS) at 7 days post transplantation, a procedure that causes ubiquitous mortality due to fulminant GVHD within 3 days. Adoptive transfer of CD25+ T cells rescued 30% of the mice, whereas killer Treg rescued 70% of the mice from lethal LPS challenge (FIG. 12B). These significant variations in disease severity were accompanied by decreased histological score of GVHD (FIG. 12C) and reduced weight loss (FIG. 12D), two of the prominent features of acute GVHD. Immunophenotyping of the lymphoid organs revealed increased CD25 expression in the spleen (FIG. 12E) and increased FoxP3 expression in the lymph nodes (FIG. 12F), consistent with an overall increase in fractions of CD25$^+$FoxP3$^+$ Treg cells. These data demonstrate that killer Treg are effective in protecting from acute GVHD to the extent of rescue of affected recipients, in addition to the therapeutic effect of Treg that expand effectively under lymphopenic conditions in wild type mice. The current data suggest that ex vivo expansion of donor Treg might be obviated and/or complemented by enhancing the killing capacity of donor Treg, which selectively and specifically eliminate pathogenic cells at sites of inflammation triggered by GVHD.

EXAMPLE 13

Induction of Transplant Tolerance

Adoptive transfer of donor and host Treg augments induction of transplant tolerance and confers protection to the allografts. Inventors used a model of non-vascularized heterotopic neonatal heart grafts into the ear pinna, to evaluate the tolerogenic effect of Treg cells. Whereas allogeneic heart grafts (H2K$^b$→H2K$^d$) were acutely rejected, the grafts continued to contract for extended periods of time when implanted 2 weeks after transplantation of bone marrow cells from the same donor (FIG. 13A). In variance, only a fraction of the hearts sustained contraction when implanted simultaneous with the bone marrow transplant, an approach that may be easier adopted to the clinical setting. Adoptive transfer of donor CD25+ T cells was performed 2 days after simultaneous heart-BMT transplantation, a period of acute activation of alloreactive responses responsible for allograft rejection. Unmanipulated (naïve) donor CD25+ T cells improved graft survival, and killer Treg resulted in prolonged survival of all the cardiac tissue grafts (FIG. 13B). Taken together these data demonstrate superior efficacy of killer Treg in abrogating allograft rejection in conjunction with simultaneous BMT, although radiation-induced lymphopenia without transplantation of bone marrow cells was rather detrimental to the activity of killer Treg (FIG. 10B). Enhanced killing activity of Treg, possibly applied in conjunction with strategies designed to expand these cells.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of treating a medical condition selected from the group consisting of: diabetes mellitus type I, inflammatory bowel disease, graft versus host disease and transplant rejection in a subject in need thereof, the method comprising: a) recombinantly expressing or immobilizing FasL ex vivo on the surface of isolated CD4+CD25+ regulatory T cells, thereby generating isolated CD4+CD25+ regulatory T cells overexpressing FasL; b) administering to the subject a therapeutically effective amount of a pharmaceutical composition comprising said isolated CD4+CD25+ regulatory T cells overexpressing FasL, thereby treating the medical condition.

2. The method of claim 1, wherein said CD4+CD25+ regulatory T cells overexpressing FasL are autologous or allogeneic.

3. The method of claim 1, wherein said CD4+CD25+ regulatory T cells overexpressing FasL are cultured, expanded, activated or stimulated prior to administration to the subject.

4. The method of claim 1, wherein said CD4+CD25+ regulatory T cells overexpressing FasL are antigen-specific.

* * * * *